United States Patent [19]
Van Gorcom et al.

[11] Patent Number: 5,863,533
[45] Date of Patent: Jan. 26, 1999

[54] CLONING AND EXPRESSION OF MICROBIAL PHYTASE

[75] Inventors: Robert F.M. Van Gorcom; Willem Van Hartingsveldt, both of Delft; Petrus Andreas Van Paridon, Noordwijk; Annemarie Eveline Veenstra, Nieuw Vennep; Rudolf G.M. Luiten, Leiden; Gerardus C.M. Selten, Berkel en Rodenrijs, all of Netherlands

[73] Assignee: Gist-brocades, N.V., Netherlands

[21] Appl. No.: 419,448

[22] Filed: Apr. 10, 1995

Related U.S. Application Data

[62] Division of Ser. No. 151,574, Nov. 12, 1993, Pat. No. 5,436,156, which is a continuation of Ser. No. 688,578, filed as PCT/NL90/00140 Sep. 27, 1990, abandoned.

[30] Foreign Application Priority Data

Sep. 27, 1989 [EP] European Pat. Off. .............. 89202436
Aug. 17, 1990 [EP] European Pat. Off. .............. 90202231

[51] Int. Cl.$^6$ .............................. A61K 38/46; C12P 3/00; C12N 9/16
[52] U.S. Cl. .......................... 424/94.6; 435/168; 435/196
[58] Field of Search .................................... 435/196, 168, 435/171; 424/94.6

[56] References Cited

U.S. PATENT DOCUMENTS 3,297,548  1/1967  Ware et al. .............................. 435/196

FOREIGN PATENT DOCUMENTS 0 287 152  10/1988  European Pat. Off. .
0 321 004  6/1989  European Pat. Off. .

OTHER PUBLICATIONS

Graf, E. ed., *Phytic Acid: Chemistry and Applications* (1986) Pilatus Press, Minneapolis, MN, Chapter 2, pp. 23–42.
Powar et al., "Purification and Properties of Phytate–Specific Phosphatase from *Bacillus subtilis*" *J. Bacteriol.* (1982) 151:1102–1108.
Cosgrove, "Inositol Phosphate Phosphatases of Microbiological Origin. Inositol Phosphate Intermediates in the Dephosphorylation of the Hexaphosphates of Myo–Inositol, Scyllo–Inositol, and D–Chiro–Inositol by a Bacterial (Pseudomonas Sp.) Phytase" *Aust. J. Biol. Sci.* (1970) 23:1207–20.
Nayini et al., "The Phytase of Yeast" *Lebensmittel Wissenschaft und Technologie* (1984) 17:24–26.
Yamada et al., "Phytase from *Aspergillus terreus*" *Agr. Biol. Chem.* (1968) 32(10):1275–1282.
Nelson et al., "Effect of Supplemental Phytase on the Utilization of Phytate Phosphorus by Chicks" *J. Nutrition* (1971) 101:1289–1294.
Han, "Use of Microbial Phytase in Improving the Feed Quality of Soya Bean Meal" *Animal Feed Sci. & Technology* (1989) 24:345–350.
Product Information Brochure published by Alko Ltd., entitled "Finase™ Enzymes by Alko" Rajamaki, Finland, 4 pages total, date not available.
Ullah, "Production, Rapid Purification and Catalytic Characterization of Extracellular Phytase from *Aspergillus Ficuum*" *Preparative Biochem.* (1988) 18(4):443–458.
Ullah, Enzyme and Engineering Conference IX, Oct. 4–8, 1987, Santa Barbara, CA (poster presentation) 2 pages total.
Ullah, "*Aspergillus Ficuum* Phytase: Partial Primary Structure, Substrate Selectivity, and Kinetic Characterization" *Preparatory Biochem.* (1988) 18(4):459–471.
Ullah et al., "Extracellular Phytase (E.C. 3.1.3.8) from *Aspergillus Ficuum* NRRL 3135: Purification and Characterization" *Preparative Biochem.* (1987) 17(1):63–91.
Mullaney et al., *Filamentous Fungi Conference* (Apr. 1987) Pacific Grove, CA (poster presentation) 15 pages total.

*Primary Examiner*—Keith D. Hendricks
*Attorney, Agent, or Firm*—Morrison & Foerster LLP

[57] ABSTRACT

A nucleotide sequence encoding phytase has been isolated and cloned. The coding sequence has been inserted into an expression construct which in turn has been inserted into a vector capable of transforming a microbial expression host. The transformed microbial hosts may be used to economically produce phytase on an industrial scale. The phytase produced via the present invention may be used in a variety of processes requiring the conversion of phytate to inositol and inorganic phosphate.

10 Claims, 34 Drawing Sheets

N-TERMINAL AMINOACID SEQUENCES

| Position | A | B | C |
|---|---|---|---|
| 01 | | | LEU |
| 02 | | | ALA |
| 03 | | | VAL |
| 04 | | | PRO |
| 05 | | ALA | ALA |
| 06 | | SER | SER |
| 07 | | --- | ARG |
| 08 | ---** | --- | ASN |
| 09 | GLN | GLN | GLN |
| 10 | SER | SER | SER |
| 11 | SER | SER | SER |
| 12 | --- | --- | GLY |
| 13 | ASP | ASP | ASP |
| 14 | THR | THR | THR |
| 15 | VAL | VAL | VAL |
| 16 | ASP | ASP | ASP |
| 17 | GLN | GLN | |
| 18 | | GLY | |
| 19 | | TYR | |
| 20 | | GLN | |
| 21 | | ARG | |
| 22 | | PHE | |
| 23 | | SER | |
| 24 | | GLU | |
| 25 | | THR | |
| 26 | | SER | |
| 27 | | HIS | |
| 28 | | LEU | |
| 29 | | ARG | |
| 30 | | (GLY)* | |
| 31 | | GLN | |
| 32 | | TYR | |
| 33 | | ALA | |
| 34 | | PRO | |
| 35 | | PHE | |
| 36 | | PHE | |
| 37 | | (ASP) | |
| 38 | | LEU | |
| 39 | | ALA | |

FIG. 1A

PEPTIDE AMINOACID SEQUENCES

| Position | A | B | C | D | E |
|---|---|---|---|---|---|
| 01 | GLN | (TRP)* | MET | ALA | VAL |
| 02 | ----** | SER | MET | SER | VAL |
| 03 | GLN | PHE | GLN | SER | ASP |
| 04 | ALA | ASP | CYS | ALA | --- |
| 05 | GLU | THR | GLN | GLU | ARG |
| 06 | GLN | ILE | ALA | LYS | PHE |
| 07 | GLU | SER | GLU | GLY | PRO |
| 08 | PRO | THR | GLN | TYR | TYR |
| 09 | LEU | SER | GLU | ASP | THR |
| 10 | VAL | THR | PRO | LEU | GLY |
| 11 | (ARG) | VAL | LEU | VAL | --- |
| 12 | VAL | ASP | VAL | VAL | ALA |
| 13 | LEU | THR | ARG | | |
| 14 | VAL | LYS | VAL | | |
| 15 | ASN | LEU | LEU | | |
| 16 | (ASP) | SER | VAL | | |
| 17 | (ARG) | PRO | ASN | | |
| 18 | (VAL) | PHE | ASP | | |
| 19 | VAL | (CYS) | ARG | | |
| 20 | PRO | (ASP) | | | |
| 21 | | LEU | | | |
| 22 | | PHE | | | |
| 23 | | THR | | | |

FIG. 1B

N-TERMINUS 100KD PROTEIN

Position
- 01     VAL
- 02     VAL
- 03     ASP
- 04     GLU
- 05     ARG
- 06     PHE
- 07     PRO
- 08     TYR
- 09     THR
- 10     GLY

FIG. 1C

```
                          1   2   3   4   5   6   7   8   9   10  11  12  13  14  15  16  17  18  19  20
Peptide C: Leu-Ala-Val-Pro-Ala-Ser-Arg-Asn-Gln-Ser-Ser-Gly-Asp-Thr-Val-Asp
Peptide B:                    Ala-Ser-*-*-*-Gln-Ser-Ser-*-Asp-Thr-Val-Asp-Gln-Gly-Tyr-Gln-
Peptide A:                                        *-Gln-Ser-Ser-*-Asp-Thr-Val-Asp-Gln Possible
codons:5' CTG-GCG-GTG-CCG-GCG-TCG-CGG-AAT-CAA-TCG-TCG-GGG-GAT-ACG-GTG-GAT-CAA-GGG-TAT-CAA-
            A   A   A   A   A   A   C   G   A   A   A   A   C   A   C   A   C   A   C   G
            T   T   T   T   T   T       T                   T   T   T   T   T       T
            C   C   C   C   C   C       C                   C   C   C   C   C       C
                                        AGT AGA             AGT AGT
            TTA                         C   G               C   C
            G

AB1024:   3'-CGG-CAG-GGG-CGG-CGG-TCG-GCG-TTG-GTC-TCG-TCG-CCG-CTG-TGG-CAG-CTG-GTC

AB1065:                       3'-CCG-CTG-TGG-CAC-CTG-GTC
                                                      A

AB1066:                                               G
AB1067:                                       A
AB1068:                                   A
AB1069:                               A   A       A
AB1070:                               A   A   A   G   A

AB1226:                                                                   3'-CAG-CTG-GTC-CCG-GTG-CCG-ATG-GTC
                                                                                      C   A           A

AB1227:                                                                   3'-CAG-CTG-GTC-CCG-GTG-CCG-ATG-GTC
                                                                                      C       A   T   A   T
                                                                                              A

AB1298:                                                                   3'-CTG-TGG-CAG-CTG-GTG-CCG-ATG-GTC
                                                                                      A   C   C   A   T
```

FIG.2A-1

(phytase N-terminus, continued)

```
              21  22  23  24  25  26  27  28  29  30  31  32  33  34  35  36  37  38  39
Peptide B:  (Arg)-Phe-Ser-Glu-Thr-Ser-His-Leu-Arg-(Gly)-Gln-Tyr-Ala-Pro-Phe-Phe-(Asp)-Leu-Ala
             CGG-TTT-TCG-GAG-ACG-TCG-CAT-CTG-CGG- GGG-CAG-TAT-CGC-CCG-TTT- TTT- GAT- CTG-GCG
              T   A   C   A   A   A   A   C   A         A   C   A   C   C   C   A   A
              T   T   T   T   T   T   T   T   T         T   T   T   T   T   T   C   T   T
              C   C   C   C   C   C   C   C   C         C   C   C   C   C   C       C   C
             AGG AGT     AGT         AGT TTG AGG                                    TTG
              A   C       C           C   A   A                                     A AB1388:                                              3'-CCG-GTC- ATG-CGG-GGG- AAG- AAG-  CTG-  GA
                                                                 C                           A
```

FIG.2A-2

```
                    1   2   3   4   5   6   7   8   9  10  11          12  13  14  15
Peptide A: (Gln– ? –Gln–Ala–Glu–Gln–Glu–Pro–Leu–Val–(Ser/Arg)–Val–Leu–Val–(Asp/Asn)

CAG–???–CAG–GCG–GAG–CAG–GAG–CCG–CTG–GTG–(TCG/CGG)–GTG–CTG–GTG–(GAT/AAT)
            A       A   A   A   A   A   A   A   A              A   A   A   A   C   C
                            T               T   T   T          T   T   T   T   C
                            C               C   C   C          C   C   C   C
                                                    TTG   AGT  AGG               TTG
                                                     A     C                      A

AB1295:   3'–GTC.CGC.CTC.GTC.CTC.GGG.GAG.CA–5'
              T   G T T T T    C A C 16    17      18  19     20    21  22
          –Asp/Thr/Arg–(Arg/Val)–Val–Pro–(Pro)–Met–Gly

–GAT/ACG/CGG–(CGG/GTG)–GTG–CCG–(CCG)–ATG–GGG
           C    A      A   A     A   A   A     A
           T    T      T   T     T   T   T     T   C
           C    C      C   C     C   C   C     C
          AGG  AGG
           A    A

FIG.2B–1
```

```
                 1   2   3   4   5   6   7   8   9  10  11  12  13  14  15  16  17  18
Peptide B: (Trp)-Ser-Phe-Asp-Thr-Ile-Ser-Thr-Ser-Thr-Val-Asp-Thr-Lys-Leu-Ser-Pro-Phe- (TGG)-TCG-TTT-GAT-ACG-ATA-TCG-ACG-TCG-ACG-GTG-GAT-ACG-AAG-CTG-TCG-CCG-TTT-
                  A   C   A   T   A   A   A   A   C   A   A   A   A   A   A   A   C
                  T       T   C   T   T   T   T   T       T   T   T   T   T   T
                  C       C   C   C   C   C   C   C       C   C   C   C   C   C
                 AGT         AGT AGT                              TTG AGT
                  C           C   C                                   A   C AB1296:    3'-AAG.CTG.TGC.TAG.AGG.TGG.AGG.TGG.CAC.CTG.TGC.TTC-5'          AB1297:  3'-GGC.AAG.
                              TCC  C TCC  C                                            G 19  20  21  22  23  24  25  26  27  28  29  30  31   32  33
          (Cys)-(Asp)-Leu-Phe-Thr-(Thr)-(Asp)-(Glu)-(Cys)-(Ile)-(Thr/Asn)-(Tyr)-(Arg/Gly)-(Tyr)-Leu
           (GTG)-(GAT)- CTG- TTT- ACG-(ACG)-(GAT)- GAG)- (TGT)-(ATA)-(ACG/AAT) -(TAT)-(CGG/GGG)-(TAT)-CTG
            C   C   A   C   A   A   C   A   C   T   A   C   A   A   C   A
                    T   T                       C   T       C       T       C   T
                    C   C                                           C       C       C
                   TTG                                                      AGG     TTG
                    A                                                        A       A (ACG).(CTG).GAG. AAG.TGC.(TGC).(CTG). (CTC). (ACG).(TAG).(T)-5'
         C         G   G            FIG.2B-2
```

```
 1   2   3   4   5   6   7   8   9  10  11  12  13  14  15  16  17  18  19  20  21  22  23
Phe-Ser-Tyr-Gly-Ala-Ala-Ile-Pro-Gln-Ser-Thr-Gln-Glu-Lys-Gln-Phe-Ser-Gln-Glu-Phe-Arg-Asp-Gly

5'-TTT-TCG-TAT-GGG-GCG-GCG-ATA-CCG-CAG-TCG-ACG-CAG-GAG-AAG-CAG-TTT-TCG-CAG-GAG-TTT-CGG-GAT-GGG
       C   A   C   A   A   A   T   A   A   A   A   A   A   A   A   C   A   A   A   C   A   A
       T   T   T   T   T   C   T   T   T   T           T           T       T   T       C   T
       C   C   C   C   C   C   C               C   C                   C       C       T   C
                   AGT                     AGT                     AGT                      AGG  C
                   C                       C                       C                        C

AB1025: 3'-ATG-CCG-CGG-CGG-TAG-GGG-GTC-TCG-TGG-GTC-CTC-TTC-GTC-CTC-TTC-GTC-AAG-TCG-GTC-CTC-AAG-GC-5'
AB1026:                                                       T           AGA    T
                                                                                 C
AB1027: 3'-ATG-CCG-GCG-CGC-TAA-GGC-GTC-5'                                 3'-GTC-CTC-TTC-GTC-AAG-TCG-GTC-CTC-CTC-AAG-GC-5'
           A   T   T   G
           A   A
           G   G
```

FIG.3

```
GTCGACTTCCCGTCCTATTCGGCCTCGTCCGCTGAAGATCCATCCCACCA
SalI
TTGCACGTGGGCCACCTTTGTGAGCTTCTAACCTGAACTGGTAGAGTATC      100

ACACACCATGCCAAGGTGGGATGAAGGGGTTATATGAGACCGTCCGGTCC

GGCGCGATGGCCGTAGCTGCCACTCGCTGCTGTGCAAGAAATTACTTCTC      200

ATAGGCATCATGGGCGTCTCTGCTGTTCTACTTCCTTTGTATCTCCTGTC
         translation start
TGGGTATGCTAAGCACCACAATCAAAGTCTAATAAGGACCCTCCCTTCCG      300
   start<-------------------------------------------
AGGGCCCCTGAAGCTCGGACTGTGTGGGACTACTGATCGCTGACTATCTG
--intron-------------------------------------------
TGCAGAGTCACCTCCGGACTGGCAGTCCCCGCCTCGAGAAATCAATCCAG      400
->end
TTGCGATACGGTCGATCAGGGGTATCAATGCTTCTCCGAGACTTCGCATC

TTTGGGGTCAATACGCACCGTTCTTCTCTCTGGCAAACGAATCGGTCATC      500

TCCCCTGAGGTGCCCGCCGGATGCAGAGTCACTTTCGCTCAGGTCCTCTC

CCGTCATGGAGCGCGGTATCCGACCGACTCCAAGGGCAAGAAATACTCCG      600

CTCTCATTGAGGAGATCCAGCAGAACGCGACCACCTTTGACGGAAAATAT

GCCTTCCTGAAGACATACAACTACAGCTTGGGTGCAGATGACCTGACTCC      700

CTTCGGAGAACAGGAGCTAGTCAACTCCGGCATCAAGTTCTACCAGCGGT

ACGAATCGCTCACAAGGAACATCGTTCCATTCATCCGATCCTCTGGCTCC      800

AGCCGCGTGATCGCCTCCGGCAAGAAATTCATCGAGGGCTTCCAGAGCAC

CAAGCTGAAGGATCCTCGTGCCCAGCCCGGCCAATCGTCGCCCAAGATCG      900
         BamHI
ACGTGGTCATTTCCGAGGCCAGCTCATCCAACAACACTCTCGACCCAGGC

ACCTGCACTGTCTTCGAAGACAGCGAATTGGCCGATACCGTCGAAGCCAA      1000
```

FIG.6A

```
TTTCACCGCCACGTTCGTCCCCTCCATTCGTCAACGTCTGGAGAACGACC

TGTCCGGTGTGACTCTCACAGACACAGAAGTGACCTACCTCATGGACATG  1100

TGCTCCTTCGACACCATCTCCACCAGCACCGTCGACACCAAGCTGTCCCC
                                SalI
CTTCTGTGACCTGTTCACCCATGACGAATGGATCAACTACGACTACCTCC  1200

AGTCCTTGAAAAAGTATTACGGCCATGGTGCAGGTAACCCGCTCGGCCCG

ACCCAGGGCGTCGGCTACGCTAACGAGCTCATCGCCCGTCTGACCCACTC  1300

GCCTGTCCACGATGACACCAGTTCCAACCACACTTTGGACTCGAGCCCGG

CTACCTTTCCGCTCAACTCTACTCTCTACGCGGACTTTTCGCATGACAAC  1400

GGCATCATCTCCATTCTCTTTGCTTTAGGTCTGTACAACGGCACTAAGCC

GCTATCTACCACGACCGTGGAGAATATCACCCAGACAGATGGATTCTCGT  1500

CTGCTTGGACGGTTCCGTTTGCTTCGCGTTTGTACGTCGAGATGATGCAG

TGTCAGGCGGAGCAGGAGCCGCTGGTCCGTGTCTTGGTTAATGATCGCGT  1600

TGTCCCGCTGCATGGGTGTCCGGTTGATGCTTTGGGGAGATGTACCCGGG

ATAGCTTTGTGAGGGGGTTGAGCTTTGCTAGATCTGGGGGTGATTGGGCG  1700

GAGTGTTTTGCTTAGCTGAATTACCTTGATGAATGGTATGTATCACATTG
translation stop
CATATCATTAGCACTTCAGGTATGTATTATCGAAGATGTATATCGAAAGG  1800

ATCAATGGTGACTGTCACTGGTTATCTGAATATCCCTCTATACCTCGTCC

CACAACCAATCATCACCCTTTAAACAATCACACTCAACGCACAGCGTACA  1900

AACGAACAAACGCACAAAGAATATTTTACACTCCTCCCCAACGCAATACC

AACCGCAATTCATCATACCTCATATAAATACAATACAATACAATACATCC  2000
```

FIG.6B

```
ATCCCTACCCTCAAGTCCACCCATCCTATAATCAATCCCTACTTACTTAC

TTCTCCCCCTCCCCCTCACCCTTCCCAGAACTCACCCCCGAAGTAGTAAT  2100

AGTAGTAGTAGAAGAAGCAGACGACCTCTCCACCAATCTCTTCGGCCTCT

TATCCCCATACGCTACACAAAACCCCCACCCCGTTAGCATGCACTCAGAA  2200

AATAATCAAAAATAACTAAGAAGGAAAAAAAAGAAGAAGAAAGGTTACAT

ACTCCTCTCATACAAACTCCAAGACGTATACATCAAGATGGGCAATCCCA  2300

CCATTACTGATATCCATCTATGAACCCATTCCCATCCCACGTTAGTTGAT

TACTTTACTTAGAAGAAGAAAAAGGGAAGGGAAGGGAAAGAAGTGGATGG  2400

GATTGAGTTAGTGCTCACCGTCTCGCAGCAAGTTTATATTCTTTTGTTTG

GCGGATATCTTTCACTGCTCCTGCTGGACGTTGTCACGGGGTGGTAGTGG  2500

TTGGCGGTGGTGAGGGTCCATGATCACTCTTGGTTTGGGGGGTTGTTGTT

GTCGTTGTTGTTGTTGGGTGGGCATTTTCTTTTCTTCACTTGGGGAT  2600

TATTATTTGGAATTGGTTAGTTTGAGTGAGTGGGTAATATTGAATGGGTG

ATTATTGGGAATGAAGTAGATTTGGCTATGAATGGTTGATGGGATGGAAT  2700

GAATGGATGGATGAATAGATGGAGGCGGAAAAGTCAGGTGGTTTGAGGTT

CGGATTATTATCTTTGTGCCTGAGGCATCACTCTCCATCTATGTTGTTCT  2800

TTCTATACCGATCTACCAGAGCTAAGTTGACTGATTCTACCACAGTGCAC

AATAAGTATGTACTTATTTCATTTAGAGTATTTAGATTAACCCGCTGTGC  2900

TATTTGCCGTAGCTTTCCACCCAATTTCGAAGTTCGAAGAATTAAAACTC

ATCCTACAGTACAGAATAGAAGTAAAAGGAGAAGAGAAAAACAAGATAAT  3000
```

FIG.6C

```
ACAACCAGTCCAGGTCCATTCTAGATCTCGAATGACCACCAAATAAGAAA

GCAACAAGCAAGTAAGCAAAGCATAAGTCTAAATGAACGCCAATAACTTC    3100

ATCGCCTGCCTTTGAAACTGAACGCTATGCACGAATGGCTCGAAATGATT

CCCTTAACTCCGTAGTATTGAGAGTGAGAGGAAAAGAAAAAAAGAGACAG    3200

AAAAGCTGACCATGGGAAAGAAGCATGATCAGTCGGGAATGGATCTGCGG

GTTGAGATAGATATGAGTTGCCTCGCAGATCCGGTGACAAGATAAGAGAA    3300

TTGGGAGATGTGATCAGCCACTGTAACTTCATCAAGCATCGACATTCAAC

CGTCGGGTCTGCGGGTTGAGATGCAAGTTGAGATGCCACGCAGACCCGAA    3400

CAGAGTGAGAGATGTGAGACTTTTGAACCACTGTGACTTCATCAAGCATC

AAAACACACTCCATGGTCAATCGGTTAGGGTGTGAGGGTTGATATGCCAG    3500

GTTCGATGCCACGCAGACCCGAACCGACTGAGAAATATGAAAAGTTGGAC

AGCCACTTCATCTTCATCAAGCGTAAAACCCCAATCAATGGTAAATCGAA    3600

AACGAATCTGCGGGCTGATGTGGAAATGAGACGAATGCCTCGCAGATTCG

AAGACACGTAAATCGAGATGAACAATCACTTTAACTTCATCAAAGCCTTA    3700

AATCACCCAATGGCCAGTCTATTCGGGTCTGCGGGTTGAGGTTCCTGTTG

AGATGCCACGCAGACTGCGAACATGCGATGCATTATAAGTTGGACGAGTG    3800

TAGACTGACCATTGATAACCGAGATAAACAATCACTTCAACTTCATCAAA

GCCTTAAATCACTCAATGGCCAGTCTGTTTGCGGTCTGCGGGCTGATACC    3900

CAAGTTGCGATGCCACGCAGACTGCAAACATTGATCGAGAGACGAGAAAA

ACAACGCACTTTAACTTCAACAAAAGCCTTTCAATCAGTCAATGGCCAGT    4000
```

FIG.6D

```
CTGTTCGCGGTCTGCGGGCTGATATGCGAGTTGAGGTGCCTCGCAGACCG

CGAACATGCGATGTAATTTCTTAGTTAGACGAGTGCCTGGCCATTGAGAA    4100

ACGAGAGAAACAACCACTTTAACTTCATGAAAGCCTTGAACTACTCAATG

ACCCGTCTGTTGGCGGTCTGCGGGCTGATATTCGAGTTGAGATGCCACGC    4200

AGACCGCCAACATGCGATGTATCATGTAAGTTAGATGAGTGACTGGCCAT

TGAGAAACGAGAGAAACAACCACACTTCATGAGAGCCTTAAATTATTCAA    4300

TGACCAGTCTGTTCACGGTCTGCGGGTTGGTATGCGAGTCGAGGTGCCTC

GCAGACCGCGAACATGCGATGTTTTCGATGGACGAGTGAAGCCTGACGAT    4400

CGAGAACTATCTCAGTTGGGTTGGCCATTCGGCTGGCCGTTGGGTTTAGT

ATTAGGATCGTCAGGTTTGTCCGATGGAACGTTCCGTTTGCGTGCGTTGG    4500

CGCGACGAGCCCTCTCCTCGGCGTGATTCTGAAATTCTGCAATCAGGGCA

GCCGCAGCACGGCGACGGGACGTCCTCCAGGAGCTGTGTTGAAGTTTCGG    4600

GGTGGCGGTCCAGAAGGGGGAGTTACATTAAAAGCCTCATAGATGTCTTT

GGGTGGTTCCGGGGGGCCCATCGCAAGATCTTCTGGAGTTGTGCGTCTGA    4700

TCATCTCTTGAGTGTAATTGCGACGCAGACCGAGCTTCAGGATTTTGGAA

GGGCTGGATCGCTCCTGCTGACTCTTTCCCTCAGCGGGCTTCGTCTCGGC    4800

AGTCTTCATTTCGGCGGGCTGATCTTCCATCTCAGAATGGGATCGCTTTC

TGGTCGCTGCACCCGCTCCTCCCTTCAAGGTCAGCTTGATGCGCAGCGTC    4900

TTGGGCGGCTCAGCTGGTGGAGTTGGTTCCGGCTCTGGCTCCCTCCGGCG

TCGCTTGGGCACTTGAGTAGTCTCTGAGGCTTCGCCGCGGCGCCGTTTGC    5000
```

FIG.6E

```
              GAGTCGGCTCCTTGGTCTCTTTGGCCTCTTTCACTTCACCTGGACCGTCT

TTCGGGGCGGTTTCATCGTGCTGAGCGATCAAGGTTTGGATGTAGGCAGC   5100

CGGCATCATTCGATCAACGGCAATTCCTCTCTTGCGGGCCTCCTCCCGAG

CCTTGATTGTCGCCTTGACCTCGTCCACGTTTTCGAAGAAGAAAGGCATC   5200

TTGTTATCCTGAGGCAAGTTGCGCTCTCCCATGCGTGGGGATATCCGAAG

ATGCGGTCCTTCTCGAACTGTTCATGAGACTTCAGACGAATTGGAGGCTG   5300

GGGGAGCAATTTGTCTCCGTAGGTGTTGTTAGGGCGGAACCAAGAATAGC

CTTCGCCTACAACGACAAGCTCTTCGCCAAATTTATTTTTTTGGCCTGTA   5400

AAAACGAACCCATCCTCGTCAGTCCACCGGTGCGTCTCGGACGTAGAGAT

TGGCTTACTTATTCCCTCAACGCCGATCTCTGCCTGGGGCTGCGCTTCGG   5500

ATGCGGCCTCGGTCACGGCTCCGCCTCGGACTGCACCGCTGGAGTTTCGG

TCTTCTTCTCCTGCTTCTCCAGGTACTCCTTGCGTAACTCTTCGATCAGC   5600

CTCGGCTTCCGATGACTGCTCAAATTCTGGAGCAACAGCTGCCGCGGCCA

GGTCAAGCAGGCGGTTTGCTAAAACTGCCCATTTTCCATCGACACCTGCC   5700

TCCGACGCCTGTGCAAAACCAGCTGTTTTCGCATTGGCCTGTTTGTTGGC

ACGCGTCTTCTTGACTGCTGCCTTGCCCTTTACTTCCTTGAGAGCAGACT   5800

CTGGCTTAGATGATGGTGCACGGTTTCTGCGGAAGCGCCGCTCAGATTCC

AAAGATTCCATAGCTTTAATGGTAGGCTTTCTGGTTCTTCCAGAAGTGCG   5900

CGCAGCTGACGTAGTGGTTGAGTAGCTGGCAGTTGGGGATCCTGGGCCCT

CATTGGAACCATCAAGACCAAATTTGTTTCCATACATATCAGCATGGTAT   6000
```

FIG.6F

```
TCAAAAGGAAAACTTTCGCCGTACGGAGTACTGCGTTCGATTCCGGGTGT

ATCCAAGTCGTATCCAGACATGGTGTCGAATTCAGCCTTGCTGTCAAGAG    6100

CAGGGGTACTTTCAATGCTGTCAGCAACCACGCGGCCAAAGGGCGTCTTC

GGGAAAGAAGGTGTTTCAAGAGAAGCGTCATCCACGGCCTGGCTTGCGGC    6200

GTTGATTGCAGACTTTCGAGTAGATCGCTGAGGTCGCGAACTGGTTCGAG

TAGCAACCTGTGAATTGGCAGCCTTGTGACTGCTTCGATTCACTGCAGAG    6300

ACGGAGTAGACTGCACTGATTTGGAATTCTGAGTCGCAGCCATTCTGGAT

TTGCGTTCGGCGCGACGAGATCTCGCAGTCGTGGTACGAGGAGTAGAGCG    6400

AGGCTGCGTAGCAGTGTTGCAAGCTTGGTGCTAGCCTCCTGGGCTTCAGC

AGCTTCAGCAGTGGTGGCAGACGCAGCAGAATTAGCGGAGCTTTATCGGC    6500

TTTGCCGCTCTGAGCGTTGGGAGTAGAAGTGAGAGAAGAGGTAGAGTCCA

CGGAAGAAGTCTTCTCGCTGTTCTCAAAGCCGTTCAGCTTTGCTGGCATA    6600

GACTTACGCGTCTTGCGGCTGTTGGAAGCGGAAGAGTTCATGGCGGGAGA

GGAGACGTTAGAAGTAGACATGGTGGGTTTGTTGACGGGTTTTGAGTAA    6700

CAAGAGACTTGCGTCGATCTTTGAGTGTTCTTGACAGAAAGTTATGCAAC

GTCGAC    6756
SalI
```

FIG.6G

```
ATGGGCGTCTCTGCTGTTCTACTTCCTTTGTATCTCCTGTCTGGAGTCAC
 M  G  V  S  A  V  L  L  P  L  Y  L  L  S  G  V  T
-23      -20             ,              -10

CTCCGGACTGGCAGTCCCCGCCTCGAGAAATCAATCCAGTTGCGATACGG      100
    S  G  L  A  V  P  A  S  R  N  Q  S  S  C  D  T
    ,              -1 +1           ,              10

TCGATCAGGGGTATCAATGCTTCTCCGAGACTTCGCATCTTTGGGGTCAA
 V  D  Q  G  Y  Q  C  F  S  E  T  S  H  L  W  G  Q
          ,                    20              ,

TACGCACCGTTCTTCTCTCTGGCAAACGAATCGGTCATCTCCCCTGAGGT      200
 Y  A  P  F  F  S  L  A  N  E  S  V  I  S  P  E  V
       30              ,              40

GCCCGCCGGATGCAGAGTCACTTTCGCTCAGGTCCTCTCCCGTCATGGAG
 P  A  G  C  R  V  T  F  A  Q  V  L  S  R  H  G
 ,              50             ,              60

CGCGGTATCCGACCGACTCCAAGGGCAAGAAATACTCCGCTCTCATTGAG      300
 A  R  Y  P  T  D  S  K  G  K  K  Y  S  A  L  I  E
          ,                    70              ,

GAGATCCAGCAGAACGCGACCACCTTTGACGGAAAATATGCCTTCCTGAA
 E  I  Q  Q  N  A  T  T  F  D  G  K  Y  A  F  L  K
       80              ,                    90

GACATACAACTACAGCTTGGGTGCAGATGACCTGACTCCCTTCGGAGAAC      400
   T  Y  N  Y  S  L  G  A  D  D  L  T  P  F  G  E
   ,                   100             ,             110

AGGAGCTAGTCAACTCCGGCATCAAGTTCTACCAGCGGTACGAATCGCTC
 Q  E  L  V  N  S  G  I  K  F  Y  Q  R  Y  E  S  L
          ,                   120              ,

ACAAGGAACATCGTTCCATTCATCCGATCCTCTGGCTCCAGCCGCGTGAT      500
 T  R  N  I  V  P  F  I  R  S  S  G  S  S  R  V  I
      130              ,                   140

CGCCTCCGGCAAGAAATTCATCGAGGGCTTCCAGAGCACCAAGCTGAAGG
  A  S  G  K  K  F  I  E  G  F  Q  S  T  K  L  K
  ,                   150             ,              160

ATCCTCGTGCCCAGCCCGGCCAATCGTCGCCCAAGATCGACGTGGTCATT      600
 D  P  R  A  Q  P  G  Q  S  P  K  I  D  V  V  I
          ,                   170              ,

TCCGAGGCCAGCTCATCCAACAACACTCTCGACCCAGGCACCTGCACTGT
  S  E  A  S  S  S  N  N  T  L  D  P  G  T  C  T  V
      180              ,                   190

CTTCGAAGACAGCGAATTGGCCGATACCGTCGAAGCCAATTTCACCGCCA      700
   F  E  D  S  E  L  A  D  T  V  E  A  N  F  T  A
   ,                   200             ,              210
```

FIG.8A

```
CGTTCGTCCCCTCCATTCGTCAACGTCTGGAGAACGACCTGTCCGGTGTG
 T  F  V  P  S  I  R  Q  R  L  E  N  D  L  S  G  V
                       220

ACTCTCACAGACACAGAAGTGACCTACCTCATGGACATGTGCTCCTTCGA      800
 T  L  T  D  T  E  V  T  Y  L  M  D  M  C  S  F  D
       230                        240

CACCATCTCCACCAGCACCGTCGACACCAAGCTGTCCCCCTTCTGTGACC
    I  S  T  S  T  V  D  T  K  L  S  P  F  C  D
              250                        260

TGTTCACCCATGACGAATGGATCAACTACGACTACCTCCAGTCCTTGAAA      900
 L  F  T  H  D  E  W  I  N  Y  D  Y  L  Q  S  L  K
                       270

AAGTATTACGGCCATGGTGCAGGTAACCCGCTCGGCCCGACCCAGGGCGT
 K  Y  Y  G  H  G  A  G  N  P  L  G  P  T  Q  G  V
       280                        290

CGGCTACGCTAACGAGCTCATCGCCCGTCTGACCCACTCGCCTGTCCACG     1000
    G  Y  A  N  E  L  I  A  R  L  T  H  S  P  V  H
              300                        310

ATGACACCAGTTCCAACCACACTTTGGACTCGAGCCCGGCTACCTTTCCG
 D  D  T  S  S  N  H  T  L  D  S  S  P  A  T  F  P
                       320

CTCAACTCTACTCTCTACGCGGACTTTTCGCATGACAACGGCATCATCTC     1100
 L  N  S  T  L  Y  A  D  F  S  H  D  N  G  I  I  S
       330                        340

CATTCTCTTTGCTTTAGGTCTGTACAACGGCACTAAGCCGCTATCTACCA
    I  L  F  A  L  G  L  Y  N  G  T  K  P  L  S  T
              350                        360

CGACCGTGGAGAATATCACCCAGACAGATGGATTCTCGTCTGCTTGGACG     1200
 T  T  V  E  N  I  T  Q  T  D  G  F  S  S  A  W  T
                       370

GTTCCGTTTGCTTCGCGTTTGTACGTCGAGATGATGCAGTGTCAGGCGGA
 V  P  F  A  S  R  L  Y  V  E  M  M  Q  C  Q  A  E
       380                        390

GCAGGAGCCGCTGGTCCGTGTCTTGGTTAATGATCGCGTTGTCCCGCTGC     1300
    Q  E  P  L  V  R  V  L  V  N  D  R  V  V  P  L
              400                        410

ATGGGTGTCCGGTTGATGCTTTGGGGAGATGTACCCGGGATAGCTTTGTG
 H  G  C  P  V  D  A  L  G  R  C  T  R  D  S  F  V
                       420

AGGGGGTTGAGCTTTGCTAGATCTGGGGGTGATTGGGCGGAGTGTTTTGC     1400
 R  G  L  S  F  A  R  S  G  G  D  W  A  E  C  F  A
       430                        440

TTAG                                                   1404
```

CLONING AND EXPRESSION OF MICROBIAL PHYTASE

This application is a division of application Ser. No. 08/151,574 filed 12 Nov. 1993, now U.S. Pat. No. 5,436, 156, which is a continuation of application Ser. No. 041, 688,578, filed as PCT/NL90/00140 Sep. 27, 1990, now abandoned.

The present invention relates to the microbial production of phytase.

BACKGROUND OF THE INVENTION

Phosphorus is an essential element for the growth of all organisms. In livestock production, feed must be supplemented with inorganic phosphorus in order to obtain a good growth performance of monogastric animals (e.g. pigs, poultry and fish).

In contrast, no inorganic phosphate needs to be added to the feedstuffs of ruminant animals. Microorganisms, present in the rumen, produce enzymes which catalyze the conversion of phytate (myo-inositolhexakis-phosphate) to inositol and inorganic phosphate.

Phytate occurs as a storage phosphorus source in virtually all feed substances originating from plants (for a review see: *Phytic acid, chemistry and applications*, E. Graf (ed.), Pilatus Press; Minneapolis, Minn., U.S.A. (1986)). Phytate comprises 1–3 of all nuts, cereals, legumes, oil seeds, spores and pollen. Complex salts of phytic acid are termed phytin. Phytic acid is considered to be an anti-nutritional factor since it chelates minerals such as calcium, zinc, magnesium, iron and may also react with proteins, thereby decreasing the bioavailability of protein and nutritionally important minerals.

Phytate phosphorus passes through the gastro-intestinal tract of monogastric animals and is excreted in the manure. Though some hydrolysis of phytate does occur in the colon, the thus-released inorganic phosphorus has no nutritional value since inorganic phosphorus is absorbed only in the small intestine. As a consequence, a significant amount of the nutritionally important phosphorus is not used by monogastric animals, despite its presence in the feed.

The excretion of phytate phosphorus in manure has further consequences. Intensive livestock production has increased enormously during the past decades. Consequently, the amount of manure produced has increased correspondingly and has caused environmental problems in various parts of the world. This is due, in part, to the accumulation of phosphate from manure in surface waters which has caused eutrophication.

The enzymes produced by microorganisms, that catalyze the conversion of phytate to inositol and inorganic phosphorus are broadly known as phytases. Phytase producing microorganisms comprise bacteria such as *Bacillus subtilis* (V. K. Paver and V. J. Jagannathan (1982) J. Bacteriol. 151, 1102–1108) and Pseudonomas (D. J. Cosgrove (1970) Austral. J. Biol. Sci. 23, 1207–1220); yeasts such as *Saccharomyces cerevisiae* (N. R. Nayini and P. Markakis (1984) Lebensmittel Wissenschaft und Technologie 17, 24–26); and fungi such as *Aspergillus terreus* (K. Yamada, Y. Minoda and S. Yamamoto (1986) Agric. Biol. Chem. 32, 1275–1282). Various other Aspergillus species are known to produce phytase, of which, the phytase produced by *Aspergillus ficuum* has been determined to possess one of the highest levels of specific activity, as well as having better thermostability than phytases produced by other microorganisms (unpublished observations).

The concept of adding microbial phytase to the feedstuffs of monogastric animals has been previously described (Ware, J. H., Bluff, L. and Shieh, T. R. (1967) U.S. Pat. No. 3,297,548; Nelson, T. S., Shieh, T. R., Wodzinski, R. J. and Ware, J. H. (1971) J. Nutrition 101, 1289–1294). To date, however, application of this concept has not been commercially feasible, due to the high cost of the production of the microbial enzymes (Y. W. Han (1989) Animal Feed Sci. & Technol. 24, 345–350). For economic reasons, inorganic phosphorus is still added to monogastric animal feedstuffs.

Microbial phytases have found other industrial uses as well. Exemplary of such utilities is an industrial process for the production of starch from cereals such as corn and wheat. Waste products comprising e.g. corn gluten feeds from such a wet milling process are sold as animal feed. During the steeping process phytase may be supplemented. Conditions ($T \approx 50°$ C. and pH=5.5) are ideal for fungal phytases (see e.g. European Patent Application 0 321 004 to Alko Ltd.). Advantageously, animal feeds derived from the waste products of this process will contain phosphate instead of phytate.

It has also been conceived that phytases may be used in soy processing (see Finase™ Enzymes By Alko, a product information brochure published by Alko Ltd., Rajamäki, Finland). Soybean meal contains high levels of the anti-nutritional factor phytate which renders this protein source unsuitable for application in baby food and feed for fish, calves and other non-ruminants. Enzymatic upgrading of this valuable protein source improves the nutritional and commercial value of this material.

Other researchers have become interested in better characterizing various phytases and improving procedures for the production and use of these phytases. Ullah has published a procedure for the purification of phytase from wild-type *Aspergillus ficuum*, as well as having determined several biochemical parameters of the product obtained by this purification procedure (Ullah, A. (1988a) Preparative Biochem. 18, 443–458). Pertinent data obtained by Ullah is presented in Table 1, below.

The amino acid sequence of the N-terminus of the *A. ficuum* phytase protein has twice been disclosed by Ullah: Ullah, A. (1987) Enzyme and Engineering conference IX, Oct. 4–8, 1987, Santa Barbara, Calif. (poster presentation); and Ullah, A. (1988b) Prep. Biochem. 18, 459–471. The amino acid sequence data obtained by Ullah is reproduced in FIG. 1A, sequence E, below.

Several interesting observations may be made from the disclosures of Ullah. First of all, the "purified" preparation described in Ullah (1988a and 1988b) consists of two protein bands on SDS-PAGE. We have found, however, that phytase purified from *A. ficuum* contains a contaminant and that one of the bands found on SDS-PAGE, identified by Ullah as a phytase, is originating from this contaminant.

This difference is also apparent from the amino acid sequencing data published by Ullah (1987, 1988b; compare FIG. 1A, sequences A and B with sequence C). We have determined, in fact, that one of the amino acid sequences of internal peptides of phytase described by Ullah (see FIG. 1B, sequence E) actually belongs to the contaminating 100 kDa protein (FIG. 1C) which is present in the preparation obtained via the procedure as described by Ullah, and seen as one of the two bands on SDS-PAGE (Ullah, 1988a and 1988b). Ullah does not recognize the presence of such a contaminating protein, and instead identifies it as another form of phytase. The presence of such contamination, in turn, increases the difficulty in selecting and isolating the actual nucleotide sequence encoding phytase activity. Furthermore, the presence of the contamination lowers the specific activity value of the protein tested.

Further regarding the sequence published by Ullah, it should be noted that the amino acid residue at position 12, has been disclosed by Ullah to be glycine. We have consistently found using protein and DNA sequencing techniques, that this residue is not a glycine but is in fact a cysteine (see FIGS. 6 and 8).

Finally, Ullah discloses that phytase is an 85 kDa protein, with a molecular weight after deglycosylation of 61.7 kDa (Ullah, 1988b). This number, which is much lower than the earlier reported 76 kDa protein (Ullah, A. and Gibson, D. (1988) Prep. Biochem. 17(1), 63–91) was based on the relative amount of carbohydrates released by hydrolysis, and the apparent molecular weight of the native protein on SDS-PAGE. We have found, however, that glycosylated phytase has a single apparent molecular weight of 85 kDa, while the deglycosylated protein has an apparent molecular weight in the range of 48–56.5 kDa, depending on the degree of deglycosylation.

Mullaney et al. (Filamentous Fungi Conference, April, 1987, Pacific Grove, Calif. (poster presentation) also disclose the characterization of phytase from *A. ficuum*. However, this report also contains mention of two protein bands on SDS-PAGE, one of 85 kDa, and one of 100 kDa, which were present in the "purified" protein preparation. These protein bands are both identified by the authors as being forms of phytase. A method for transforming microbial hosts is proposed, but has not been reported. The cloning and isolation of the DNA sequence encoding phytase has not been described.

It will be appreciated that an economical procedure for the production of phytase will be of significant benefit to, inter alia, the animal feed industry. One method of producing a more economical phytase would be to use recombinant DNA techniques to raise expression levels of the enzyme in various microorganisms known to produce high levels of expressed peptides or proteins. To date, however, the isolation and cloning of the DNA sequence encoding phytase activity has not been published.

SUMMARY OF THE INVENTION

The present invention provides a purified and isolated DNA sequence coding for phytase. The isolation and cloning of this phytase encoding DNA sequence has been achieved via the use of specific oligonucleotide probes which were developed especially for the present invention. Preferred DNA sequences encoding phytases are obtainable from fungal sources, especially filamentous fungi of the genus Aspergillus.

It is another object of the present invention to provide a vector containing an expression construct which further contains at least one copy of at least one, preferably homologous DNA sequence encoding phytase, operably linked to an appropriate regulatory region capable of directing the high level expression of peptides or proteins having phytase activity in a suitable expression host.

The expression construct provided by the present invention may be inserted into a vector, preferably a plasmid, which is capable of transforming a microbial host cell and integrating into the genome.

It is a further object of the present invention to provide a transformant, preferably, a microbial host which has been transformed by a vector as described in the preceding paragraph. The transformed hosts provided by the present invention are filamentous fungi of the genera Aspergillus, Trichoderma, Mucor and Penicillium, yeasts of the genera Kluyveromyces and Saccharomyces or bacteria of the genus Bacillus. Especially preferred expression hosts are filamentous fungi of the genus Aspergillus. The transformed hosts are capable of producing high levels of recombinant phytase on an economical, industrial scale.

In other aspects, the invention is directed to recombinant peptides and proteins having phytase activity in glycosylated or unglycosylated form; to a method for the production of said unglycosylated peptides and proteins; to peptides and proteins having phytase activity which are free of impurities; and to monoclonal antibodies reactive with these recombinant or purified proteins.

A comparison of the biochemical parameters of the purified wild-type *A. ficuum* phytase as obtained by Ullah, against the further purified wild-type *A. ficuum* phytase, obtained via the present invention, is found in Table 1, below. Of particular note is the specific activity data wherein it is shown that the purified protein which we have obtained has twice the specific activity of that which was published by Ullah.

The present invention further provides nucleotide sequences encoding proteins exhibiting phytase activity, as well as amino acid sequences of these proteins. The sequences provided may be used to design oligonucleotide probes which may in turn be used in hybridization screening studies for the identification of phytase genes from other species, especially microbial species, which may be subsequently isolated and cloned.

The sequences provided by the present invention may also be used as starting materials for the construction of "second generation" phytases. "Second generation" phytases are phytases, altered by mutagenesis techniques (e.g. site-directed mutagenesis), which have properties that differ from those of wild-type phytases or recombinant phytases such as those produced by the present invention. For example, the temperature or pH optimum, specific activity or substrate affinity may be altered so as to be better suited for application in a defined process.

Within the context of the present invention, the term phytase embraces a family of enzymes which catalyze reactions involving the removal of inorganic phosphorous from various myoinositol phosphates.

Phytase activity may be measured via a number of assays, the choice of which is not critical to the present invention. For purposes of illustration, phytase activity may be determined by measuring the amount of enzyme which liberates inorganic phosphorous from 1.5 mM sodium phytate at the rate of 1 $\mu$mol/min at 37° C. and at pH 5.50.

It should be noted that the term "phytase" as recited throughout the text of this specification is intended to encompass all peptides and proteins having phytase activity. This point is illustrated in FIG. 1A which compares sequences A and B (sequences which have been obtained during the course of the present work) with sequence C (published by Ullah, 1988b). The Figure demonstrates that proteins may be obtained via the present invention which lack the first four amino acids (the protein of sequence A lacks the first seven amino acids) of the mature *A. ficuum* phytase protein.

These proteins, however, retain phytase activity. The complete amino acid sequence of the phytase protein, as deduced from the corresponding nucleotide sequence, is shown in FIG. 8.

Phytases produced via the present invention may be applied to a variety of processes which require the conversion of phytate to inositol and inorganic phosphate.

For example, the production of phytases according to the present invention will reduce production costs of microbial phytases in order to allow its economical application in animal feed which eventually will lead to an in vivo price/performance ratio competitive with inorganic phosphate. As a further benefit, the phosphorus content of manure will be considerably decreased.

It will be appreciated that the application of phytases, available at a price competitive with inorganic phosphate, will increase the degrees of freedom for the compound feed industry to produce a high quality feed. For example, when feed is supplemented with phytase, the addition of inorganic phosphate may be omitted and the contents of various materials containing phytate may be increased.

In addition to use in animal feeds and soy processing as discussed above, the phytase obtained via the present invention may also be used in diverse industrial applications such as:

liquid feed for pigs and poultry. It has become common practice to soak feed for several hours prior to feeding. During this period the enzyme will be able to convert phytate to inositol and inorganic phosphate;

an industrial process for the production of inositol or inositol-phosphates from phytate;

other industrial processes using substrates that contain phytate such as the starch industry and in fermentation industries, such as the brewing industry. Chelation of metal ions by phytate may cause these minerals to be unavailable for the production microorganisms. Enzymatic hydrolysis of phytate prevents these problems.

These and other objects and advantages of the present invention will become apparent from the following detailed description.

BRIEF DESCRIPTION OF THE FIGURES

FIG. 1.

A. (SEQ ID NO:1), (SEQ ID NO:2), and (SEQ ID NO:6). N-terminal amino acid sequences as determined for purified phytase. The amino acid sequences labeled A and B are provided by the present invention, and originate from the phytase subforms with isoelectric points of 5.2 and 5.4, respectively. Sequence C is cited from Ullah (1987, 1988b, supra). The amino acid residue located at position 12 of sequences A and B has been determined by the present invention not to be a glycine residue. [* denotes no unambigous identification. ** denotes no residue detected.]

B. (SEQ ID NO:4), (SEQ ID NO:5), (SEQ ID NO:7), (SEQ ID NO:8), and (SEQ ID NO:9). N-terminal amino acid sequences of CNBr-cleaved internal phytase fragments. The amino acid sequences labeled A and B (apparent molecular weight approximately 2.5 kDa and 36 kDa peptides, respectively) are provided by the present invention. Sequences C through E are cited from Ullah (1988b, supra).

C. (SEQ ID NO:3) N-terminal amino acid sequence of a 100 kDa protein which has been found by the present invention to be present in crude phytase samples.

FIG. 2.

A. (SEQ ID NO:10), (SEQ ID NO:14), (SEQ ID NO:15), (SEQ ID NO:16), (SEQ ID NO:17), (SEQ ID NO:18), (SEQ ID NO:19), (SEQ ID NO:20), (SEQ ID NO:21), (SEQ ID NO:22), (SEQ ID NO:23), and (SEQ ID NO:24). Oligonucleotide probes designed on basis of the data from FIG. 1A, peptides A through E.

B. (SEQ ID NO:11), (SEQ ID NO:12), (SEQ ID NO:25), (SEQ ID NO:26), and (SEQ ID NO:27). Oligonucleotide probes designed on the basis of the data from FIG. 1B, peptides A and B.

FIG. 3. (SEQ ID NO:13), (SEQ ID NO:28), (SEQ ID NO:29), and (SEQ ID NO:30). Oligonucleotide probes used for the isolation of the gene encoding the acid-phosphatase.

Figure 4:
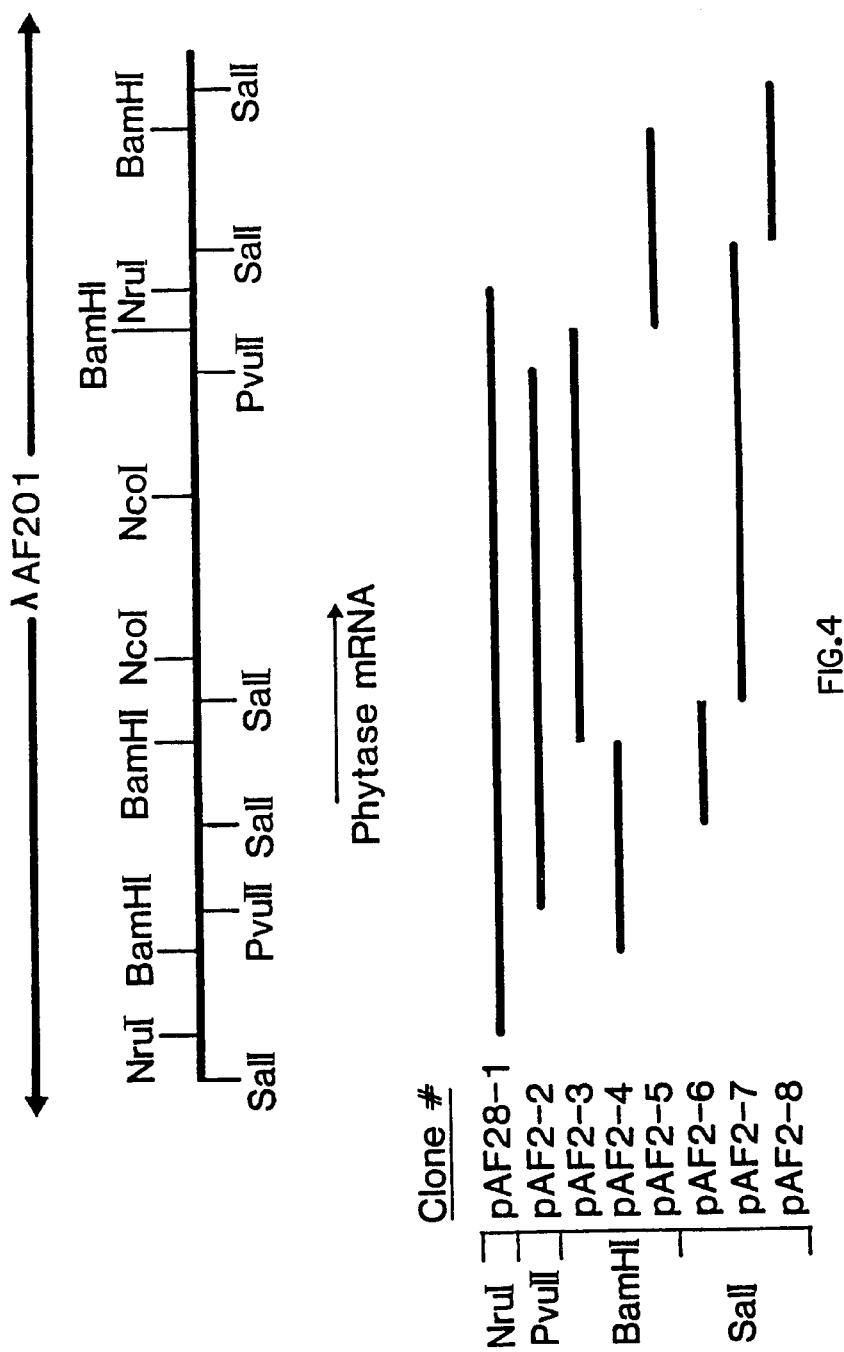

FIG. 4. Restriction map of bacteriophage lambda AF201 containing the phytase locus of *A. ficuum*. The arrow indicates the position of the phytase gene and the direction of transcription. Clone # shows the subclones derived with indicated restriction enzymes from phage AF201 in pAN 8-1 (for pAF 28-1) and in pUC19 (for all other subclones).

Figure 5:
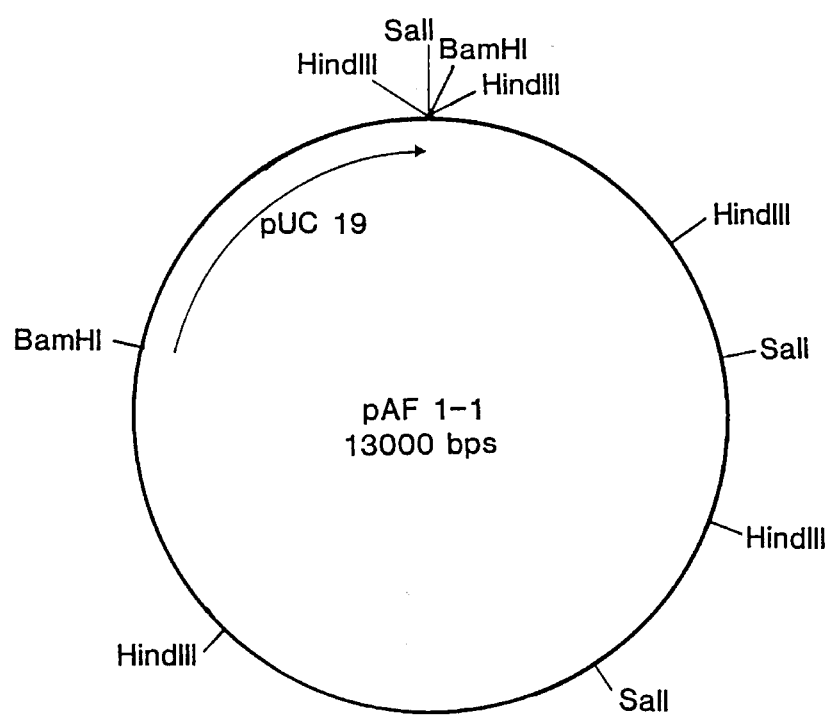

FIG. 5. Physical map of pAF 1-1. The 10 kb BamHI fragment, inserted in pUC19, contains the entire gene encoding acid phosphatase from *A. ficuum*.

FIG. 6. (SEQ ID NO:31) and (SEQ ID NO:32). Compilation of the nucleotide sequences of plasmids pAF 2-3, pAF 2-6, and pAF 2-7 encompassing the chromosomal phytase gene locus. The phytase coding region is located from nucleotide position 210 to position 1713; an intron is present in the chromosomal gene from nucleotide position 254 to position 355.

Relevant features such as restriction sites, the phytase start and stop codons, and the intron position are indicated.

Figure 7:
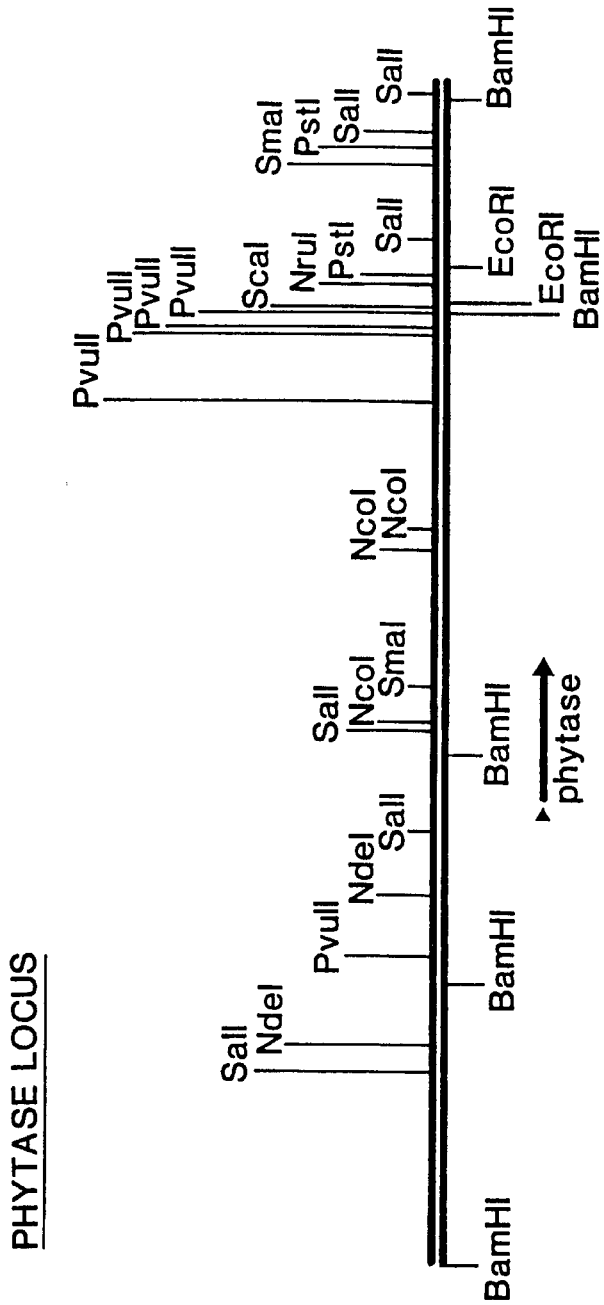

FIG. 7. Detailed physical map of the sequenced phytase chromosomal locus; the arrows indicate the location of the two exons of the phytase coding region.

FIG. 8. Nucleotide sequence of the translated region of the phytase cDNA fragment and the derived amino acid sequence of the phytase protein; the start of the mature phytase protein is indicated as position +1. The amino-terminus of the 36 kDa internal protein fragment is located at amino acid position 241, whereas the 2.5 kDa protein fragment starts at amino acid position 390.

Figure 9:
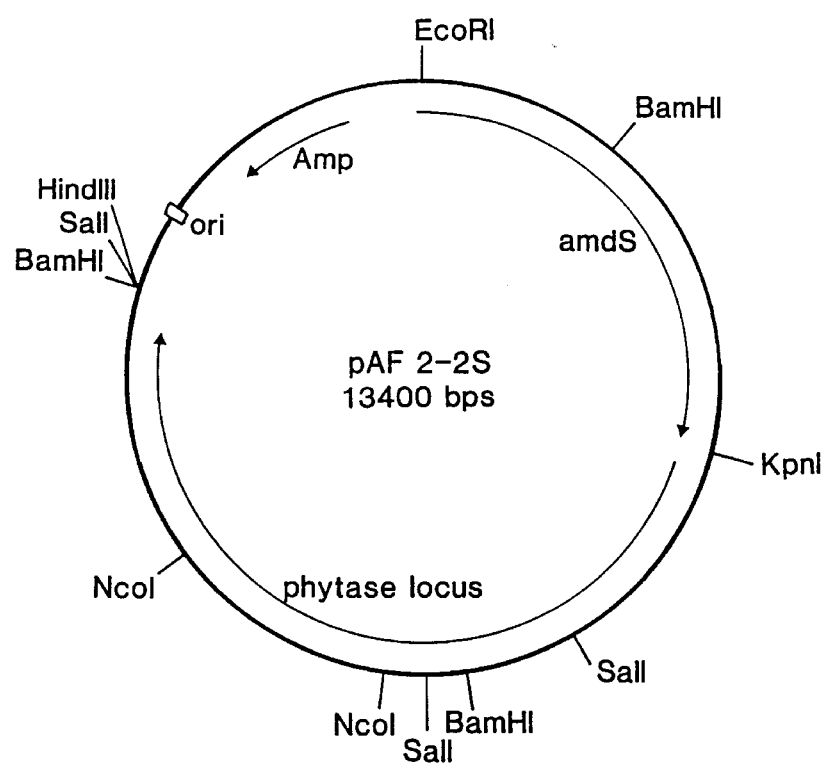

FIG. 9. Physical map of the phytase expression cassette pAF 2-2S. Arrows indicate the direction of transcription of the genes.

FIG. 10. IEF-PAGE evidence of the overexpression of phytase in an *A. ficuum* NRRL 3135 transformant. Equal volumes of culture supernatant of *A. ficuum* (lane 1) and transformant pAF 2-2S SP7 (lane 2), grown under identical conditions, were analysed on a Phast-System (Pharmacia) IEF-PAGE gel in the pH-range of 4.5–6. For comparison, a sample of *A. ficuum* phytase, purified to homogeneity was included either separately (lane 4), or mixed with a culture supernatant (lane 3). The gels were either stained with a phosphatase stain described in the text (A), or with a general protein stain (Coomassie Brilliant Blue, B). The phytase bands are indicated by an asterisk.

Figure 10A:
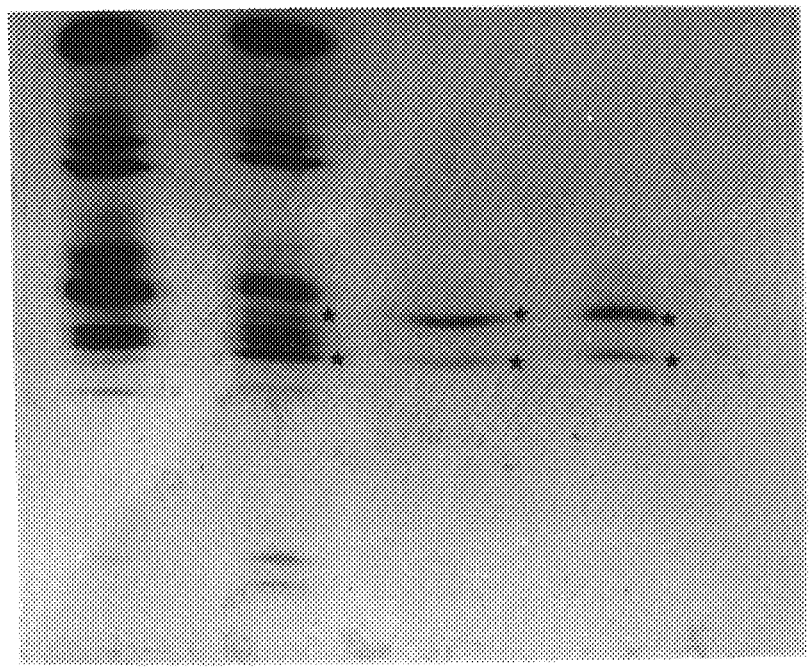
Figure 10B:
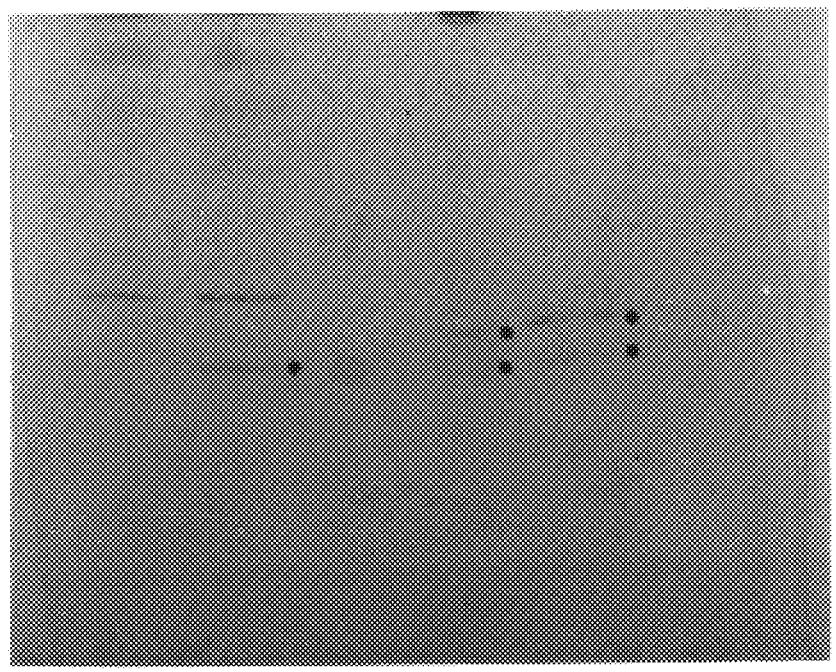
Figure 11A:
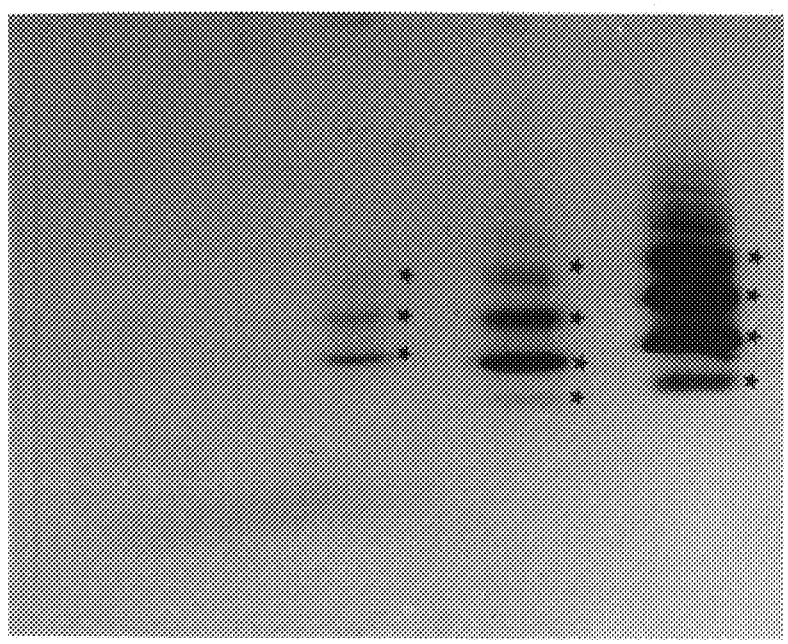
Figure 11B:
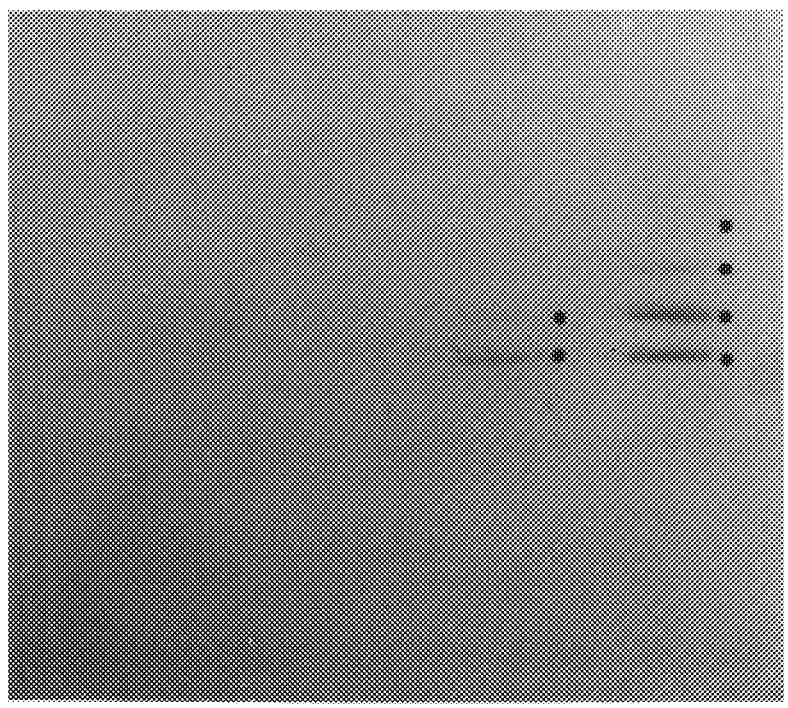

FIG. 11. IEF-PAGE evidence for the overexpression of phytase in *A. niger* CBS 513.88 transformants. Equal volumes of culture supernatants of the *A. niger* parent strain (lane 1), or the transformants pAF 2-2S #8 (lane 2), pFYT3 #205 (lane 3) & #282 (lane 4) were analysed by IEF-PAGE PAGE as described in the legend of FIG. 10. The gels were either stained by a general phosphatase activity stain (A) or by a general protein stain (B). Phytase bands are indicated by an asterisk.

Figure 12:
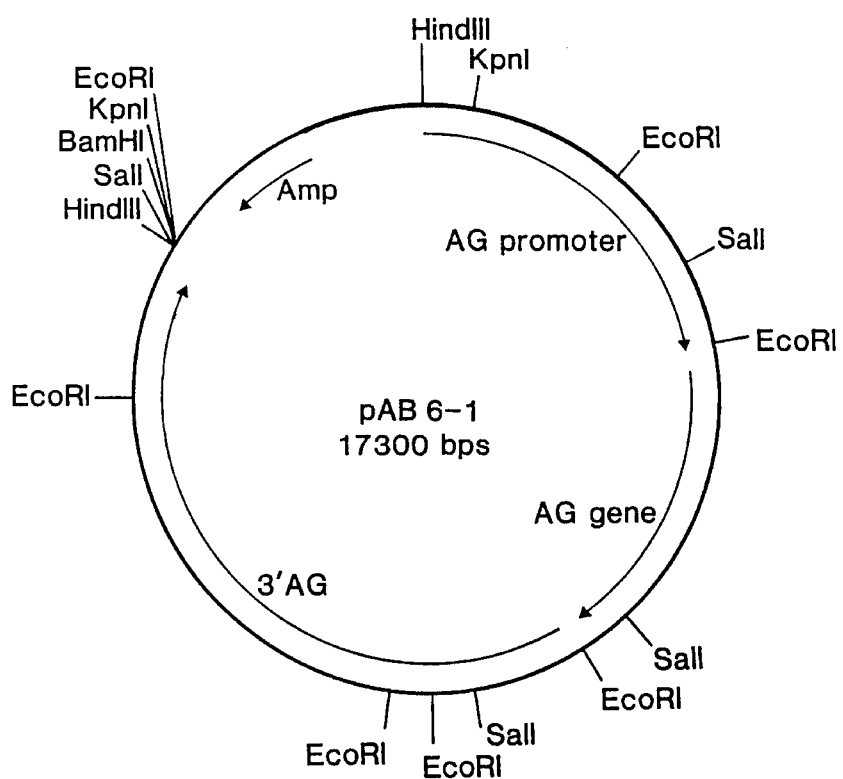

FIG. 12. Physical map of pAB 6-1. The 14.5 kb HindIII DNA insert in pUC19 contains the entire glucoamylase (AG) locus from *A. niger*.

Figure 13:
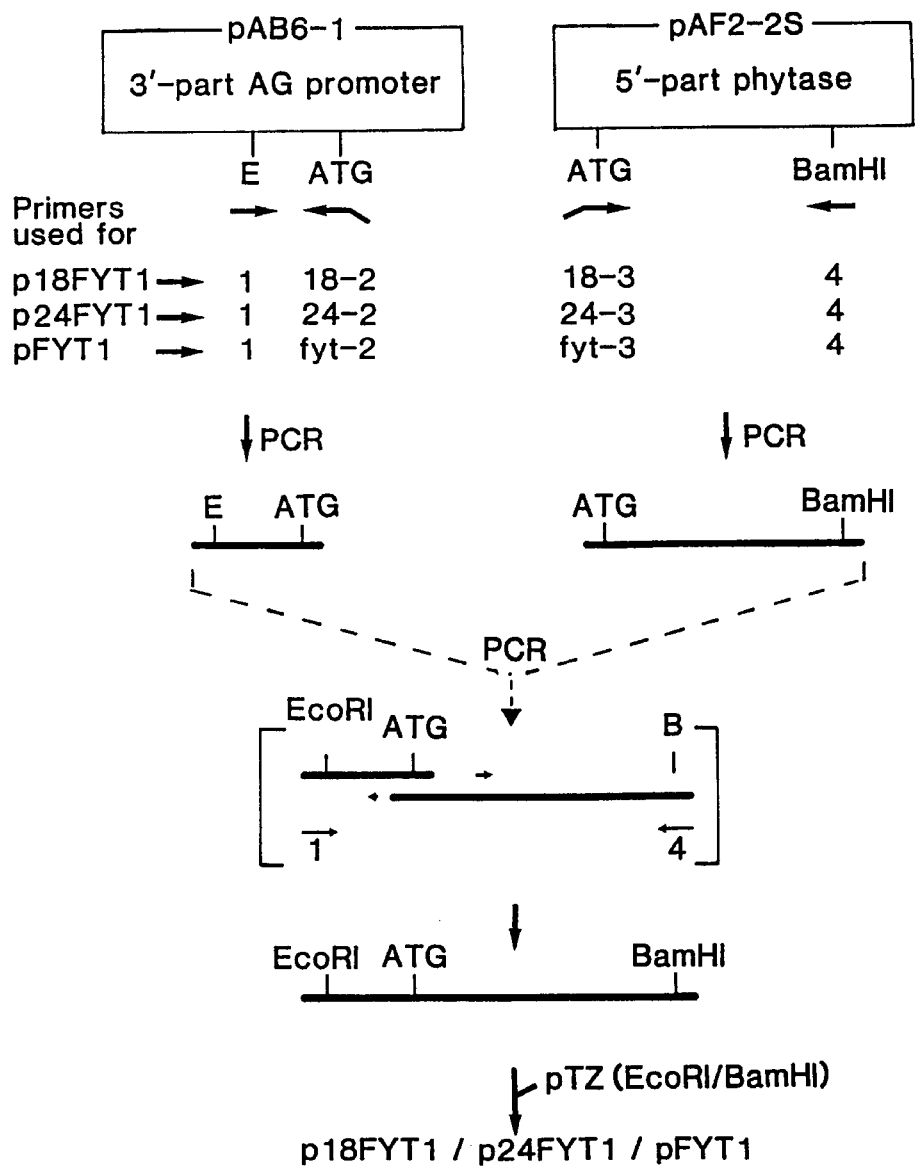

FIG. 13. A schematic view of the generation of AG promoter/phytase gene fusions by the polymerase chain reaction (PCR). The sequences of all oligonucleotide primers used are indicated in the text.

Figure 14:
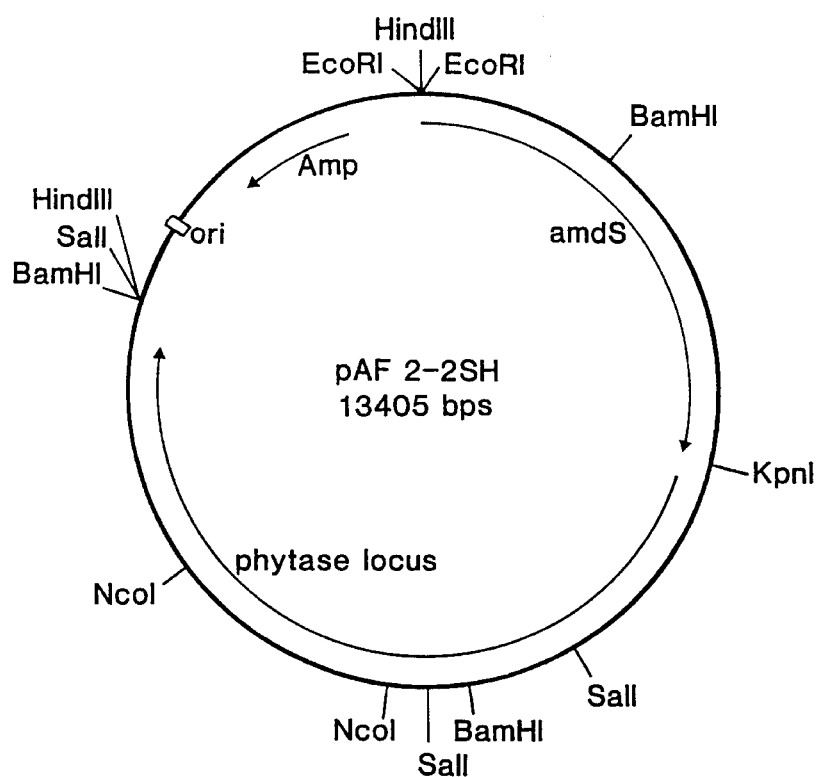

FIG. 14. Physical map of the phytase expression cassette pAF 2-2SH.

Figure 15A:
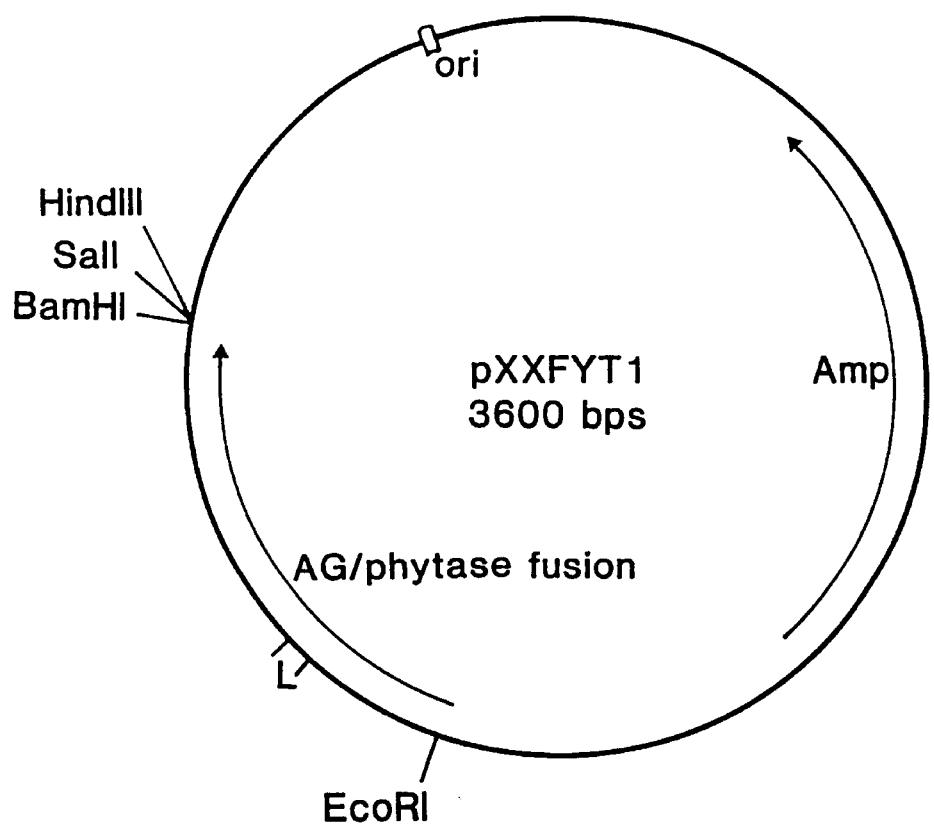
Figure 15B:
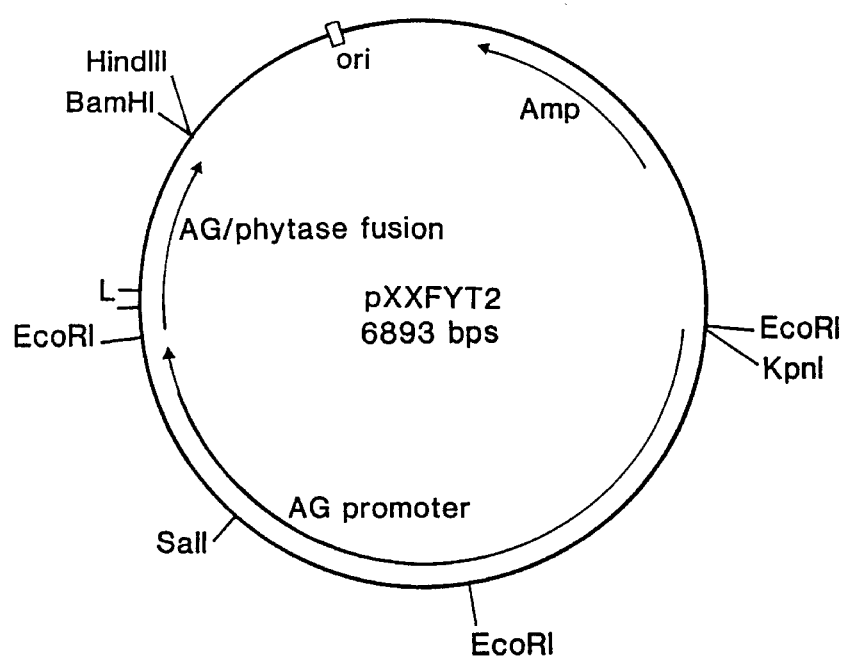
Figure 15C:
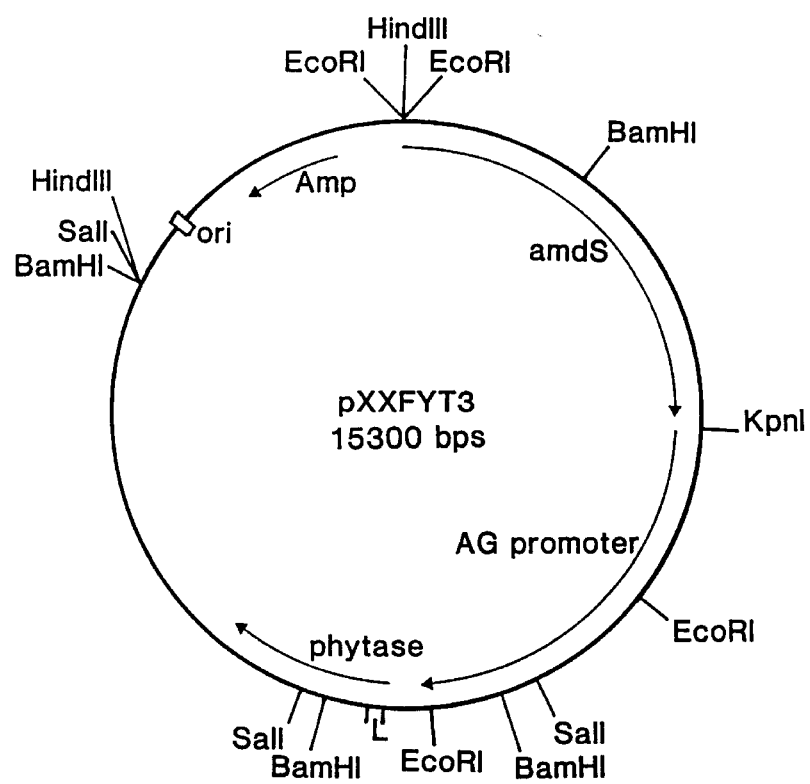

FIG. 15. Physical maps of the intermediate constructs pXXFYT1, pXXFYT2 and the phytase expression cassettes pXXFYT3, wherein XX indicates the leader sequence (L). In p18FYT# and p24FYT#, respectively the 18 aa and the 24 aa AG leader sequence are inserted whereas in pFYT#, the phytase leader is used.

Figure 16:
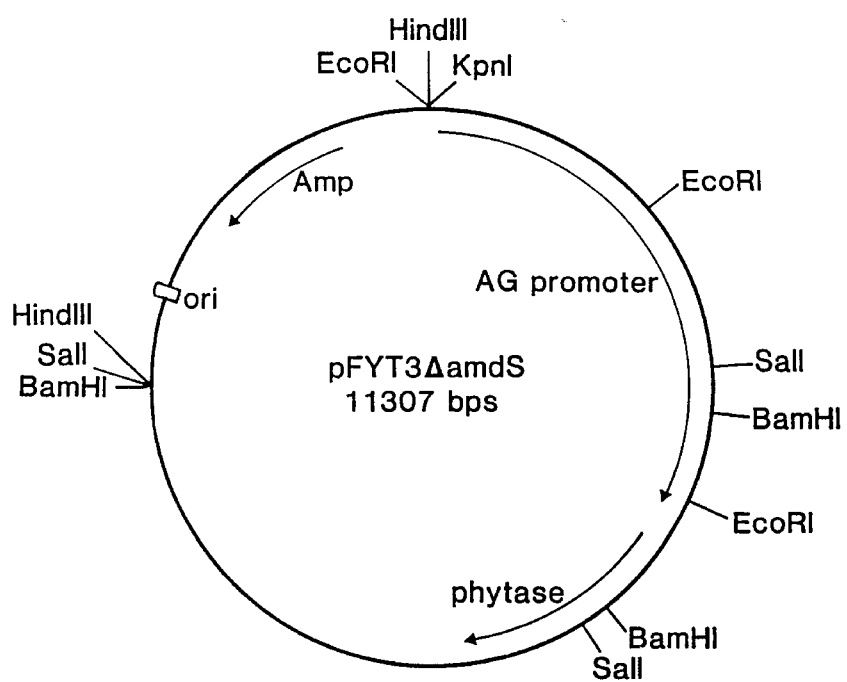

FIG. 16. Physical map of plasmid pFYT3ΔamdS.

Figure 17:
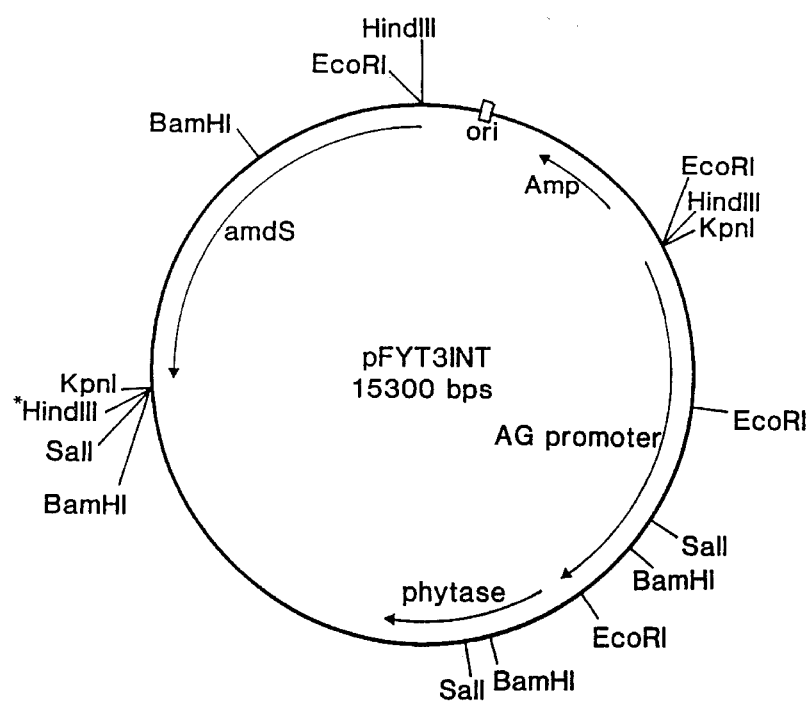

FIG. 17. Physical map of plasmid pFYT3INT.

Figure 18:
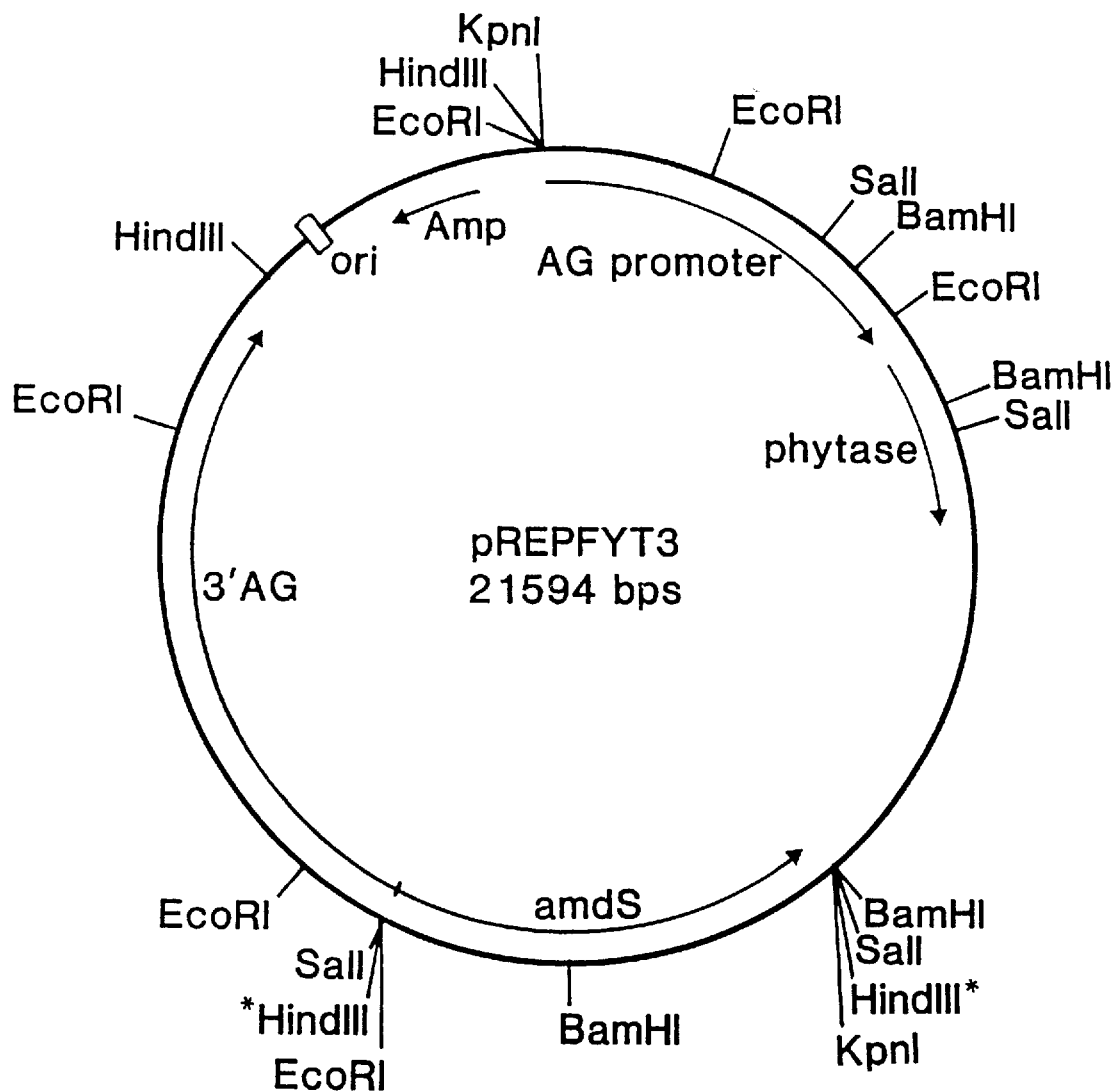

FIG. 18. Physical map of the phytase/AG replacement vector pREPFYT3.

Figure 19A:
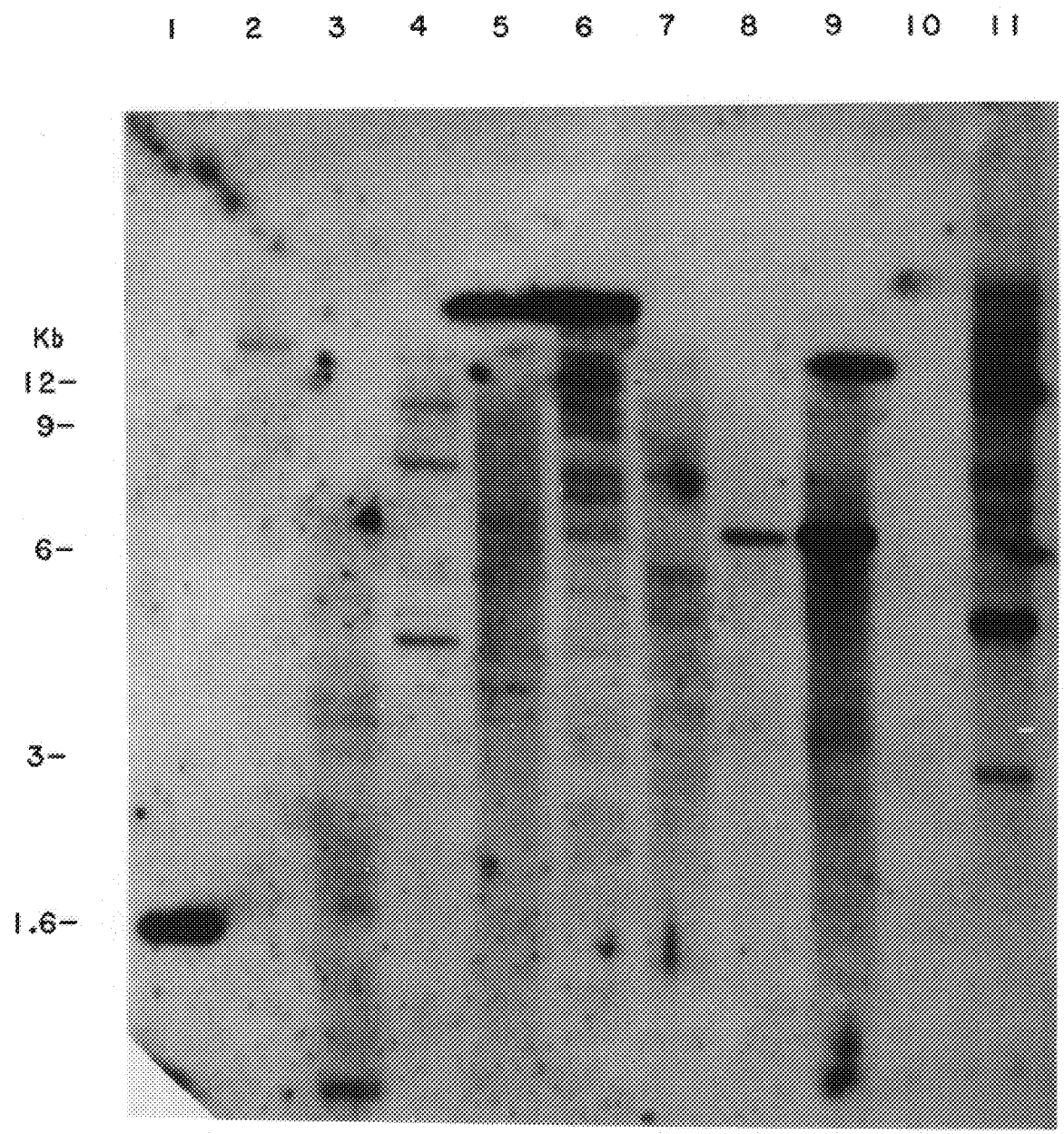
Figure 19B:
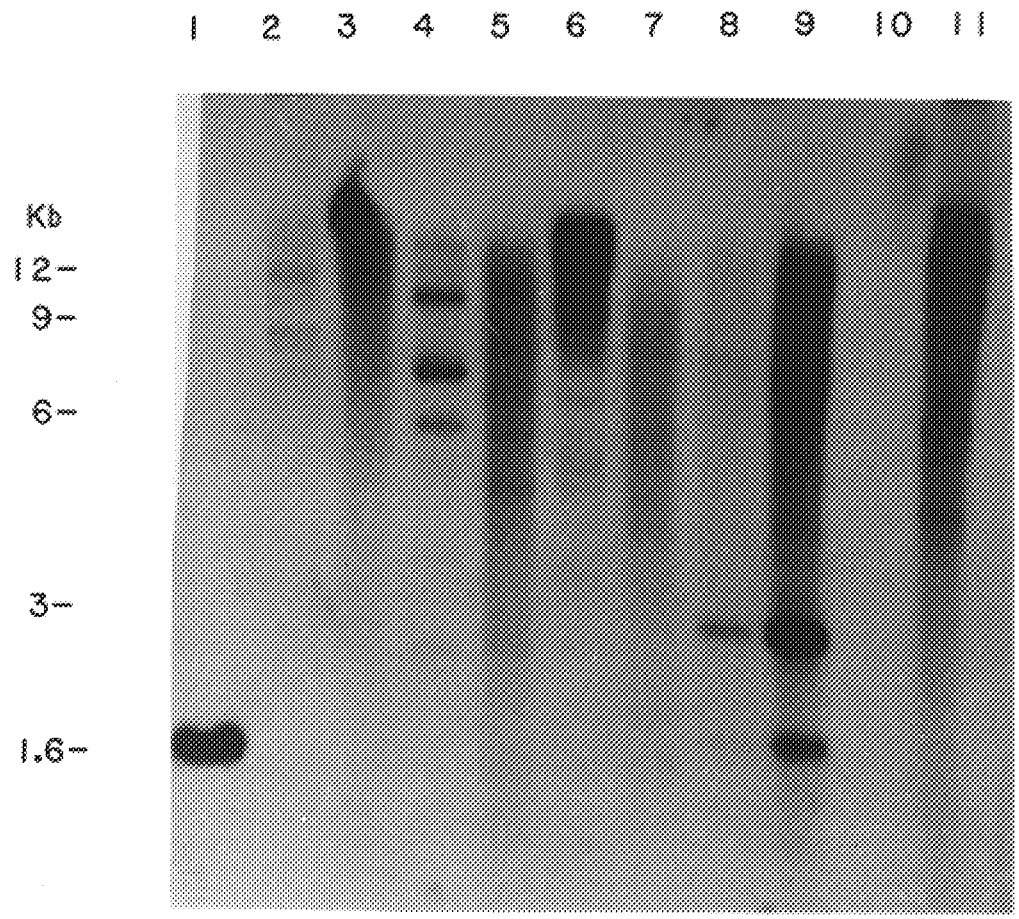

FIG. 19. Autoradiographs of chromosomal DNA, digested with PvuII (A) and BamHI (B) and hybridized with the $^{32}$P-labeled *A. ficuum* phytase cDNA as probe of the microbial species *S. cerevisiae* (lane 2); *B. subtilis* (lane 3); *K. lactis* (lane 4); *P. crysogenum* (lane 5); *P. aeruginosa* (lane 6); *S. lividans* (lane 7); *A. niger* 1 μg (lane 8); *A. niger* 5 μg (lane 9); blank (lane 10); *C. thermocellum* (lane 11). Lane 1: marker DNA.

DETAILED DESCRIPTION OF THE INVENTION

The cloning of the genes encoding selected proteins produced by a microorganism can be achieved in various ways. One method is by purification of the protein of interest, subsequent determination of its N-terminal amino acid sequence and screening of a genomic library of said micro-organism using a DNA oligonucleotide probe based on said N-terminal amino acid sequence. Examples of the successful application of this procedure are the cloning of the Isopenicillin N-synthetase gene from *Cephalosporium acremonium* (S. M. Samson et al. (1985) Nature 318, 191–194) and the isolation of the gene encoding the TAKA amylase for *Aspergillus oryzae* (Boel et al. (1986) EP-A-0238023).

Using this procedure, an attempt has been made to isolate the *Aspergillus ficuum* gene encoding phytase. The protein has been purified extensively, and several biochemical parameters have been determined. The data obtained have been compared to the data published by Ullah (1988a). Both sets of data are given in Table 1, below.

TABLE 1

Biochemical parameters of purified wild-type *A. ficuum* phytase

| Parameter | Present invention | Ullah |
|---|---|---|
| Specific activity* | 100 U/mg protein | 50 U/mg protein |
| Purity: | | |
| SDS-PAGE | 85 kDa | 85/100 kDa |
| IEF-PAGE | 3 or 4 bands | not done |
| Km (Affinity constant) | 250 μM | 40 μM |
| Specificity for: | | |
| Inositol-1-P | not active | not active |
| Inositol-2-P | Km = 3.3 mM | 5% activity |
| pH optimum | 2.5 and 5.5 | 2.5 and 5.5 |
| Temp. optimum (°C.) | 50 | 58 |
| MW (kDa)** | 85 | 85 and 100 |
| MW (unglycosylated)** | 56.5 | 61.7 |
| Isoelectric Point*** | 5.0–5.4 | 4.5 |

\* Phytase activity is measured by Ullah at 58° C. rather than at 37° C. A unit of phytase activity is defined as that amount of enzyme which liberates inorganic phosphorus from 1.5 mM sodium phytate at the rate of 1 μmol/min at 37° C. and at pH 5.50. To compare the fermentation yields and the specific activities, the activities disclosed by Ullah were corrected for the temperature difference. The correction is based on the difference in phytase activity measured at 37° C. and at 58° C. as shown in Table III of Ullah (1988b).
\*\* Apparent Molecular Weight as determined by SDS-PAGE.
\*\*\* As determined by IEF-PAGE In order to isolate the gene encoding phytase, a first set of oligonucleotide probes was designed according to the above-described method (FIG. 2A). The design of these probes was based on the amino acid sequence data. As a control for the entire procedure, similar steps were taken to isolate the gene encoding acid-phosphatase, thereby using the protein data published by Ullah and Cummins ((1987) Prep. Biochem. 17, 397–422). For acid-phosphatase, the corresponding gene has been isolated without difficulties. However, for phytase, the situation appeared to be different. Despite many attempts in which probes derived from the N-terminal amino acid sequence were used, no genomic DNA fragments or clones from the genomic library could be isolated which could be positively identified to encompass the gene encoding phytase.

To overcome this problem, the purified phytase was subjected to CNBr-directed cleavage and the resulting protein fragments were isolated. The N-terminal amino acid sequences of these fragments were determined (FIG. 1B), and new oligonucleotide probes were designed, based on the new data (FIG. 2B). Surprisingly, the new oligonucleotide probes did identify specific DNA fragments and were suited to unambiguously identify clones from a genomic library. No cross hybridization was observed between the new clones or DNA fragments isolated therefrom, and the first set of oligonucleotide probes or the clones isolated using the first set of probes.

It will be appreciated that this second set of probes may also be used to identify the coding sequences of related phytases.

The newly isolated clones were used as probes in Northern blot hybridizations. A discrete mRNA could only be detected when the mRNA was isolated from phytase producing mycelium. When RNA from non-phytase producing mycelium was attempted, no hybridization signal was found. The mRNA has a size of about 1800 b, theoretically yielding a protein having a maximal molecular weight of about 60 kDa. This value corresponds to the molecular weight which has been determined for the non-glycosylated protein, and the molecular weight of the protein as deduced from the DNA sequence.

Moreover, when introduced into a fungal cell by transformation, an increase in phytase activity could be demonstrated. This indicates conclusively that the nucleotide sequence encoding phytase has indeed been isolated. The amino acid sequences which have been determined for the purified phytase enzyme, and for the CNBr fragments obtained therefrom, concur with the amino acid sequence deduced from the sequence which was determined for the cloned gene. The nucleotide sequence and the deduced amino acid sequence are given in FIGS. 6 and 8, and further illustrate the cloned sequence encoding phytase.

The isolation of the nucleotide sequence encoding phytase enables the economical production of phytase on an industrial scale, via the application of modern recombinant DNA techniques such as gene amplification, the exchange of regulatory elements such as e.g. promoters, secretional signals, or combinations thereof.

Accordingly, the present invention also comprises a transformed expression host capable of the efficient expression of high levels of peptides or proteins having phytase activity and, if desired, the efficient expression of acid phosphatases as well. Expression hosts of interest are filamentous fungi selected from the genera Aspergillus, Trichoderma, Mucor and Penicillium, yeasts selected from the genera Kluyveromyces and Saccharomyces and bacteria of the genus Bacillus. Preferably, an expression host is selected which is capable of the efficient secretion of their endogenous proteins.

Of particular interest are industrial strains of Aspergillus, especially *niger, ficuum, awamori* or *oryzae*. Alternatively,

*Trichoderma reesei, Mucor miehei, Kluyveromyces lactis, Saccharomyces cerevisiae Bacillus subtilis* or *Bacillus licheniformis* may be used.

The expression construct will comprise the nucleotide sequences encoding the desired enzyme product to be expressed, usually having a signal sequence which is functional in the host and provides for secretion of the product peptide or protein.

Various signal sequences may be used according to the present invention. A signal sequence which is homologous to the cloned nucleotide sequence to be expressed may be used. Alternatively, a signal sequence which is homologous or substantially homologous with the signal sequence of a gene at the target locus of the host may be used to facilitate homologous recombination. Furthermore, signal sequences which have been designed to provide for improved secretion from the selected expression host may also be used. For example, see Von Heyne (1983) Eur. J. Biochem. 133, 17–21; and Perlman and Halverson (1983) J. Mol. Biol. 167, 391–409. The DNA sequence encoding the signal sequence may be joined directly through the sequence encoding the processing signal (cleavage recognition site) to the sequence encoding the desired protein, or through a short bridge, usually fewer than ten codons.

Preferred secretional signal sequences to be used within the scope of the present invention are the signal sequence homologous to the cloned nucleotide sequence to be expressed, the 18 amino acid glucoamylase (AG) signal sequence and the 24 amino acid glucoamylase (AG) signal sequence, the latter two being either homologous or heterologous to the nucleotide sequence to be expressed.

The expression product, or nucleotide sequence of interest may be DNA which is homologous or heterologous to the expression host.

"Homologous" DNA is herein defined as DNA originating from the same genus. For example, Aspergillus is transformed with DNA from Aspergillus. In this way it is possible to improve already existing properties of the fungal genus without introducing new properties, which were not present in the genus before.

"Heterologous" DNA is defined as DNA originating from more than one genus, i.e., as follows from the example given in the preceding paragraph, DNA originating from a genus other than Aspergillus, which is then expressed in Aspergillus.

Nucleotide sequences encoding phytase activity are preferably obtained from a fungal source. More preferred are phytase encoding nucleotide sequences obtained from the genus Aspergillus. Most preferred sequences are obtained from the species *Aspergillus ficuum* or *Aspergillus niger*.

The region 5' to the open reading frame in the nucleotide sequence of interest will comprise the transcriptional initiation regulatory region (or promoter). Any region functional in the host may be employed, including the promoter which is homologous to the phytase-encoding nucleotide sequence to be expressed. However, for the most part, the region which is employed will be homologous with the region of the target locus. This has the effect of substituting the expression product of the target locus with the expression product of interest. To the extent that the level of expression and secretion of the target locus encoded protein provides for efficient production, this transcription initiation regulatory region will normally be found to be satisfactory. However, in some instances, one may wish a higher level of transcription than the target locus gene or one may wish to have inducible expression employing a particular inducing agent. In those instances, a transcriptional initiation regulatory region will be employed which is different from the region in the target locus gene. A large number of transcriptional initiation regulatory regions are known which are functional in filamentous fungi. These regions include those from genes encoding glucoamylase (AG), fungal amylase, acid phosphatase, GAPDH, TrpC, AmdS, AlcA, AldA, histone H2A, Pyr4, PyrG, isopenicillin N synthetase, PGK, acid protease, acyl transferase, and the like.

The target locus will preferably encode a highly expressed protein gene, i.e., a gene whose expression product is expressed to a concentration of at least about 0.1 g/l at the end of the fermentation process. The duration of this process may vary inter alia on the protein product desired. As an example of such a gene, the gene encoding glucoamylase (AG) is illustrative. Other genes of interest include fungal α-amylase, acid phosphatase, protease, acid protease, lipase, phytase and cellobiohydrolase. Especially preferred target loci are the glucoamylase gene of *A. niger*, the fungal amylase gene of *A. oryzae*, the cellobiohydrolase genes of *T. reesei*, the acid protease gene of *Mucor miehei*, the lactase gene of *Kluyveromyces lactis* or the invertase gene of *Saccharomyces cerevisiae*.

The transcriptional termination regulatory region may be from the gene of interest, the target locus, or any other convenient sequence. Where the construct includes further sequences of interest downstream (in the direction of transcription) from the gene of interest, the transcriptional termination regulatory region, if homologous with the target locus, should be substantially smaller than the homologous flanking region.

A selection marker is usually employed, which may be part of the expression construct or separate from the expression construct, so that it may integrate at a site different from the gene of interest. Since the recombinant molecules of the invention are preferably transformed to a host strain that can be used for industrial production, selection markers to monitor the transformation are preferably dominant selection markers, i.e., no mutations have to be introduced into the host strain to be able to use these selection markers. Examples of these are markers that enable transformants to grow on defined nutrient sources (e.g. the *A. nidulans* amds gene enables *A. niger* transformants to grow on acetamide as the sole nitrogen source) or markers that confer resistance to antibiotics (e.g., the ble gene confers resistance to phleomycin or the hph gene confers resistance to hygromycin B).

The selection gene will have its own transcriptional and translational initiation and termination regulatory regions to allow for independent expression of the marker. A large number of transcriptional initiation regulatory regions are known as described previously and may be used in conjunction with the marker gene. Where antibiotic resistance is employed, the (concentration of the antibiotic for selection will vary depending upon the antibiotic, generally ranging from about 30to 300 μg/ml of the antibiotic.

The various sequences may be joined in accordance with known techniques, such as restriction, joining complementary restriction sites and ligating, blunt ending by filling in overhangs and blunt ligation, Bal31 resection, primer repair, in vitro mutagenesis, or the like. Polylinkers and adapters may be employed, when appropriate, and introduced or removed by known techniques to allow for ease of assembly of the expression construct. At each stage of the synthesis of the construct, the fragment may be cloned, analyzed by restriction enzyme, sequencing or hybridization, or the like. A large number of vectors are available for cloning and the particular choice is not critical to this invention. Normally, cloning will occur in E. coli.

The flanking regions may include at least part of the open reading frame of the target locus, particularly the signal sequence, the regulatory regions 5' and 3' of the gene of the target locus, or may extend beyond the regulatory regions. Normally, a flanking region will be at least 100 bp, usually at least 200 bp, and may be 500 bp or more. The flanking regions are selected, so as to disrupt the target gene and prevent its expression. This can be achieved by inserting the expression cassette (comprising the nucleotide sequence to be expressed and optionally including additional elements such as a signal sequence, a transcriptional initiation regulatory region sequence and/or a transcriptional termination regulatory region sequence) into the open reading frame proximal to the 5' region, by substituting all or a portion of the target gene with the expression construct, or by having the expression construct intervene between the transcriptional initiation regulatory region at the target locus and the open reading frame. As already indicated, where the termination regulatory region is homologous with the region at the target locus, the 3' -flanking region should be substantially larger than a termination regulatory region present in the construct.

The present invention also provides the starting material for the construction of 'second-generation' phytases, i.e. phytase enzymes with properties that differ from those of the enzyme isolated herein. Second-generation phytases may have a changed temperature or pH optimum, a changed specific activity or affinity for its substrates, or any other changed quality that makes the enzyme more suited for application in a defined process. E. coli is the best host for such mutagenesis (e.g. site-directed mutagenesis). Since E. coli lacks the splicing machinery for the removal of introns which might be present in the phytase gene, a cDNA clone of phytase is the sequence of choice to be expressed in E. coli. This cDNA sequence can be readily mutated by procedures well known in the art, after which the mutated gene may be introduced into the desired expression constructs.

The construct may be transformed into the host as the cloning vector, either linear or circular, or may be removed from the cloning vector as desired. The cloning vector is preferably a plasmid. The plasmid will usually be linearized within about 1 kbp of the gene of interest. Preferably, the expression construct for the production of the phytases of the present invention will be integrated into the genome of the selected expression host.

A variety of techniques exist for transformation of filamentous fungi. These techniques include protoplast fusion or transformation, electroporation and micro-projectile firing into cells. Protoplast transformation has been found to be successful and may be used with advantage.

Mycelium of the fungal strain of interest is first converted to protoplasts by enzymatic digestion of the cell wall in the presence of an osmotic stabilizer such as KCl or sorbitol. DNA uptake by the protoplasts is aided by the addition of $CaCl_2$ and a concentrated solution of poly-ethylene glycol, the latter substance causing aggregation of the protoplasts, by which process the transforming DNA is included in the aggregates and taken up by the protoplasts. Protoplasts are subsequently allowed to regenerate on solid medium, containing an osmotic stabilizer and, when appropriate, a selective agent, for which the resistance is encoded by the transforming DNA.

After selecting for transformants, the presence of the gene of interest may be determined in a variety of ways. By employing antibodies, where the expression product is heterologous to the host, one can detect the presence of expression of the gene of interest. Alternatively, one may use Southern or Northern blots to detect the presence of the integrated gene or its transcription product.

Amplification of the nucleotide sequence or expression construct of interest may be achieved via standard techniques such as, the introduction of multiple copies of the construct in the transforming vector or the use of the amdS gene as a selective marker (e.g. Weinans et al. (1985) Current Genetics, 9, 361–368). The DNA sequence to be amplified may comprise DNA which is either homologous or heterologous to the expression host, as discussed above.

The cells may then be grown in a convenient nutrient medium. Low concentrations of a protease inhibitor may be employed, such as phenylmethylsulfonyl fluoride, α2-macro-globulins, pepstatin, or the like. Usually, the concentration will be in the range of about 1 μg/ml to 1 mg/ml. The protease gene(s) may be inactivated in order to avoid or reduce degradation of the desired protein.

The transformants may be grown in either batch or continuous fermentation reactors, where the nutrient medium is isolated and the desired product extracted.

Various methods for purifying the product, if necessary, may be employed, such as chromatography (e.g., HPLC), solvent-solvent extraction, electrophoresis, combinations thereof, or the like.

The present invention also provides a downstream processing method in which the fermentation broth (optionally purified) is filtered, followed by a second germ-free filtration, after which the filtered solution is concentrated. The thus-obtained liquid concentrate may be used as follows:

a) Phytase and other proteins may be precipitated from the liquid concentrate by adding acetone to a final volume of 60% (v/v) under continuous stirring. The precipitate may be dried in a vacuum at 35° C. After grinding the dry powder, the enzyme product may be used as such for application experiments. Recovery yields are about 90%.

b) The liquid concentrate may be spray-dried using conventional spray-drying techniques. Recovery yields vary from 80 to 99%.

c) The liquid concentrate may be mixed with carrier materials such as wheat bran. The thus-obtained mixture may be dried in a spray tower or in a fluid bed.

d) The liquid concentrate may be osmotically stabilized by the addition of e.g. sorbitol. A preservative such as benzoic acid may be added to prevent microbial contamination.

All four formulations may be sold to premix manufacturers, compound feed industries, other distributors and farmers.

The examples herein are given by way of illustration and are in no way intended to limit the scope of the present invention. It will be obvious to those skilled in the art that the phytase gene of the invention can be used in heterologous hybridization experiments, directed to the isolation of phytase encoding genes from other micro-organisms.

Example 1

Fermentation of A. ficuum NRRL 3135

Aspergillus ficuum strain NRRL 3135 was obtained from the Northern Region Research Lab, USDA, 1815 North University Street, Peoria, Ill., U.S.A. Fungal spore preparations were made following standard techniques.

Spores and subsequently cells were transferred through a series of batch fermentations in Erlenmeyer flasks to a 10 l fermentor. After growth in batch culture, the contents of this fermentor were used as inoculum for a final 500 liter batch fermentation.

The media used contains: 91 g/l corn starch (BDH Chemicals Ltd.); 38 g/l glucose.$H_2O$; 0.6 g/l $MgSO_4.7H_2O$; 0.6 g/l KCl; 0.2 g/l $FeSO_4.7H_2O$ and 12 g/l $KNO_3$. The pH was maintained at 4.6±0.3 by automatic titration with either 4N NaOH or 4N $H_2SO_4$.

Cells were grown at 28° C. at an automatically controlled dissolved oxygen concentration of 25% air saturation. Phytase production reached a maximum level of 5–10 U/ml after 10 days of fermentation.

Example 2
Purification and characterization of A. ficuum phytase
A. Phytase activity assay 100 μl of broth filtrate (diluted when necessary) or supernatant or 100 μl of demiwater as reference are added to an incubation mixture having the following composition:

0.25M sodium acetate buffer pH 5.5, or
glycine HCL-buffer pH 2.5
1 mM phytic acid, sodium salt
demiwater up to 900 μl The resulting mixture is incubated for 30 minutes at 37° C. The reaction is stopped by the addition of 1 ml of 10% TCA (trichloroacetic acid). After the reaction has terminated, 2 ml of reagent (3.66 g of $FeSO_4.7H_2O$ in 50 ml of ammonium molybdate solution (2.5 g $(NH_4)_6Mo_7O_{24}.4H_2O$ and 8 ml $H_2SO_4$, diluted up to 250 ml with demiwater)) is added.

The intensity of the blue color is measured spectrophotometrically at 750 nm. The measurements are indicative of the quantity of phosphate released in relation to a calibration curve of phosphate in the range of 0–1 mMol/l.

Phosphatase stain

Components with phosphatase activity were detected by isoelectric focusing using a general phosphatase stain. The gel was incubated with a solution of α-naphthylphosphate and Fast Garnet GBC salt (Sigma, 0.1 & 0.2% (w/v), respectively) in 0.6M sodium acetate buffer pH 5.5. The reaction, which results in the appearance of a black precipitate, was either terminated with methanol:acetic acid (30:10 %, v/v), or, should the protein having phytase activity be further required, by rinsing with distilled water.

B. Purification of A. ficuum phytase

Phytase was purified to homogeneity from the culture broth of A. ficuum NRRL 3135. The broth was first made germ-free by filtration. The resulting culture filtrate was subsequently further concentrated in a Filtron ultrafiltration unit with 30 kD cutoff filters. The pH and ionic strength of the sample were adjusted for the purification procedure by washing the sample with 10 mM sodium acetate buffer pH 4.5. The final concentration in this ultrafiltration procedure was approximately 20 fold.

The sample was then applied to a cation exchanger (S-Sepharose Fast-Flow in a HR 16/10 20 ml column, both obtained from Pharmacia) in a Waters Preparative 650 Advanced Protein Purification System. The proteins bound were eluted with a sodium chloride gradient from 0–1M in the sodium acetate buffer. Phytase eluted at approximately 250 mM NaCl. Phytase activity containing fractions were pooled, concentrated and desalted by ultrafiltration. The resulting solution was applied to an anion exchanger (Q-Sepharose Fast-Flow in a HR 16/10 20 ml column, Pharmacia), and the proteins were again eluted by a sodium chloride gradient from 0–1M in the acetate buffer described above. Phytase was eluted from this column at approximately 200 mM NaCl.

The result of these purification steps is a partially purified phytase preparation with a specific activity of approximately 40–50 U/mg protein, indicating a 25-fold purification.

Analysis of the purity of the partially purified phytase indicated the presence of a major impurity with a molecular weight of approximately 100 kDa (FIG. 1B, sequence E). Isoelectric focusing indicated the presence of a number of phosphatase activity containing enzymes, including 3–4 phytase subforms (isoelectric points varying from 5.0–5.4) (FIG. 1A, sequences A and B).

In order to obtain a homogeneous phytase preparation, a further two-fold purification was achieved by a subsequent separation of the components of the partially purified phytase by isoelectric focusing in a LKB Multiphor system on Ampholine PAG plates (pH range 4–6.5). The proteins with phosphatase activity (including the phytase) were detected by the general phosphatase staining procedure described above. The bands of interest were subsequently excised from the gel and the active protein was eluted by a 16 hr incubation of the gel slices in 10 mM sodium acetate buffer 5.5. The protein fractions were analysed in the specific phytase activity assay, as described in Example 2, thus discriminating the phytase fractions from other acid phosphatases. The final purification factor for phytase was approximately 60 fold (specific activity of final preparation 100 U/mg protein). In this final purification step it was also possible to isolate different subforms of phytase (FIG. 1A, sequences A and B).

Monoclonal antibodies directed against the A. ficuum phytase were prepared, providing an effective purification procedure. The antibody was coupled to cyanogen bromide-activated Sepharose 4B (5 mg/ml gel), and this matrix was used in a immunoaffinity column. The matrix was shown to bind approximately 1 mg phytase per ml. The phytase could be eluted from the affinity column with a pH 2.5 buffer (100 mM glycine-HCl, 500 mM NaCl) without any loss of activity. This procedure can be used to isolate homogeneous phytase from a crude culture filtrate in one single step with an 80% recovery and a 60-fold purification.

C. Deglycosylation of phytase

A. ficuum phytase (70 μg protein) was incubated with 2.5 U N-Glycanase (Genzyme) in 0.2M sodium phosphate buffer pH 8.6 and 10 mM 1,10-phenanthroline in a total volume of 30 μl.

After 16 hrs at 37° C., the extent of deglycosylation was checked by electrophoresis (Phast System, Pharmacia). The apparent molecular weight of the phytase was found to decrease from 85 kDa to approximately 56.5 kDa. The periodic acid Schiff (PAS) sugar staining, which identifies native phytase as a glycoprotein, failed to detect any residual carbohydrates attached to the protein. The complete removal of carbohydrate was further substantiated by the sensitive lectin-blotting method. Native and deglycosylated phytase (both 1.5 μg) were run on a standard SDS-PAGE gel and electrophoretically transferred to a PVDF membrane (Immobilon, Millipore) in 25 mM TRIS-glycine buffer pH 8.3, 20% (v/v) methanol, for a period of 16 hrs at 30V.

The membrane was subsequently incubated with 1% (w/v) bovine serum albumin in phospate buffered saline and incubated with concanavalin A-peroxidase (Sigma, 10 μg/ml in phosphate buffered saline). The peroxidase was then stained with 4-chloro-1-naphthol (Sigma).

This sensitive method also failed to detect any residual carbohydrate attached to the deglycosylated phytase.

After deglycosylation, phytase has completely lost its activity, possibly due to aggregation of the enzyme.

Example 3
Determination of the amino acid sequence of phytase and design of oligonucleotide probes
A. Determination of the N-terminal amino acid sequence Phytase was electrophoretically transferred from SDS-PAGE or from IEF-PAGE onto a PVDF blotting membrane (Immobilon, Millipore). Electroblotting was performed in 10 mM CAPS (3-cyclohexylamino-propanesulfonic acid) buffer pH 11.0, with 10% (v/v) methanol, for a period of 16 hrs, at 30V and 40° C.

The protein was located with Coomassie Brilliant Blue staining. The band of interest was excised, further destained in methanol and subjected to gas-phase sequencing. The procedure has been carried out several times, using several individual preparations. The results obtained are given in FIG. 1A (sequences A and B).

The amino acid sequence has also been determined for a 100 kDa protein that was present in crude preparations. The data obtained for this protein are given in FIG. 1C. This sequence shows considerable homology with the acid phosphatase that has been isolated from *Aspergillus niger* (MacRae et al. (1988) Gene 71, 339–348).

B. Determination of internal amino acid sequences
  Protein fragmentation by cyanogen bromide Phytase, purified to homogeneity, was transferred into 100 mM $NaHCO_3$ by ultrafiltration (Microconcentrator Centricon 30, Amicon). The protein was subsequently lyophilized, dissolved in 70% trifluoroacetic acid (v/v), and incubated for 6 hr with an approximately 300-fold molar excess of CNBr. The reaction was terminated by dilution of the mixture with water. The resulting fragments were again lyophilized. The sample was then dissolved in SDS-PAGE sample buffer containing DTT (dithiothreitol), and the extent of fragmentation was determined by PAGE. Analytical PAGE was performed on a Pharmacia Phast-System unit, on 20% SDS-PAGE gels. The gels were prerun to create a continuous buffer system to improve the separation of the small peptides (according to the manual). Peptides were detected using a silver-staining technique known in the art, since Coomassie Brilliant Blue failed to detect the smallest peptide. The result of the procedure was a complete degradation of phytase into peptides with molecular weights of <2.5 kDa, 36 kDa, 57 kDa and 80 kDa.

The peptides were isolated for gas-phase sequencing by SDS-Tricine-PAGE as described by Schagger & Jagow (1987) Anal. Biochem. 166, 368–379 followed by electroblotting as described above.

The N-terminus of the 57 kDa fragment is identical to the N-terminus of phytase as determined by Ullah (1988b, supra), with the exception of the first four amino acids which are absent (FIG. 1A, sequence B). The N-terminal sequences of the 2.5 kDa and 36 kDa peptides are shown in FIG. 1B as sequences A and B.

C. Oligonucleotide probes

Oligonucleotide probes have been designed, based on the amino acid sequences given in FIG. 1A and 1B, and were prepared using an Applied Biosystems ABI 380B DNA synthesizer. These oligonucleotides are given in FIG. 2A and 2B.

Example 4
Hybridization of genomic blots and genomic libraries with a first set of oligonucleotide probes Genomic DNA from *A. ficuum* has been isolated by grinding the mycelium in liquid nitrogen, using standard procedures (e.g. Yelton et al (1984) Proc. Natl. Acad. Sci.-U.S.A., 1470–1474). A genomic library was constructed in the bacteriophage vector lambda EMBL3, using a partial Sau3A digest of *A. ficuum* NRRL 3135 chromosomal DNA, according to standard techniques (e.g. Maniatis et al. (1982) *Molecular cloning, a laboratory manual*, Cold Spring Harbor Laboratory, New York). The thus-obtained genomic library contained 60 to 70 times the *A. ficuum* genome. The library was checked for the occurrence of plaques without insert by hybridization with the lambda EMBL3 stuffer fragment. Less than 1% of the plaques were observed to hybridize to the lambda EMBL3 probe. The insert size was 13 to 17 kb.

To identify conditions and probes that were suited for the screening of the genomic library, genomic DNA was digested with several restriction enzymes, separated on agarose gels and blotted onto Genescreen plus, using the manufacturers instructions. The blots were hybridized with all oligonucleotide probes. Hybridization was performed usings conditions of varying stringency (6×SSC, 40° to 60° C. for the hybridization; up to 0.2×SSC, 65° C. for the washing). Probes 1068 and 1024 (FIG. 2A) were selected for the screening of the genomic library, although no common DNA fragments could be identified that hybridized specifically with both probes. Acid-phosphatase probe 1025 (FIG. 3) gave a specific and discrete hybridization signal and hence this probe was selected for screening the genomic library for the acid phosphatase gene.

Using all three probes, hybridizing plaques could be identified in the genomic library. The hybridization signal corresponding to probe 1025 (acid phosphatase) was strong and reproducible. Hybridization signals of variable intensity were observed using probes 1024 and 1068 (phytase). No cross hybridization between the two series was observed. All three series of plaques were rescreened and DNA was isolated from eight single, positive hybridizing plaques (Maniatis et al., supra). In each series, clones that contained identical hybridizing fragments could be identified, indicating that the inserts of said clones are related and probably overlap the same genomic DNA region. Again, no cross-hybridization could be demonstrated using the two phytase specific series (probes 1024 and 1068), indicating that, although both probes used to isolate the two series of clones were obtained from the N-terminal amino acid sequence of the protein, different genomic DNA fragments had been identified and cloned.

All three series of clones were hybridized with Northern blots containing mRNA isolated from induced and non-induced mycelium (Example 6). The acid phosphatase-specific clones, as well as the isolated internal 3.1 kb SalI fragment from these clones, hybridized exclusively to induced mRNA samples. The mRNA identified by the acid phosphatase-specific probes is about 1800 b in length, which agrees with the known size of the protein (68 kDa, Ullah and Cummins (1987) Prep. Biochem. 17, 397–422). No hybridization of the phytase-specific clones with specific mRNA's could be demonstrated. We have thus concluded that the above-described method was unsuccessful in cloning the gene encoding phytase. It may be further concluded that this failure is not due to a failure in the method used, since the method has been successfully applied to identify the gene encoding acid phosphatase. The lambda clone containing the acid phosphatase gene was deposited on Apr. 24, 1989 at the Centraal Bureau voor Schimmelcultures, Baarn, The Netherlands and has been assigned accession number CBS 214.89. A 10 kb BamHI fragment has been isolated from phage Z1 and subcloned into pUC19. This subclone contains the entire gene encoding acid phosphatase. The subclone, pAF 1-1 (FIG. 5) was deposited on Apr. 24, 1989 as CBS 213.89.

Example 5
Isolation of the gene encoding phytase, using a second set of oligonucleotide probes Probes have been designed using the N-terminal amino acid sequence of CNBr-generated fragments (FIG. 2B, probes 1295, 1296 and 1297) and have been hybridized with genomic DNA as described above. The feasibility of using these probes in the isolation of the gene encoding phytase was again studied by Southern hybridization of genomic blots with the probes. This time, hybridizing fragments of corresponding lengths could be identified, using all three probes, despite the fact that the probes have been derived from non-overlapping regions. No hybridization was found between the new set of probes and the clones that have been isolated using the first set of probes (Example 4). Therefore, the genomic library was rescreened using all three probes in separate experiments. A subset of the clones (lambda AF201, 219, 241 and 243) isolated with each individual probe also hybridized with both other probes, indicating that in this case, using the three different probes, clones were isolated from a single genomic region. Attempts were made to hybridize the newly isolated clones with probes 1024 and 1068. In both cases, no hybridization with the newly isolated clones was observed under conditions in which both probes had successfully hybridized to the clones which were isolated using these probes (see Example 4). This demonstrates that the newly isolated clones have no homology to the probes derived from the N-terminus of the purified phytase.

A lambda EMBL3-clone, which hybridizes to all three probes (1295–1297), was named lambda AF201 (FIG. 4) and was deposited on Mar. 9, 1989 as CBS 155.89.

A 5.1 kb BamHI fragment of lambda AF201 (subcloned in pUC19 and designated pAF 2-3, see FIG. 4), hybridizing to all three oligonucleotide probes, was used to probe a Northern blot. In this case, a discrete mRNA having a size of 1800 bases was identified. This mRNA was found only in induced mycelium. Similar results were obtained when the oligonucleotides were-used as probes. Therefore, using the new set of probes, a common DNA fragment has been identified, which hybridizes specifically to an induced mRNA. The length of this mRNA (1800 b) is sufficient to encode a protein of about 60 kDa, which is about the size of the non-glycosylated protein. Clearly, the isolated fragments contain at least part of the gene encoding phytase.

Example 6
Isolation of "induced" and "non-induced" mRNA

It is known from the literature that the synthesis of phytase by A. ficuum is subject to a stringent phosphate-dependent regulation (Han and Callagher (1987) J. Indust. Microbiol. 1, 295–301). Therefore, the demonstration that an isolated gene is subject to a similar regulation can be considered to support the evidence that the gene of interest has been cloned.

In order to isolate mRNA that has been synthesized under both producing and non-producing conditions, A. ficuum NRRL 3135 was grown as follows. Spores were first grown overnight in non-inducing medium. The next day, the mycelium was harvested, washed with sterile water and inoculated into either inducing or non-inducing medium. The medium used contains (per liter): 20 g corn starch; 7.5 g glucose; 0.5 g $MgSO_4.7H_2O$; 0.2 g $FeSO_4.7 H_2O$; and 7.2 g $KNO_3$. For the induction of phytase, up to 2 g/l corn steep liquor was added to the medium, while non-inducing medium contains 2 g/l $K_2HPO_4$. The mycelium was grown for at least a further 100 hours. Samples were taken at selected intervals. Phytase production was followed by the phytase assay as described in Example 2A. Denatured mRNA was separated by electrophoresis and blotted onto Genescreen plus. The blots were hybridized with $^{32}$P-labelled pAF 2-3 or with the isolated 3.1 kb SalI fragment from pAF 1-1 (acid phosphatase) from Example 4. The results are shown in Table 2.

Positive hybridization of the phytase specific 5.1 kb BamHI fragment and the acid phosphatase specific 3.1 kb SalI fragment with isolated mRNA is observed only when cells are grown under conditions which are known to induce the synthesis of phytase and acid phosphatases. From these results it has been concluded that the isolated genes are regulated as expected for phytase and acid phosphatases.

TABLE 2

Hybridization of Northern blots using the phytase-specific 5.1 kb BamHI fragment (A) or the acid phosphatase specific 3.1kb SalI fragment (B) as a probe; a + indicates the presence of the 1800 b phytase mRNA or the 1800 b acid phosphatase mRNA. The relative phytase activity was determined for the 24 hr. samples: induced cultures have 10 times more phytase activity than non-induced cultures.

|   | Time after inoculation | Induced | Non-induced |
|---|---|---|---|
| A | 24 hours | + | − |
| B | 24 hours | + | − |

Example 7
Evidence for the cloning of the phytase gene

To obtain definitive proof for the successful isolation of the gene encoding phytase, and to study the feasibility of increasing the expression of the cloned gene, the phytase gene was subcloned into a suitable vector and transformed to A. niger 402 (ATCC 9092). To this end, the phytase gene was isolated from the lambda clone AF201 as a 10 kb NruI fragment and cloned into the StuI site of the vector pAN 8-1 (Mattern, I. E. and Punt, P. J. (1988) Fungal Genetics Newsletter 35, 25) which contains the ble gene (conferring resistance to phleomycin) as a selection marker. The resulting construct was named pAF 28-1 (FIG. 4) and was transformed to A. niger 402 according to the procedure as described in Example 9, with the exception that the protoplasts were plated on Aspergillus minimal medium supplemented with 30 μg phleomycin/ml and solidified with 0.75% agar. Single transformants were purified and isolated and were tested for production in shake flasks, as described in Examples 1 and 2. As controls, transformants possessing only the vector, as well as the untransformed host were also tested (Table 3). Only A. niger 402 containing pAF 28-1 appeared to produce a phytase that reacted with a specific monoclonal antibody directed against A. ficuum phytase. The phytase reacting with this monoclonal antibody could be eluted from an immuno affinity column at pH 2.5 and was shown to be identical in molecular weight, degree of glycosylation, isoelectric point and specific activity to the A. ficuum phytase. This finding provides clear evidence that A. niger 402 cells transformed with pAF 28-1 express a phytase that is virtually identical to the A. ficuum phytase. Similar expression was not observed in either type of control cells.

TABLE 3

| Strain | Phytase/Activity U/ml | % of phytase-activity adsorbed onto the immunoaffinity column |
|---|---|---|
| A. niger 402 | 0.5 | 0 |
| A. niger 402 pAF 28-1 | 0.7 | 10 |
| A. niger 402 pAN 8-1 | 0.5 | 0 |

Strains were grown under induced conditions (Example 6).
Samples were taken after 96 hours of growth.

Example 8
Characterization of the Phytase gene.

The lambda clones containing the phytase gene have been analyzed by digestion with various restriction enzymes. A map of the genomic region encompassing the phytase gene is given in FIG. 4. Defined restriction fragments have been subcloned in the cloning vector pUC19, as indicated in FIG. 4.

It has previously been shown (Example 5) that the 5.1 kb BamHI fragment present in pAF 2-3 encompasses at least part of the phytase gene. Moreover the oligonucleotide probes 1295 and 1297 (FIG. 2B) were shown to hybridize to the SalI insert from pAF 2-7 (positions of pAF 2 clones are presented in FIG. 4), while probe 1296 probably spans the SalI site between the fragments in pAF 2-6 and pAF 2-7. The results of these experiments indicate that the phytase encoding sequence is located in the lefthand part of the BamHI insert of pAF 2-3.

Subsequently the nucleotide sequences of the inserts of plasmids pAF 2-3, pAF 2-6, and pAF 2-7 have been determined completely using the dideoxy chain termination method (Sanger et al. (1977) Proc. Natl. Acad. Sci. USA 74, 5463–5467) and shotgun strategies described by Messing et al. (1981, Nucl. Acids Res. 9, 309–321). In addition specific oligonucleotides were synthesized based on nucleotide sequence information obtained during the sequencing procedure.

The complete nucleotide sequence of clones pAF 2-3, pAF 2-6, and pAF 2-7 encompassing the chromosomal phytase gene locus is compiled in FIG. 6, a graphic representation is given in FIG. 7.

Analysis of the protein coding capacity of the complete sequence revealed that the N-terminal amino acid sequence of the mature protein was encoded starting from nucleotide position 381 (the N-terminus disclosed by Ullah is located at position 369). Furthermore, the N-terminal amino acid sequence of the 36 kDa and 2.5 kDa internal peptide fragments (see FIG. 1B—sequences B and A) were found to be encoded at nucleotide positions 1101 and 1548, respectively. The open reading frame stops at nucleotide position 1713.

These findings clearly prove the identity of the characterized chromosomal locus as containing phytase encoding DNA sequence.

Directly upstream of the chromosomal sequence encoding the mature phytase protein, no ATG start codon can be found within the reading frame contiguous with the mature protein open reading frame; however, using intron-exon boundary characteristics, an intron can be postulated between nucleotide positions 254 and 355, bringing the ATG codon at nucleotide position 210 in frame with the mature phytase encoding open reading frame. The derived amino acid sequence of this N-terminal extension closely fits the rules for a secretion signal sequence as published by von Heyne (1983, Eur. J. Biochem. 133, 17–21).

To confirm these hypotheses the phytase cDNA was isolated by PCR-amplification with specific phytase primers and a total mRNA/cDNA population as template according to the procedures described below.

Isolation of poly A$^+$ RNA from Aspergillus ficuum.

Total RNA was isolated from A. ficuum NRRL 3135 grown under induced conditions as mentioned in Example 6. Dry mycelium was frozen with liquid nitrogen and ground. Subsequently, the powder was homogenized in an Ultra-Turrax (full speed during 1 minute) in 3M LiCl, 6M urea at 0° C. and maintained overnight at 4° C. as described by Auffrey & Rougeon (Eur.J.Biochem., 107, 303–314, 1980). Total cellular RNA was obtained after centrifugation at at 16,000 g for 30 minutes and two successive extractions with phenol: chloroform: isoamylalcohol (50:48:2). The RNA was precipitated with ethanol and dissolved in 1 ml 10 mM Tris-HCl (pH 7.4), 0.5% SDS. For poly A selection the total RNA sample was heated for 5 minutes at 60° C., adjusted to 0.5M NaCl and subsequently applied to an oligo(dT)-cellulose column. After several washes with a solution containing 10 mM Tris-HCl pH 7.4, 0.5% SDS and 0.1 M NaCl, the poly A$^+$RNA was collected by elution with 10 mM Tris-HCl pH 7.4 and 0.5% SDS.

Preparation of the mRNA/cDNA complex

For the synthesis of the first cDNA strand 5 μg of poly A$^+$RNA was dissolved in 16.5 μl H$_2$O and the following components were added: 2.5 μl RNasin (30 U/μl); 10 μl of a buffer containing 50 mM Tris-HCl pH 7.6, 6 mM MgCl$_2$ and 40 mM KCl; 2 μl 1M KCl; 5 μl 0.1M DTT; 0.5 μl oligo (dT)$_{12-18}$ (2.5 mg/ml); 5 μl 8 mM dNTP-mix; 5 μl BSA (1 mg/ml) and 2.5 μl Moloney MLV reverse transcriptase (200 U/ml). The mixture was incubated for 30 minutes at 37° C. and the reaction was stopped by addition of 10 μl 0.2M EDTA and 50 μl H$_2$O. An extraction was performed with chloroform and after centrifugation 110 μl 5M NH$_4$Ac and 440 μl ethanol were successively added to the supernatant. Precipitation of the mRNA/cDNA complex was performed in a dry ice/ethanol solution for 30 minutes. The mRNA/cDNA was collected by centrifugation, subsequently washed with 70% ice-cold ethanol and dissolved in 20 μl H$_2$O.

Cloning of phytase cDNA fragments

Isolation of the cDNA-encoding phytase sequences were performed by the polymerase chain reaction (PCR) in two fragments. Four synthetic oligonucleotide primers were designed based on the genomic phytase sequence as presented in FIG. 6.

Oligo 1: 5'-GGG.TAG.AAT.TCA.AAA.ATG.GGC.GTC. TCT.GCT.GTT.CTA-3'(SEQ ID NO:34)

Oligo 2: 5'-AGT.GAC.GAA.TTC.GTG.CTG.GTG.GAG. ATG.GTG.TCG-3'(SEQ ID NO:15)

Oligo 3: 5'-GAG.CAC.CAA.GCT.GAA.GGA.TCC-3'(SEQ ID NO:36)

Oligo 4: 5'-AAA.CTG.CAG.GCG.TTG.AGT.GTG.ATT. GTT.TAA.AGG.G-3'(SEQ ID NO:37)

Oligo 1 contains the nucleotide sequence downstream of the phytase ATG startcodon (position 210 to 231) flanked at the 5'border by an EcoRI-site; oligo 2 contains the nucleotide sequence immediately upstream of the SalI-site (position 1129 to 1109) also flanked by an additional EcoRI-site; oligo 3 contains the nucleotide sequence around the BamHI-site (position 845 to 865) and oligo 4 contains a nucleotide sequence positioned downstream of the phytase stopcodon (position 1890 to 1867) flanked by an additional PstI-site.

The polymerase chain reactions were performed according to the supplier of Taq-polymerase (Cetus). As template the solution (1.5 μl) containing the mRNA/cDNA hybrids (described above) was used and as primers 0.3 μg of each of the oligos 1 and 2 in the reaction to amplify the N-terminal phytase cDNA part and oligos 3 and 4 in the reaction to amplify the C-terminal phytase cDNA part (see FIG. 8). After denaturation (7 minutes at 100° C.) and addition of 2 U Taq-polymerase the reaction mixtures were subjected to 25 amplification cycles (each: 2'at 55° C., 3'at 72° C., 1'at 94° C.) in a DNA-amplifier of Perkin-Elmer/Cetus. In the last cycle the denaturation step was omitted. After digestion (EcoRI for the N-terminal cDNA part and BamHI and PstI for the C-terminal cDNA part), both cDNA fragments were cloned into the appropriate sites of pTZ18R (Promega).

The nucleotide sequence of both obtained PCR fragments was determined using the dideoxy chain termination technique (Sanger, supra) using synthetic oligonucleotides designed after the chromosomal phytase gene sequence, as primers and total amplified DNA as well as cloned cDNA fragments as template. The sequence of the. cDNA region encoding the phytase protein and the derived amino acid sequence of the phytase protein are depicted in FIG. 8.

The cDNA sequence confirmed the location of the intron postulated above, and indicated that no other introns were present within the chromosomal gene sequence.

The phytase gene encodes a primary translation product of 467 amino acids (MW 51091); processing of the primary translation product by cleaving off the signal peptide results in a mature phytase protein of 444 (MW 48851) or 448 (containing the first four N-terminal amino acids as published by Ullah, MW 49232) amino acids.

Example 9
Overexpression of phytase in Aspergilli by introduction of additional phytase genomic DNA copies
Construction expression vector pAF 2-2S All constructs were made using standard molecular biological procedures, as described by Maniatis et al., (1982) Molecular cloning, A laboratory Manual, Cold Spring Harbor Laboratory, N.Y.

An expression vector pAF 2-2S was made by subcloning the 6 kb PvuII DNA fragment of the phytase genomic clone lambda AF201, into the SmaI-site of pUC19. The derived plasmid was designated pAF 2-2 (FIG. 4). As selection marker for the transformation to Aspergillus, the EcoRI/KpnI DNA fragment of plasmid pGW325 (Wernars K. (1986), Thesis, Agriculture University, Wageningen, The Netherlands) containing the homologous *Aspergillus nidulans* amdS gene, was inserted into the EcoRI/KpnI sites of pAF 2-2. The resulting expression vector was designated pAF 2-2S and is shown in FIG. 9.

A. Overexpression of phytase in *A. ficuum* NRRL 3135.

The plasmid pAF 2-2S was introduced in *A. ficuum* NRRL 3135 using transformation procedures as described by Tilburn, J. et.al.(1983) Gene 26, 205–221 and Kelly, J. & Hynes, M. (1985) EMBO J., 4, 475–479 with the following modifications:

mycelium was grown on Aspergillus minimal medium (Cove, D. (1966) Biochem. Biophys. Acta, 113, 51–56) supplemented with 10 mM arginine and 10 mM proline for 16 hours at 30° C. in a rotary shaker at 300 rpm;
only Novozym 234 (NOVO Industri), and no helicase, was used for formation of protoplasts;
after 90 minutes of protoplast formation, 1 volume of STC buffer (1.2M sorbitol, 10 mM Tris-HCl pH 7.5, 50 mM $CaCl_2$) was added to the protoplast suspension and centrifuged at 2500 g at 4° C. for 10 minutes in a swinging-bucket rotor. The protoplasts were washed and resuspended in STC-buffer at a concentration of $10^8$ cells/ml plasmid DNA was added in a volume of 10 μl in TE buffer (10 mM Tris-HCl pH 7.5, 0.1 mM EDTA) to 100 μl of the protoplast suspension;
after incubation of the DNA-protoplast suspension at 0° C. for 25 minutes, 200 μl of PEG solution was added dropwise (25% PEG 4000 (Merck), 10 mM Tris-HCl pH 7.5, 50 mM $CaCl_2$). Subsequently, 1 ml of PEG solution (60% PEG 4000 in 10 mM Tris-HCl pH 7.5, 50 mM $CaCl_2$) was added slowly, with repeated mixing of the tubes. After incubation at room temperature, the suspensions were diluted with STC-buffer, mixed by inversion and centrifuged at 2000 g at 4° C. for 10 minutes. The protoplasts were resuspended gently in 200 μl STC-buffer and plated on Aspergillus minimal medium with 10 mM acetamide as the sole nitrogen source, 15 mM CsCl, 1M sucrose, solidified with 0.75% bacteriological agar #1 (Oxoid). Growth was performed at 33° C. for 6–10 days.

Single transformants designated SP4, SP7 and SP8 were isolated, purified and tested for phytase production in shake flasks, using the process as described in Examples 1 and 2. As a control, transformants possessing only the vector (amdS gene in pUC19), as well as the untransformed host were tested.

Strains were grown under induced conditions (see Example 6) and samples were taken after 96 hours of growth. Analyses were performed by measuring the phytase activity (Table 4) and by isoelectric focusing polyacrylamide gelelectrophoresis (IEF-PAGE).

Samples of equal volume were taken from fermentations of *A. ficuum* and *A. ficuum* pAF 2-2S SP7, grown under identical conditions, and were applied onto an IEF-PAGE gel (pH-range 4.5-6, Phast-System, Pharmacia). The electrophoresis was performed according to the instructions of the manufacturer. Subsequently, the gels were either stained with the general protein stain Coomassie Briliant Blue (FIG. 10B), or with the general phosphatase activity staining described in Example 2 (FIG. 10A).

A sample of *A. ficuum* phytase, purified to homogeneity (via immunoaffinity chromatography as described in Example 7), was also applied either alone, or mixed with a culture supernatant.

Phytase is present in the various samples in a number of isoforms (indicated with an asterisk), as has been mentioned in this invention. The two major isoenzymes are clearly visible in the purified phytase in lanes 3 and 4 with both staining procedures (A and B). The phytase bands are barely visible in the parent *A. ficuum* strain, and significantly increased in the pAF 2-2S SP7 transformant strain.

TABLE 4

Increase of phytase production by transformation of *A. ficuum* NRRL 3135.

| Strain | Phytase activity (U/ml) |
| --- | --- |
| A. ficuum | 0.6 |
| A. ficuum + control plasmid | 0.6 |
| A. ficuum pAF 2-2S SP8 | 7.6 |
| A. ficuum pAF 2-2S SP7 | 6.7 |
| A. ficuum pAF 2-2S SP4 | 4.3 |

B. Overexpression of phytase in *A. niger* CBS 513.88.

The expression vector pAF 2-2S was also introduced in *A. niger* CBS 513.88 by transformation procedures as described for *A. ficuum*. Single transformants were isolated, purified and tested for phytase production in shake flasks under induced growth conditions as described in Example 6.

Phytase expression levels of some transformants (designated as A. niger pAF 2-2S #8, #20 and #33) and control strains were performed as described in Example 9A and are shown in Table 5.

A. niger transformants have phytase expression levels comparable with A. ficuum transformants. In addition this result indicates that the A. ficuum phytase promoter is active in A. niger.

Further analysis was performed on culture medium of transformant pAF 2-2S #8 by electrophoresis on an IEF-PAGE gel in the pH range of 4.5-6 on a Phast-System (Pharmacia) as described above. Equal volumes of the culture supernatants of the A. niger parent strain and of the transformant pAF 2-2S #8, grown under identical conditions, were applied onto the gel. The gels were run and subsequently stained as above.

The parent A. niger produces a very low amount of phytase, which could not be detected by gel electrophoresis. The strain pAF 2-2S #8 produces approx. 90 times more phytase, and this difference is clearly visible in FIG. 11.

Several isoforms of the phytase enzyme are detected (indicated by asterisk). The general protein stain indicates that the intensity of the phytase protein bands is dramatically increased, while no other major protein bands appear.

TABLE 5

Phytase production by transformation of A. niger CBS 513.88 with pAF 2-2S.

| Strain | Phytase activity (U/ml) |
| --- | --- |
| A. niger | 0.2 |
| A. niger + control plasmid | 0.2 |
| A. niger pAF 2-2S # 8 | 14 |
| A. niger pAF 2-2S # 33 | 5 |
| A. niger pAF 2-2S # 20 | 4 |

Example 10

Phytase expression in A. niger transformed with expression vectors containing the A. ficuum phytase gene fused to the promoter and/or signal sequences of the A. niger amyloglucosidase (AG) gene.

Constructions of the expression vectors

To obtain overexpression of phytase in A. niger, additional expression cassettes are derived in which the A. ficuum phytase gene is under control of the A. niger amyloglucosidase (AG) promoter in combination with different signal sequences. In p18FYT3 and p24FYT3 the respective 18 and 24 amino acid (aa) leader sequences of the AG gene from A. niger are fused to the phytase gene fragment encoding the mature protein. In the expression cassette pFYT3 the AG promoter sequence is fused to the phytase encoding sequence including the phytase leader sequence.

Construction of p18FYT3

Fusion of the AG-promoter and the 18 aa AG-leader sequence to the phytase sequence encoding the mature protein were performed by the Polymerase Chain Reaction method. In the PCR reactions two different templates were used: pAF 2-2S containing the entire phytase gene as described above and pAB6-1, a plasmid which contains the entire AG-locus from A. niger, which was isolated from a A. niger plasmid library, containing 13-15-kb HindIII fragments in pUC19. For the isolation, AG-specific oligos were used:

AG-1: 5'-GACAATGGCTACACCAGCACCGCAACGGA CATTGTTTGGCCC-3'(SEQ ID NO:38)
AG-2: 5'-AAGCAGCCATTGCCCGAAGCCGAT-3'(SEQ ID NO:39) both based on the nucleotide sequence published for A. niger (Boel et al.(1984), EMBO J. 3, 1097–1102; Boel et al.(1984), Mol. and Cell. Biol. 4, 2306–2315). The oligonucleotide probes were derived from the sequence surrounding intron 2: oligo AG-1 is located 3'of the intron and has a polarity identical to the AG mRNA and oligo AG-2 is found upstream of intron 2 and is chosen antiparallel to the AG mRNA. Plasmid pAB6-1 contains the AG gene on a 14.5 kb HindIII fragment (see FIG. 12).

As primers for the PCR-amplifications four synthetic oligonucleotides were designed with the following sequence:

Oligo 1: 5'-CTCTGCAGGAATTCAAGCTAG-3'(SEQ ID NO:40) (an AG-specific sequence around the EcoRI site approx. 250 bp upstream the ATG initiation codon).

Oligo 18-2: 5'-CGAGGCGGGGACTGCCAGTGCCA ACCCTGTGCAGAC-3'(SEQ ID NO:41) mature phytase <⊥>18 AA AG-leader Oligo 18-3: 5'-GTCTGCACAGGGTTGGCACTGGCAG TCCCCGCCTCG-3'(SEQ ID NO:42) 18 aa AG-leader <⊥>mature phytase Oligo 4: 5'-GGCACGAGGATCCTTCAGCTT-3'(SEQ ID NO:43) (a phytase specific sequence located at the BamHI site on position 861)

The PCR was performed as described by Saiki et al. (1988), Science 239, 487–491, with minor modifications (see Example 8).

To fuse the AG sequences to the phytase coding sequences two separate PCR's were carried out: the first reaction with pAB6-1 as template and oligos 1 and 18-2 as primers to amplify a 300 bp DNA fragment containing the 3'-part of the AG promoter and the 18 aa AG-leader sequence flanked at the 3'-border by the nucleotides of the phytase gene, and the second reaction with pAF 2-2S as template and oligos 18-3 and 4 as primers to amplify a 600 bp DNA fragment containing the 5' part of the phytase gene flanked at the 5'-border by 18 nucleotides of the AG signal peptide. A schematic view of these amplifications is presented in FIG. 13.

The two DNA fragments generated were purified by gelelectrophoresis and ethanol precipitation and used as templates in the third PCR with oligos 1 and 4 as primers to generate the AG-phytase fusion. The obtained DNA fragment was digested with EcoR1 and BamHI and subcloned into pTZ18R. The resulted fusion was sequenced and designated p18FYT1.

The remaining (3.5 Kb) upstream region of the AG-promoter was obtained by digestion of pAB6-1 with Kpn1 and partially with EcoR1 and ligated to the 1.1 Kb EcoR1/BamHI fragment of p18FYT1 and subsequently cloned into the Kpn1-/BamHI sites of pTZ18R. Plasmid p18FYT2 thus obtained is shown in FIG. 15.

An additional HindIII restriction site was introduced by insertion of the synthetic fragment:

5'AATTCAAGCTTG 3'(SEQ ID NO:44)
3'GTTCGAACTTAA 5'(SEQ ID NO:44)

into the EcoRI-site (flanking the amds-gene) of pAF 2-2S. The obtained plasmid was designated pAF 2-2SH (FIG. 14) and is used as starting plasmid to exchange the phytase promoter sequences by the PCR AG-phytase fusion DNA fragments.

For the final construction, p18FYT2 and pAF 2-2SH were digested with KpnI and partially with BamHI. The 4.6 kb DNA fragment of p18FYT2 and the 11 kb DNA fragment of pAF 2-2SH were isolated and purified by gel electrophoresis, subsequently ligated and transferred to E. coli. The derived expression cassette was designated p18FYT3 (FIG. 15).

Construction of p24FYT3

Fusion of the AG-promoter and the 24 aa AG leader sequence to the mature phytase encoding sequence was performed by PCR-amplification as described above for the construction for p18FYT3 with the exception of the primers used. Two new primers were synthesized with the following sequence:

Oligo 24-2: 5'-CGAGCCGGGGACTGCCAGGCGCTTG GAAATCACATT-3'(SEQ ID NO:45) mature phytase <⊥>24 AA AG-leader Oligo 24-3: 5'-AATGTGATTTCCAAGCGCCTGGCAGT CCCCGCCTCG-3'(SEQ ID NO:46) 24 aa AG-leader <⊥>mature phytase Two separate PCR's were carried out: the first reaction with pAB 6-1 as template and oligos 1 and 24-2 as primers to amplify a 318 bp DNA fragment containing the 3'-part of the AG promoter and the 24 aa AG leader sequence flanked at the 3'-border by 18 nucleotides of the phytase gene and the second reaction with pAF 2-2S as template and oligos 24-3 and 4 as primers to amplify a DNA fragment containing the 5'-part of the phytase gene flanked at the 5'-border by 18 nucleotides of the 24 aa AG leader. A schematic view of these amplifications is presented in FIG. 13.

For the construction of the final expression cassette p24FYT3 via the intermediate plasmids p24FYT1 and p24FYT2, the same cloning pathway/procedure was used-as described for p18FYT1 and p18FYT2 to derive the expression cassette p18FYT3 (FIG. 15).

Construction of pFYT3

Fusion of the AG-promoter to the phytase gene (including the phytase leader) sequence was also performed by PCR-amplification as described above for the construction of p18FYT3 with the exception of the primers used. Two additional primers were generated with the following sequence:

Oligo fyt-2: 5'-AACAGCAGAGACGCCCATTGCTGA GGTGTAATGATG-3'(SEQ ID NO:47) phytase leader <⊥>AG-promoter Oligo fyt-3: 5'-CATCATTACACCTCAGCAATGGGCG TCTCTGCTGTT-3'(SEQ ID NO:48) AG-promoter <⊥>phytase leader Two separate PCR's were carried out: the first reaction with pAB 6-1 as template and oligos 1 and fyt-2 as primers to amplify a 282 bp DNA fragment containing the 3'-part of the AG promoter flanked at the 3'-border by 18 nucleotides of the phytase leader and the second reaction with pAF 2-2S as template and oligos fyt-3 and 4 as primers to amplify a DNA-fragment containing the 5'-part of the phytase gene (including the phytase leader) and flanked at the 5'-border by 18 nucleotides of the AG-promoter. A schematic view of these amplifications is presented in FIG. 13.

For the construction of the final expression cassette pFYT3 along the intermediate plasmids pFYT1 and pFYT2, the same cloning pathway/procedure was used as described for p18FYT1 and p18FYT2 to derive the expression cassette p18FYT3 (FIG. 15).

Expression of the phytase gene under the control of the AG promoter in A. niger

E. coli sequences were removed from the phytase expression cassettes described above by HindIII digestion. Afterwards, the A. niger strain CBS 513.88 (deposited Oct. 10, 1988) was transformed with 10 μg DNA fragment by procedures as described in Example 9. Single A. niger transformants from each expression cassette were isolated, and spores were streaked on selective acetamide-agar plates. Spores of each transformant were collected from cells grown for 3 days at 37° C. on 0.4% potato-dextrose (Oxoid, England) agar plates. Phytase production was tested in shake flasks under the following growth conditions:

Approximately 1×108 spores were inoculated in 100 ml pre-culture medium containing (per liter): 1 g $KH_2PO_4$; 30 g maltose; 5 g yeast-extract; 10 g casein-hydrolysate; 0.5 g $MgSO_4 \cdot 7H_2O$ and 3 g Tween 80. The pH was adjusted to 5.5.

After growing overnight at 34° C. in a rotary shaker, 1 ml of the growing culture was inoculated in a 100 ml main-culture containing (per liter): 2 g $KH_2PO_4$; 70 g malto-dextrin (Maldex $MDO_3$, Amylum); 12.5 g yeast-extract; 25 g casein-hydrolysate; 2 g $K_2SO_4$; 0.5 g $MgSO_4 \cdot 7H_2O$; 0.03 g $ZnCl_2$; 0.02 g $CaCl_2$; 0.05 g $MnSO_4 \cdot 4 H_2O$ and $FeSO_4$. The pH was adjusted to 5.6.

The mycelium was grown for at least 140 hours. Phytase production was measured as described in Example 2. The production results of several, random transformants obtained from each expression cassette are shown in Table 6.

TABLE 6

Phytase production of several A. niger CBS 513.88 strains transformed with plasmids containing the A. ficuum phytase gene under control of the A. niger AG-promoter in combination with different leader sequences.

| Expression cassette | Transformant # | Phytase activity (U/ml) |
|---|---|---|
| p18FYT3 (AG-promoter/ 18 aa AG-leader) | p18FYT3 # 240 | 82 |
| | p18FYT3 # 242 | 84 |
| | p18FYT3 # 243 | 62 |
| | p18FYT3 # 244 | 43 |
| | p18FYT3 # 245 | 80 |
| | p18FYT3 # 246 | 82 |
| | p18FYT3 # 250 | 110 |
| p24FYT3 (AG-promoter/ 24 aa AG-leader) | p24FYT3 # 256 | 8 |
| | p24FYT3 # 257 | 30 |
| | p24FYT3 # 258 | 13 |
| | p24FYT3 # 259 | 33 |
| | p24FYT3 # 260 | 17 |
| | p24FYT3 # 261 | 28 |
| | p24FYT3 # 262 | 18 |
| | p24FYT3 # 265 | 12 |
| pFYT3 (AG-promoter/ phytase leader) | pFYT3 # 205 | 50 |
| | pFYT3 # 282 | 280 |
| | pFYT3 # 299 | 96 |
| | pFYT3 # 302 | 220 |
| | pFYT3 # 303 | 175 |
| | pFYT3 # 304 | 150 |
| | pFYT3 # 305 | 150 |
| | pFYT3 # 312 | 140 |

The data clearly show high phytase expression levels in A. niger transformants containing the phytase gene under the control of the A. niger AG promoter. The data also show that the highest phytase production is obtained with the pFYT3 expression vector, which contains the phytase leader sequence. Similar expression vectors containing an intron-less phytase gene after transformation to A. niger, resulted in phytase expression levels comparable to pFYT3 transformants of A. niger.

In addition, electrophoresis on an IEF-PAGE gel in the pH-range of 4.5–6 was performed on culture supernatants of transformants pFYT3 #205 and #282. Equal volumes of the culture supernatants of the A. niger parent strain and of both transformants, grown under identical conditions, were applied onto the gel, run and subsequently stained as described in Example 9. The parent A. niger produces a very low amount of phytase, which is not detected in this experiment. The strains pFYT3 #205 and #282 produce approx. 250 and 1400 times more phytase (compare phytase levels in Tables 4 and 5), and this difference is clearly visible in FIG. 11. Several isoforms of the phytase enzyme are detected (indicated by an asterisk). The general protein stain indicates that the intensity of the phytase protein bands is dramatically increased, while no other major protein bands appear.

Example 11 overexpression of phytase in A. ficuum and A. niger grown on an industrial scale A. A. ficuum Strain A. ficuum pAF 2-2S #4 and A. ficuum NRRL 3135 were grown as described in Example 1. The transformant produced approximately 50 times more phytase as compared to the wild-type strain.

TABLE 7

Overexpression of phytase by a transformant of A. ficuum containing multiple phytase genes. Cells were grown as described in Example 1.

| Hours after inoculation | Phytase activity A. ficuum NRRL 3135 | (U/ml Fermentation broth) A. ficuum pAF 2-2S #4 |
|---|---|---|
| 0 | 0 | 0 |
| 24 | 0 | 0 |
| 92 | 2 | 142 |
| 141 | 5 | 270 |

B. A. niger

Strain A. niger pAF 2-2S #8, a transformant of A. niger strain CBS 513.88 and the parent A. niger strain itself were grown as described in Example 1. The transformant produced approximately 1000 times more phytase as compared to the original A. niger parent strain (Table 8).

TABLE 8

Overexpression of phytase by a transformant of A. niger (CBS 513.88) containing multiple phytase genes. Cells were grown as described in Example 1.

| Hours after inoculation | Phytase activity A. niger CBS 513.88 | (U/ml fermentation broth) A. niger pAF 2.2 #8 |
|---|---|---|
| 0 | 0 | 0 |
| 24 | 0 | 5 |
| 92 | 0.1 | 65 |
| 141 | 0.1 | 95 |

Example 12

To construct the vector pREPFYT3, with which simultaneously phytase expression and AG gene replacement is achieved, pFYT3 is digested with KpnI. With the obtained linear KpnI DNA fragment, two separate ligations are performed.

Ligation 1 with the KpnI-HindIII adaptor:

5'-         CGGGGA       -3'
3'-CATGGCCCCTTCGA-5'
     KpnI         HindIII (SEQ ID NO: 49)

Ligation 2 with the KpnI-HindIII* adaptor, in which the HindIII restriction site will not restore after ligation:

5'-         CGGGGG       -3'
3'-CTAGGCCCCCTCGA-5'
     KpnI         HindIII* (SEQ ID NO: 50)

Subsequently, ligation 1 is partially digested with HindIII. After removal of the amdS containing fragment by gel electrophoresis, the remaining DNA fragment is recircularized by ligation and transferred to E. coli. The obtained plasmid is denoted pFYT3ΔamdS (see FIG. 16).

Ligation 2 is also digested with HindII and the 4 kb DNA HindIII/HindIII* fragment, containing the amdS gene, is isolated by gel electrophoresis, subsequently ligated to a partially HindIII digest of pFYT3ΔamdS and transferred to E.coli. The plasmid containing the amdS gene at the 3'end of the phytase gene is denoted pFYT3INT (see FIG. 17).

To introduce the approx. 6 kb SalI/HindIII DNA fragment of pAB6-1, containing the 3'--flanking AG sequence, pFYT3INT is partially digested with HindIII, ligated first to the adaptor:

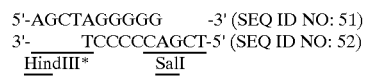

5'-AGCTAGGGGG         -3' (SEQ ID NO: 51)
3'-        TCCCCCAGCT-5' (SEQ ID NO: 52)
   HindIII*        SalI (in which the HindIII* restriction site will not restore after ligation) and subsequently with the SalI/HindIII fragment of pAB6-1. After transformation to E. coli, the desired plasmid pREPFYT3, containing the 3'AG flanking sequence at the correct position, is obtained (FIG. 18).

Expression of phytase in A. niger by AG gene replacement.

Before transformation of A. niger with pREPFYT3, the E. coli sequences in the plasmid are removed by HindIII digestion and gelelectrophoresis. The A. niger strain CBS 513.88 is transformed with 10 μg DNA fragment by procedures as described in Example 9. Selection and growth of transformants is performed as described in Example 9. Only a minority of the selected transformants lose AG activity (approx. 20%). Southern analysis of chromasal DNA is performed on AG negative and phytase positive transformants to verify that the AG gene is indeed replaced by the phytase gene.

Example 13

Conservation of the phytase gene in different species.

To determine whether the phytase gene is highly conserved within microbial species, Southern analyses of chromosomal DNA from ten different species were performed with the A. ficuum phytase cDNA as probe.

These chromosomal DNA analyses were performed on species from filamentous fungi, yeasts and bacteria. As an example, only a limited number from each group were chosen: for filamentous fungi, Penicillium chrysogenum and Aspergillus niger; for yeast, Saccharomyces cerevisiae and Kluyveromyces lactis; and for the procaryotic organisms the Gram-positive species, Bacillus subtilis, Clostridum thermocellum, and Streptomyces lividans and as an example for a gram-negative bacterium Pseudomonas aeruginosa.

High molecular weight chromosomal DNA from these species was digested with PvuII and BamHI separately and subsequently electrophorized on a 0.7% agarose gel.

After transfer to nitrocellulose filters, the hybridization was performed overnight at low stringency (6 ×SSC; 50° C.) with a $^{32}$P-labeled 5'-phytase cDNA fragment (described in Example 8). Blots were washed in 6×SSC at room temperature and exposed to X-ray for 18 hours.

As shown in FIGS. 19 a and b, descrete bands are observed in almost every lane, predicting a high degree of homology of the phytase gene between microbial species.

We claim:

1. An isolated *Aspergillus ficuum* phytase wherein said phytase has an apparent molecular weight of 85 kD and an apparent molecular weight after deglycosylation in the range of about 48–56.5 kD, has a specific activity of about 100 U/mg protein, has a pH optimum at pH 5.5 and is substantially free of *Aspergillus ficuum* acid phosphatase having a molecular weight of 100 kD.

2. A feed for animals wherein said feed is supplemented with the phytase claim 1.

3. The phytase of claim 1 wherein said phytase is isolated from a recombinant host that has altered to contain a nucleic acid molecule that encodes a protein comprising the amino acid sequence of SEQ ID No:32.

4. A feed for animals wherein said feed is supplemented with the phytase of claim 3.

5. An isolated phytase produced by a recombinant host cell comprising a nucleic acid molecule encoding said phytase operably linked to control sequences compatible with said host cell, wherein said nucleic acid molecule is selected from the group consisting of: a nucleic acid molecule that encodes a phytase comprising the amino acid sequence of SEQ ID NO:32; a nucleic acid molecule that comprises the nucleotide sequence of SEQ ID NO:30; and a nucleic acid molecule isolated from a filamentous fungus that hybridizes to nucleotides 210–1129 of SEQ ID NO:30 at 6×SSC; 50° C. overnight.

6. A feed for animals wherein said feed is supplemented with the phytase of claim 5.

7. A method to liberate inorganic phosphate from phytate which method comprises contacting a composition containing said phytate with the phytase of claim 1.

8. A method to liberate inorganic phosphate from phytate which method comprises contacting a composition containing said phytate with the phytase of claim 3.

9. A method to liberate inorganic phosphate from phytate which method comprises contacting a composition containing said phytate with the phytase of claim 5.

10. The phytase of claim 1 wherein said phytase has a second pH optimum at pH 2.5.

* * * * *

UNITED STATES PATENT AND TRADEMARK OFFICE

CERTIFICATE OF CORRECTION

PATENT NO. : 5,863,533

DATED : January 26, 1999

INVENTOR(S) : Van Gorcom *et al.*

It is certified that error appears in the above-identified patent and that said Letters Patent is hereby corrected as shown below:

Claim 5: please change "SEQ ID NO:30", both occurrences, to --SEQ ID NO:31 .--.

Signed and Sealed this

Tenth Day of April, 2001

*Attest:*

NICHOLAS P. GODICI

*Attesting Officer*     Acting Director of the United States Patent and Trademark Office

SEQUENCE LISTING ( 1 ) GENERAL INFORMATION:

( i i i ) NUMBER OF SEQUENCES: 52

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:1:

Gln Ser Ser Xaa Asp Thr Val Asp Gln
    1                5

( 2 ) INFORMATION FOR SEQ ID NO:2:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:2:

Ala Ser Xaa Xaa Gln Ser Ser Xaa Asp Thr Val Asp Gln Gly Tyr Gln
    1               5                    10                   15

Arg Phe Ser Glu Thr Ser His Leu Arg Xaa Gln Tyr Ala Pro Phe Phe
                  20                          25                    30

Asp Leu Ala
               35

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:3:

Val Val Asp Glu Arg Phe Pro Tyr Thr Gly
    1                5                    10

( 2 ) INFORMATION FOR SEQ ID NO:4:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide (iii) HYPOTHETICAL: NO (v) FRAGMENT TYPE: internal (xi) SEQUENCE DESCRIPTION: SEQ ID NO:4:

Gln Xaa Gln Ala Glu Gln Glu Pro Leu Val Arg Val Leu Val Asn Asp
1               5                   10                  15

Arg Val Val Pro
            20

(2) INFORMATION FOR SEQ ID NO:5:

(i) SEQUENCE CHARACTERISTICS:
                (A) LENGTH: 23 amino acids
                (B) TYPE: amino acid
                (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:5:

Xaa Ser Phe Asp Thr Ile Ser Thr Ser Thr Val Asp Thr Lys Leu Ser
1               5                   10                  15

Pro Phe Cys Asp Leu Phe Thr
            20

(2) INFORMATION FOR SEQ ID NO:6:

(i) SEQUENCE CHARACTERISTICS:
                (A) LENGTH: 16 amino acids
                (B) TYPE: amino acid
                (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO:6:

Leu Ala Val Pro Ala Ser Arg Asn Gln Ser Ser Gly Asp Thr Val Asp
1               5                   10                  15

(2) INFORMATION FOR SEQ ID NO:7:

(i) SEQUENCE CHARACTERISTICS:
                (A) LENGTH: 19 amino acids
                (B) TYPE: amino acid
                (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:7:

Met Met Gln Cys Gln Ala Glu Gln Glu Pro Leu Val Arg Val Leu Val
1               5                   10                  15

Asn Asp Arg (2) INFORMATION FOR SEQ ID NO:8:

(i) SEQUENCE CHARACTERISTICS:
                (A) LENGTH: 12 amino acids
                (B) TYPE: amino acid (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:8:

```
Ala  Ser  Ser  Ala  Glu  Lys  Gly  Tyr  Asp  Leu  Val  Val
1                   5                        10
```

(2) INFORMATION FOR SEQ ID NO:9:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:9:

```
Val  Val  Asp  Xaa  Arg  Phe  Pro  Tyr  Thr  Gly  Xaa  Ala
1                   5                        10
```

(2) INFORMATION FOR SEQ ID NO:10:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (ii) MOLECULE TYPE: DNA (iii) HYPOTHETICAL: YES (vi) ORIGINAL SOURCE:
        Phytase N- terminus reverse
        translation (xi) SEQUENCE DESCRIPTION: SEQ ID NO:10:

```
YTNGCNGTNC  CNGCNWSNMG  NAAYCARWSN  WSNGGNGAYA  CNGTNGAYCA  RGGNTAYCAR    60

MGNTTWWWSA  RACNWSNCAW  YTNMGNGGNC  ARTAYGCNCC  NTTYTTYGAY  YTNGCN       116
```

(2) INFORMATION FOR SEQ ID NO:11:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (iii) HYPOTHETICAL: YES (vi) ORIGINAL SOURCE:
        internal fragment A (Phytase)
        reverse translation (xi) SEQUENCE DESCRIPTION: SEQ ID NO:11:

```
CARNNNCARG  CRGANCARGA  RCCRYTNGTN  HSNGTNYTNG  TNRAYVVNVK  NGTNCCNCCN    60

ATGGGN                                                                   66
```

(2) INFORMATION FOR SEQ ID NO:12:

( i ) SEQUENCE CHARACTERISTICS:
    ( A ) LENGTH: 99 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: YES ( v i ) ORIGINAL SOURCE:
    internal fragment B (Phytase)
    reverse translation ( x i ) SEQUENCE DESCRIPTION: SEQ ID NO:12:

TGGWSNTTYG AYACNATHWS NACNWSNACN GTNGAYACNA ARYTNWSNCC NTTYTCYGAY    60

YTNTTYACNA CNGAYGARTG YATHAMNTAY VGNTAYYTN    99

( 2 ) INFORMATION FOR SEQ ID NO:13:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: YES ( v i ) ORIGINAL SOURCE:
        alkaline phosphatase reverse
        translation ( x i ) SEQUENCE DESCRIPTION: SEQ ID NO:13:

TTYWSNTAYG GNGCNGCNAT HCCNCARWSN ACNCARGARA ARCARTTYWS NCARGARTTY    60

MGNGAYGGN    69

( 2 ) INFORMATION FOR SEQ ID NO:14:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( v i ) ORIGINAL SOURCE:
        AB1024

( x i ) SEQUENCE DESCRIPTION: SEQ ID NO:14:

CTGGTCGACG GTGTCGCCGC TGCTCTGGTT GCGGCTGGCG GGACGGC    48

( 2 ) INFORMATION FOR SEQ ID NO:15:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( v i ) ORIGINAL SOURCE:
        AB1065

(x i) SEQUENCE DESCRIPTION: SEQ ID NO:15:

CTGRTCCACG GTGTCGCC                                                                 18

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (synthetic)

(i i i) HYPOTHETICAL: NO (v i) ORIGINAL SOURCE:
            AB1066

(x i) SEQUENCE DESCRIPTION: SEQ ID NO:16:

CTGRTCGACG GTGTCGCC                                                                 18

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (synthetic)

(i i i) HYPOTHETICAL: NO (v i) ORIGINAL SOURCE:
            AB1067

(x i) SEQUENCE DESCRIPTION: SEQ ID NO:17:

CTGRTCCACA GTGTCGCC                                                                 18

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (synthetic)

(i i i) HYPOTHETICAL: NO (v i) ORIGINAL SOURCE:
            AB1069

(x i) SEQUENCE DESCRIPTION: SEQ ID NO:18:

CTGRTCCACG GTATCGCC                                                                 18

(2) INFORMATION FOR SEQ ID NO:19:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (synthetic)

(i i i) HYPOTHETICAL: NO (v i) ORIGINAL SOURCE:
            AB1069

( x i ) SEQUENCE DESCRIPTION: SEQ ID NO:19:

CTGGTCCACG GTGTCACC 18

( 2 ) INFORMATION FOR SEQ ID NO:20:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( v i ) ORIGINAL SOURCE:
        AB1070

( x i ) SEQUENCE DESCRIPTION: SEQ ID NO:20:

CTGATCGACA GTATCACC 18

( 2 ) INFORMATION FOR SEQ ID NO:21:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( v i ) ORIGINAL SOURCE:
        AB1226

( x i ) SEQUENCE DESCRIPTION: SEQ ID NO:21:

CTGGTARCCC TGRTCSAC 18

( 2 ) INFORMATION FOR SEQ ID NO:22:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( v i ) ORIGINAL SOURCE:
        AB1227

( x i ) SEQUENCE DESCRIPTION: SEQ ID NO:22:

YTGRTADCCY TGRTCVAC 18

( 2 ) INFORMATION FOR SEQ ID NO:23:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( v i ) ORIGINAL SOURCE:
        AB1298

( x i ) SEQUENCE DESCRIPTION: SEQ ID NO:23:

YTGRTASCCK TGRTCSACSG TRTC 24

( 2 ) INFORMATION FOR SEQ ID NO:24:

( i ) SEQUENCE CHARACTERISTICS:
  ( A ) LENGTH: 26 base pairs
  ( B ) TYPE: nucleic acid
  ( C ) STRANDEDNESS: single
  ( D ) TOPOLOGY: linear ( i i ) MOLECULE TYPE: DNA (synthetic)

( i i i ) HYPOTHETICAL: NO ( v i ) ORIGINAL SOURCE:
  AB1388

( x i ) SEQUENCE DESCRIPTION: SEQ ID NO:24:

ARGTCGAAGA ASGGSGCGTA CTGSCC 26

( 2 ) INFORMATION FOR SEQ ID NO:25:

( i ) SEQUENCE CHARACTERISTICS:
  ( A ) LENGTH: 23 base pairs
  ( B ) TYPE: nucleic acid
  ( C ) STRANDEDNESS: single
  ( D ) TOPOLOGY: linear ( i i ) MOLECULE TYPE: DNA (synthetic)

( i i i ) HYPOTHETICAL: NO ( v i ) ORIGINAL SOURCE:
  AB1295

( x i ) SEQUENCE DESCRIPTION: SEQ ID NO:25:

ACSARSGGYT CYTGYTCSGC YTG 23

( 2 ) INFORMATION FOR SEQ ID NO:26:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( i i ) MOLECULE TYPE: DNA (synthetic)

( i i i ) HYPOTHETICAL: NO ( v i ) ORIGINAL SOURCE:
  AB1296

( x i ) SEQUENCE DESCRIPTION: SEQ ID NO:26:

CTTCGTGTCC ACSGTSSWSG TSSWGATCGT GTCGAA 36

( 2 ) INFORMATION FOR SEQ ID NO:27:

( i ) SEQUENCE CHARACTERISTICS:
  ( A ) LENGTH: 37 base pairs
  ( B ) TYPE: nucleic acid
  ( C ) STRANDEDNESS: single
  ( D ) TOPOLOGY: linear ( i i ) MOLECULE TYPE: DNA (synthetic)

( i i i ) HYPOTHETICAL: NO ( v i ) ORIGINAL SOURCE:
  AB1297

( x i ) SEQUENCE DESCRIPTION: SEQ ID NO:27:

TGATGCACTC GTCSGTSGTG AASAGGTCGC AGAASGG 37

( 2 ) INFORMATION FOR SEQ ID NO:28:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( v i ) ORIGINAL SOURCE:
        AB1025

( x i ) SEQUENCE DESCRIPTION: SEQ ID NO:28:

CGGAACTCCT GGCTGAACTG CTTCTCCTGG GTGCTCTGGG GGATGGCGGC GCCGTA 56

( 2 ) INFORMATION FOR SEQ ID NO:29:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( v i ) ORIGINAL SOURCE:
        AB1026

( x i ) SEQUENCE DESCRIPTION: SEQ ID NO:29:

CGGAAYTCCT GVSWGAACTG CTTYTCCTG 29

( 2 ) INFORMATION FOR SEQ ID NO:30:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( v i ) ORIGINAL SOURCE:
        AB1027

( x i ) SEQUENCE DESCRIPTION: SEQ ID NO:30:

CTGSGGRATN GCNCGRCCGT A 21

( 2 ) INFORMATION FOR SEQ ID NO:31:

( i ) SEQUENCE CHARACTERISTICS:
        ( A ) LENGTH: 6756 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:

(A) ORGANISM: Aspergillus ficuum (Aspergillus niger)
                (B) STRAIN: NRRL 3135

(vii) IMMEDIATE SOURCE:
                (A) LIBRARY: lambda AF
                (B) CLONE: pAF2-3, pAF2-6, pAF2-7

(ix) FEATURE:
                (A) NAME/KEY: exon
                (B) LOCATION: 210..253

(ix) FEATURE:
                (A) NAME/KEY: intron
                (B) LOCATION: 254..355

(ix) FEATURE:
                (A) NAME/KEY: exon
                (B) LOCATION: 356..1715

(ix) FEATURE:
                (A) NAME/KEY: CDS
                (B) LOCATION: join(210..253, 356..1715)
                (D) OTHER INFORMATION: /codon_start= 210
                        / product= "Phytase"

(ix) FEATURE:
                (A) NAME/KEY: sig_peptide
                (B) LOCATION: 210..380

(ix) FEATURE:
                (A) NAME/KEY: mat_peptide
                (B) LOCATION: 381..1712
                (C) IDENTIFICATION METHOD: experimental
                (D) OTHER INFORMATION: /function="inositol phosphate
                        phosphatase"
                        / product= "Phytase"
                        / evidence= EXPERIMENTAL (xi) SEQUENCE DESCRIPTION: SEQ ID NO:31:

```
GTCGACTTCC  CGTCCTATTC  GGCCTCGTCC  GCTGAAGATC  CATCCCACCA  TTGCACGTGG         60

GCCACCTTTG  TGAGCTTCTA  ACCTGAACTG  GTAGAGTATC  ACACACCATG  CCAAGGTGGG        120

ATGAAGGGGT  TATATGAGAC  CGTCCGGTCC  GGCGCGATGG  CCGTAGCTGC  CACTCGCTGC        180

TGTGCAAGAA  ATTACTTCTC  ATAGGCATC   ATG  GGC  GTC  TCT  GCT  GTT  CTA  CTT   233
                                    Met  Gly  Val  Ser  Ala  Val  Leu  Leu
                                    -23             -20

CCT  TTG  TAT  CTC  CTG  TCT  GG    GTATGCTAAG  CACCACAATC  AAAGTCTAAT        283
Pro  Leu  Tyr  Leu  Leu  Ser  Gly
-15                 -10

AAGGACCCTC  CCTTCCGAGG  GCCCCTGAAG  CTCGGACTGT  GTGGGACTAC  TGATCGCTGA        343

CTATCTGTGC  AG  A  GTC  ACC  TCC  GGA  CTG  GCA  GTC  CCC  GCC  TCG  AGA  AAT  392
               Val  Thr  Ser  Gly  Leu  Ala  Val  Pro  Ala  Ser  Arg  Asn
               -8             -5                       1

CAA  TCC  AGT  TGC  GAT  ACG  GTC  GAT  CAG  GGG  TAT  CAA  TGC  TTC  TCC  GAG   440
Gln  Ser  Ser  Cys  Asp  Thr  Val  Asp  Gln  Gly  Tyr  Gln  Cys  Phe  Ser  Glu
5                        10                      15                       20

ACT  TCG  CAT  CTT  TGG  GGT  CAA  TAC  GCA  CCG  TTC  TTC  TCT  CTG  GCA  AAC   488
Thr  Ser  His  Leu  Trp  Gly  Gln  Tyr  Ala  Pro  Phe  Phe  Ser  Leu  Ala  Asn
                    25                      30                           35

GAA  TCG  GTC  ATC  TCC  CCT  GAG  GTG  CCC  GCC  GGA  TGC  AGA  GTC  ACT  TTC   536
Glu  Ser  Val  Ile  Ser  Pro  Glu  Val  Pro  Ala  Gly  Cys  Arg  Val  Thr  Phe
               40                       45                           50

GCT  CAG  GTC  CTC  TCC  CGT  CAT  GGA  GCG  CGG  TAT  CCG  ACC  GAC  TCC  AAG   584
Ala  Gln  Val  Leu  Ser  Arg  His  Gly  Ala  Arg  Tyr  Pro  Thr  Asp  Ser  Lys
          55                       60                           65

GGC  AAG  AAA  TAC  TCC  GCT  CTC  ATT  GAG  GAG  ATC  CAG  CAG  AAC  GCG  ACC   632
Gly  Lys  Lys  Tyr  Ser  Ala  Leu  Ile  Glu  Glu  Ile  Gln  Gln  Asn  Ala  Thr
70                       75                           80
```

| | | | | | | | | | | | | | | | | |
|---|---|---|---|---|---|---|---|---|---|---|---|---|---|---|---|---|
| ACC | TTT | GAC | GGA | AAA | TAT | GCC | TTC | CTG | AAG | ACA | TAC | AAC | TAC | AGC | TTG | 680 |
| Thr | Phe | Asp | Gly | Lys | Tyr | Ala | Phe | Leu | Lys | Thr | Tyr | Asn | Tyr | Ser | Leu | |
| 85 | | | | 90 | | | | | 95 | | | | | | 100 | |
| GGT | GCA | GAT | GAC | CTG | ACT | CCC | TTC | GGA | GAA | CAG | GAG | CTA | GTC | AAC | TCC | 728 |
| Gly | Ala | Asp | Asp | Leu | Thr | Pro | Phe | Gly | Glu | Gln | Glu | Leu | Val | Asn | Ser | |
| | | | | 105 | | | | | 110 | | | | | 115 | | |
| GGC | ATC | AAG | TTC | TAC | CAG | CGG | TAC | GAA | TCG | CTC | ACA | AGG | AAC | ATC | GTT | 776 |
| Gly | Ile | Lys | Phe | Tyr | Gln | Arg | Tyr | Glu | Ser | Leu | Thr | Arg | Asn | Ile | Val | |
| | | | 120 | | | | | 125 | | | | | 130 | | | |
| CCA | TTC | ATC | CGA | TCC | TCT | GGC | TCC | AGC | CGC | GTG | ATC | GCC | TCC | GGC | AAG | 824 |
| Pro | Phe | Ile | Arg | Ser | Ser | Gly | Ser | Ser | Arg | Val | Ile | Ala | Ser | Gly | Lys | |
| | | 135 | | | | | 140 | | | | | 145 | | | | |
| AAA | TTC | ATC | GAG | GGC | TTC | CAG | AGC | ACC | AAG | CTG | AAG | GAT | CCT | CGT | GCC | 872 |
| Lys | Phe | Ile | Glu | Gly | Phe | Gln | Ser | Thr | Lys | Leu | Lys | Asp | Pro | Arg | Ala | |
| | 150 | | | | | 155 | | | | | 160 | | | | | |
| CAG | CCC | GGC | CAA | TCG | TCG | CCC | AAG | ATC | GAC | GTG | GTC | ATT | TCC | GAG | GCC | 920 |
| Gln | Pro | Gly | Gln | Ser | Ser | Pro | Lys | Ile | Asp | Val | Val | Ile | Ser | Glu | Ala | |
| 165 | | | | | 170 | | | | | 175 | | | | | 180 | |
| AGC | TCA | TCC | AAC | AAC | ACT | CTC | GAC | CCA | GGC | ACC | TGC | ACT | GTC | TTC | GAA | 968 |
| Ser | Ser | Ser | Asn | Asn | Thr | Leu | Asp | Pro | Gly | Thr | Cys | Thr | Val | Phe | Glu | |
| | | | | 185 | | | | | 190 | | | | | 195 | | |
| GAC | AGC | GAA | TTG | GCC | GAT | ACC | GTC | GAA | GCC | AAT | TTC | ACC | GCC | ACG | TTC | 1016 |
| Asp | Ser | Glu | Leu | Ala | Asp | Thr | Val | Glu | Ala | Asn | Phe | Thr | Ala | Thr | Phe | |
| | | | 200 | | | | | 205 | | | | | 210 | | | |
| GTC | CCC | TCC | ATT | CGT | CAA | CGT | CTG | GAG | AAC | GAC | CTG | TCC | GGT | GTG | ACT | 1064 |
| Val | Pro | Ser | Ile | Arg | Gln | Arg | Leu | Glu | Asn | Asp | Leu | Ser | Gly | Val | Thr | |
| | | 215 | | | | | 220 | | | | | 225 | | | | |
| CTC | ACA | GAC | ACA | GAA | GTG | ACC | TAC | CTC | ATG | GAC | ATG | TGC | TCC | TTC | GAC | 1112 |
| Leu | Thr | Asp | Thr | Glu | Val | Thr | Tyr | Leu | Met | Asp | Met | Cys | Ser | Phe | Asp | |
| | 230 | | | | | 235 | | | | | 240 | | | | | |
| ACC | ATC | TCC | ACC | AGC | ACC | GTC | GAC | ACC | AAG | CTG | TCC | CCC | TTC | TGT | GAC | 1160 |
| Thr | Ile | Ser | Thr | Ser | Thr | Val | Asp | Thr | Lys | Leu | Ser | Pro | Phe | Cys | Asp | |
| 245 | | | | | 250 | | | | | 255 | | | | | 260 | |
| CTG | TTC | ACC | CAT | GAC | GAA | TGG | ATC | AAC | TAC | GAC | TAC | CTC | CAG | TCC | TTG | 1208 |
| Leu | Phe | Thr | His | Asp | Glu | Trp | Ile | Asn | Tyr | Asp | Tyr | Leu | Gln | Ser | Leu | |
| | | | | 265 | | | | | 270 | | | | | 275 | | |
| AAA | AAG | TAT | TAC | GGC | CAT | GGT | GCA | GGT | AAC | CCG | CTC | GGC | CCG | ACC | CAG | 1256 |
| Lys | Lys | Tyr | Tyr | Gly | His | Gly | Ala | Gly | Asn | Pro | Leu | Gly | Pro | Thr | Gln | |
| | | | 280 | | | | | 285 | | | | | 290 | | | |
| GGC | GTC | GGC | TAC | GCT | AAC | GAG | CTC | ATC | GCC | CGT | CTG | ACC | CAC | TCG | CCT | 1304 |
| Gly | Val | Gly | Tyr | Ala | Asn | Glu | Leu | Ile | Ala | Arg | Leu | Thr | His | Ser | Pro | |
| | | 295 | | | | | 300 | | | | | 305 | | | | |
| GTC | CAC | GAT | GAC | ACC | AGT | TCC | AAC | CAC | ACT | TTG | GAC | TCG | AGC | CCG | GCT | 1352 |
| Val | His | Asp | Asp | Thr | Ser | Ser | Asn | His | Thr | Leu | Asp | Ser | Ser | Pro | Ala | |
| | 310 | | | | | 315 | | | | | 320 | | | | | |
| ACC | TTT | CCG | CTC | AAC | TCT | ACT | CTC | TAC | GCG | GAC | TTT | TCG | CAT | GAC | AAC | 1400 |
| Thr | Phe | Pro | Leu | Asn | Ser | Thr | Leu | Tyr | Ala | Asp | Phe | Ser | His | Asp | Asn | |
| 325 | | | | | 330 | | | | | 335 | | | | | 340 | |
| GGC | ATC | ATC | TCC | ATT | CTC | TTT | GCT | TTA | GGT | CTG | TAC | AAC | GGC | ACT | AAG | 1448 |
| Gly | Ile | Ile | Ser | Ile | Leu | Phe | Ala | Leu | Gly | Leu | Tyr | Asn | Gly | Thr | Lys | |
| | | | | 345 | | | | | 350 | | | | | 355 | | |
| CCG | CTA | TCT | ACC | ACG | ACC | GTG | GAG | AAT | ATC | ACC | CAG | ACA | GAT | GGA | TTC | 1496 |
| Pro | Leu | Ser | Thr | Thr | Thr | Val | Glu | Asn | Ile | Thr | Gln | Thr | Asp | Gly | Phe | |
| | | | 360 | | | | | 365 | | | | | 370 | | | |
| TCG | TCT | GCT | TGG | ACG | GTT | CCG | TTT | GCT | TCG | CGT | TTG | TAC | GTC | GAG | ATG | 1544 |
| Ser | Ser | Ala | Trp | Thr | Val | Pro | Phe | Ala | Ser | Arg | Leu | Tyr | Val | Glu | Met | |
| | | 375 | | | | | 380 | | | | | 385 | | | | |
| ATG | CAG | TGT | CAG | GCG | GAG | CAG | GAG | CCG | CTG | GTC | CGT | GTC | TTG | GTT | AAT | 1592 |
| Met | Gln | Cys | Gln | Ala | Glu | Gln | Glu | Pro | Leu | Val | Arg | Val | Leu | Val | Asn | |
| | 390 | | | | | 395 | | | | | 400 | | | | | |

| | | | | | | | | | | | | | | | | |
|---|---|---|---|---|---|---|---|---|---|---|---|---|---|---|---|---|
| GAT | CGC | GTT | GTC | CCG | CTG | CAT | GGG | TGT | CCG | GTT | GAT | GCT | TTG | GGG | AGA | 1640 |
| Asp | Arg | Val | Val | Pro | Leu | His | Gly | Cys | Pro | Val | Asp | Ala | Leu | Gly | Arg | |
| 405 | | | | | 410 | | | | 415 | | | | | | 420 | |
| TGT | ACC | CGG | GAT | AGC | TTT | GTG | AGG | GGG | TTG | AGC | TTT | GCT | AGA | TCT | GGG | 1688 |
| Cys | Thr | Arg | Asp | Ser | Phe | Val | Arg | Gly | Leu | Ser | Phe | Ala | Arg | Ser | Gly | |
| | | | | 425 | | | | | 430 | | | | | 435 | | |
| GGT | GAT | TGG | GCG | GAG | TGT | TTT | GCT | TAGCTGAATT | | ACCTTGATGA | | ATGGTATGTA | | | | 1742 |
| Gly | Asp | Trp | Ala | Glu | Cys | Phe | Ala | | | | | | | | | |
| | | | 440 | | | | | 445 | | | | | | | | |

```
TCACATTGCA  TATCATTAGC  ACTTCAGGTA  TGTATTATCG  AAGATGTATA  TCGAAAGGAT   1802
CAATGGTGAC  TGTCACTGGT  TATCTGAATA  TCCCTCTATA  CCTCGTCCCA  CAACCAATCA   1862
TCACCCTTTA  AACAATCACA  CTCAACGCAC  AGCGTACAAA  CGAACAAACG  CACAAAGAAT   1922
ATTTTACACT  CCTCCCCAAC  GCAATACCAA  CCGCAATTCA  TCATACCTCA  TATAAATACA   1982
ATACAATACA  ATACATCCAT  CCCTACCCTC  AAGTCCACCC  ATCCTATAAT  CAATCCCTAC   2042
TTACTTACTT  CTCCCCCTCC  CCCTCACCCT  TCCCAGAACT  CACCCCCGAA  GTAGTAATAG   2102
TAGTAGTAGA  AGAAGCAGAC  GACCTCTCCA  CCAATCTCTT  CGGCCTCTTA  TCCCCATACG   2162
CTACACAAAA  CCCCCACCCC  GTTAGCATGC  ACTCAGAAAA  TAATCAAAAA  TAACTAAGAA   2222
GGAAAAAAAA  GAAGAAGAAA  GGTTACATAC  TCCTCTCATA  CAAACTCCAA  GACGTATACA   2282
TCAAGATGGG  CAATCCCACC  ATTACTGATA  TCCATCTATG  AACCCATTCC  CATCCCACGT   2342
TAGTTGATTA  CTTTACTTAG  AAGAAGAAAA  AGGGAAGGGA  AGGGAAAGAA  GTGGATGGGA   2402
TTGAGTTAGT  GCTCACCGTC  TCGCAGCAAG  TTTATATTCT  TTTGTTTGGC  GGATATCTTT   2462
CACTGCTCCT  GCTGGACGTT  GTCACGGGGT  GGTAGTGGTT  GGCGGTGGTG  AGGGTCCATG   2522
ATCACTCTTG  GTTTGGGGGG  TTGTTGTTGT  CGTTGTTGTT  GTTGTTGGGT  GGGCATTTTC   2582
TTTTCTTCAC  TTGGGGATTA  TTATTTGGAA  TTGGTTAGTT  TGAGTGAGTG  GGTAATATTG   2642
AATGGGTGAT  TATTGGGAAT  GAAGTAGATT  TGGCTATGAA  TGGTTGATGG  GATGGAATGA   2702
ATGGATGGAT  GAATAGATGG  AGGCGGAAAA  GTCAGGTGGT  TTGAGGTTCG  GATTATTATC   2762
TTTGTGCCTG  AGGCATCACT  CTCCATCTAT  GTTGTTCTTT  CTATACCGAT  CTACCAGAGC   2822
TAAGTTGACT  GATTCTACCA  CAGTGCACAA  TAAGTATGTA  CTTATTTCAT  TTAGAGTATT   2882
TAGATTAACC  CGCTGTGCTA  TTTGCCGTAG  CTTTCCACCC  AATTTCGAAG  TTCGAAGAAT   2942
TAAAACTCAT  CCTACAGTAC  AGAATAGAAG  TAAAAGGAGA  AGAGAAAAAC  AAGATAATAC   3002
AACCAGTCCA  GGTCCATTCT  AGATCTCGAA  TGACCACCAA  ATAAGAAAGC  AACAAGCAAG   3062
TAAGCAAAGC  ATAAGTCTAA  ATGAACGCCA  ATAACTTCAT  CGCCTGCCTT  TGAAACTGAA   3122
CGCTATGCAC  GAATGGCTCG  AAATGATTCC  CTTAACTCCG  TAGTATTGAG  AGTGAGAGGA   3182
AAAGAAAAAA  AGAGACAGAA  AAGCTGACCA  TGGGAAAGAA  GCATGATCAG  TCGGGAATGG   3242
ATCTGCGGGT  TGAGATAGAT  ATGAGTTGCC  TCGCAGATCC  GGTGACAAGA  TAAGAGAATT   3302
GGGAGATGTG  ATCAGCCACT  GTAACTTCAT  CAAGCATCGA  CATTCAACGG  TCGGGTCTGC   3362
GGGTTGAGAT  GCAAGTTGAG  ATGCCACGCA  GACCCGAACA  GAGTGAGAGA  TGTGAGACTT   3422
TTGAACCACT  GTGACTTCAT  CAAGCATCAA  AACACACTCC  ATGGTCAATC  GGTTAGGGTG   3482
TGAGGGTTGA  TATGCCAGGT  TCGATGCCAC  GCAGACCCGA  ACCGACTGAG  AAATATGAAA   3542
AGTTGGACAG  CCACTTCATC  TTCATCAAGC  GTAAAACCCC  AATCAATGGT  AAATCGAAAA   3602
CGAATCTGCG  GGCTGATGTG  GAAATGAGAC  GAATGCCTCG  CAGATTCGAA  GACACGTAAA   3662
TCGAGATGAA  CAATCACTTT  AACTTCATCA  AAGCCTTAAA  TCACCCAATG  GCCAGTCTAT   3722
TCGGGTCTGC  GGGTTGAGGT  TCCTGTTGAG  ATGCCACGCA  GACTGCGAAC  ATGCGATGCA   3782
```

| | | | | | | |
|---|---|---|---|---|---|---|
| TTATAAGTTG | GACGAGTGTA | GACTGACCAT | TGATAACCGA | GATAAACAAT | CACTTCAACT | 3842 |
| TCATCAAAGC | CTTAAATCAC | TCAATGGCCA | GTCTGTTTGC | GGTCTGCGGG | CTGATACCCA | 3902 |
| AGTTGCGATG | CCACGCAGAC | TGCAAACATT | GATCGAGAGA | CGAGAAAAAC | AACGCACTTT | 3962 |
| AACTTCAACA | AAAGCCTTTC | AATCAGTCAA | TGGCCAGTCT | GTTCGCGGTC | TGCGGGCTGA | 4022 |
| TATGCGAGTT | GAGGTGCCTC | GCAGACCGCG | AACATGCGAT | GTAATTTCTT | AGTTAGACGA | 4082 |
| GTGCCTGGCC | ATTGAGAAAC | GAGAGAAACA | ACCACTTTAA | CTTCATGAAA | GCCTTGAACT | 4142 |
| ACTCAATGAC | CCGTCTGTTG | GCGGTCTGCG | GGCTGATATT | CGAGTTGAGA | TGCCACGCAG | 4202 |
| ACCGCCAACA | TGCGATGTAT | CATGTAAGTT | AGATGAGTGA | CTGGCCATTG | AGAAACGAGA | 4262 |
| GAAACAACCA | CACTTCATGA | GAGCCTTAAA | TTATTCAATG | ACCAGTCTGT | TCACGGTCTG | 4322 |
| CGGGTTGGTA | TGCGAGTCGA | GGTGCCTCGC | AGACCGCGAA | CATGCGATGT | TTTCGATGGA | 4382 |
| CGAGTGAAGC | CTGACGATCG | AGAACTATCT | CAGTTGGGTT | GGCCATTCGG | CTGGCCGTTG | 4442 |
| GGTTTAGTAT | TAGGATCGTC | AGGTTTGTCC | GATGGAACGT | TCCGTTTGCG | TGCGTTGGCG | 4502 |
| CGACGAGCCC | TCTCCTCGGC | GTGATTCTGA | AATTCTGCAA | TCAGGGCAGC | CGCAGCACGG | 4562 |
| CGACGGGACG | TCCTCCAGGA | GCTGTGTTGA | AGTTTCGGGG | TGGCGGTCCA | GAAGGGGGAG | 4622 |
| TTACATTAAA | AGCCTCATAG | ATGTCTTTGG | GTGGTTCCGG | GGGGCCCATC | GCAAGATCTT | 4682 |
| CTGGAGTTGT | GCGTCTGATC | ATCTCTTGAG | TGTAATTGCG | ACGCAGACCG | AGCTTCAGGA | 4742 |
| TTTTGGAAGG | GCTGGATCGC | TCCTGCTGAC | TCTTTCCCTC | AGCGGGCTTC | GTCTCGGCAG | 4802 |
| TCTTCATTTC | GGCGGGCTGA | TCTTCCATCT | CAGAATGGGA | TCGCTTTCTG | GTCGCTGCAC | 4862 |
| CCGCTCCTCC | CTTCAAGGTC | AGCTTGATGC | GCAGCGTCTT | GGGCGGCTCA | GCTGGTGGAG | 4922 |
| TTGGTTCCGG | CTCTGGCTCC | CTCCGGCGTC | GCTTGGGCAC | TTGAGTAGTC | TCTGAGGCTT | 4982 |
| CGCCGCGGCG | CCGTTTGCGA | GTCGGCTCCT | TGGTCTCTTT | GGCCTCTTTC | ACTTCACCTG | 5042 |
| GACCGTCTTT | CGGGGCGGTT | TCATCGTGCT | GAGCGATCAA | GGTTTGGATG | TAGGCAGCCG | 5102 |
| GCATCATTCG | ATCAACGGCA | ATTCCTCTCT | TGCGGGCCTC | CTCCCGAGCC | TTGATTGTCG | 5162 |
| CCTTGACCTC | GTCCACGTTT | TCGAAGAAGA | AAGGCATCTT | GTTATCCTGA | GGCAAGTTGC | 5222 |
| GCTCTCCCAT | GCGTGGGGAT | ATCCGAAGAT | GCGGTCCTTC | TCGAACTGTT | CATGAGACTT | 5282 |
| CAGACGAATT | GGAGGCTGGG | GGAGCAATTT | GTCTCCGTAG | GTGTTGTTAG | GGCGGAACCA | 5342 |
| AGAATAGCCT | TCGCCTACAA | CGACAAGCTC | TTCGCCAAAT | TTATTTTTT | GGCCTGTAAA | 5402 |
| AACGAACCCA | TCCTCGTCAG | TCCACCGGTG | CGTCTCGGAC | GTAGAGATTG | GCTTACTTAT | 5462 |
| TCCCTCAACG | CCGATCTCTG | CCTGGGGCTG | CGCTTCGGAT | GCGGCCTCGG | TCACGGCTCC | 5522 |
| GCCTCGGACT | GCACCGCTGG | AGTTTCGGTC | TTCTTCTCCT | GCTTCTCCAG | GTACTCCTTG | 5582 |
| CGTAACTCTT | CGATCAGCCT | CGGCTTCCGA | TGACTGCTCA | AATTCTGGAG | CAACAGCTGC | 5642 |
| CGCGGCCAGG | TCAAGCAGGC | GGTTTGCTAA | AACTGCCCAT | TTTCCATCGA | CACCTGCCTC | 5702 |
| CGACGCCTGT | GCAAAACCAG | CTGTTTTCGC | ATTGGCCTGT | TTGTTGGCAC | GCGTCTTCTT | 5762 |
| GACTGCTGCC | TTGCCCTTTA | CTTCCTTGAG | AGCAGACTCT | GGCTTAGATG | ATGGTGCACG | 5822 |
| GTTTCTGCGG | AAGCGCCGCT | CAGATTCCAA | AGATTCCATA | GCTTTAATGG | TAGGCTTTCT | 5882 |
| GGTTCTTCCA | GAAGTGCGCG | CAGCTGACGT | AGTGGTTGAG | TAGCTGGCAG | TTGGGGATCC | 5942 |
| TGGGCCCTCA | TTGGAACCAT | CAAGACCAAA | TTTGTTTCCA | TACATATCAG | CATGGTATTC | 6002 |
| AAAAGGAAAA | CTTTCGCCGT | ACGGAGTACT | GCGTTCGATT | CCGGGTGTAT | CCAAGTCGTA | 6062 |
| TCCAGACATG | GTGTCGAATT | CAGCCTTGCT | GTCAAGAGCA | GGGGTACTTT | CAATGCTGTC | 6122 |
| AGCAACCACG | CGGCCAAAGG | GCGTCTTCGG | GAAAGAAGGT | GTTTCAAGAG | AAGCGTCATC | 6182 |

| | | | | | | |
|---|---|---|---|---|---|---|
| CACGGCCTGG | CTTGCGGCGT | TGATTGCAGA | CTTTCGAGTA | GATCGCTGAG | GTCGCGAACT | 6242 |
| GGTTCGAGTA | GCAACCTGTG | AATTGGCAGC | CTTGTGACTG | CTTCGATTCA | CTGCAGAGAC | 6302 |
| GGAGTAGACT | GCACTGATTT | GGAATTCTGA | GTCGCAGCCA | TTCTGGATTT | GCGTTCGGCG | 6362 |
| CGACGAGATC | TCGCAGTCGT | GGTACGAGGA | GTAGAGCGAG | GCTGCGTAGC | AGTGTTGCAA | 6422 |
| GCTTGGTGCT | AGCCTCCTGG | GCTTCAGCAG | CTTCAGCAGT | GGTGGCAGAC | GCAGCAGAAT | 6482 |
| TAGCGGAGCT | TTATCGGCTT | TGCCGCTCTG | AGCGTTGGGA | GTAGAAGTGA | GAGAAGAGGT | 6542 |
| AGAGTCCACG | GAAGAAGTCT | TCTCGCTGTT | CTCAAAGCCG | TTCAGCTTTG | CTGGCATAGA | 6602 |
| CTTACGCGTC | TTGCGGCTGT | TGGAAGCGGA | AGAGTTCATG | GCGGGAGAGG | AGACGTTAGA | 6662 |
| AGTAGACATG | GTGGGGTTTG | TTGACGGGTT | TTGAGTAACA | AGAGACTTGC | GTCGATCTTT | 6722 |
| GAGTGTTCTT | GACAGAAAGT | TATGCAACGT | CGAC | | | 6756 |

( 2 ) INFORMATION FOR SEQ ID NO:32:

( i ) SEQUENCE CHARACTERISTICS:
        ( A ) LENGTH: 467 amino acids
        ( B ) TYPE: amino acid
        ( D ) TOPOLOGY: linear ( i i ) MOLECULE TYPE: protein ( x i ) SEQUENCE DESCRIPTION: SEQ ID NO:32:

```
Met   Gly   Val   Ser   Ala   Val   Leu   Leu   Pro   Leu   Tyr   Leu   Leu   Ser   Gly   Val
-23         -20                           -15                           -10

Thr   Ser   Gly   Leu   Ala   Val   Pro   Ala   Ser   Arg   Asn   Gln   Ser   Ser   Cys   Asp
            -5                            1                       5

Thr   Val   Asp   Gln   Gly   Tyr   Gln   Cys   Phe   Ser   Glu   Thr   Ser   His   Leu   Trp
10                            15                      20                              25

Gly   Gln   Tyr   Ala   Pro   Phe   Phe   Ser   Leu   Ala   Asn   Glu   Ser   Val   Ile   Ser
                        30                            35                        40

Pro   Glu   Val   Pro   Ala   Gly   Cys   Arg   Val   Thr   Phe   Ala   Gln   Val   Leu   Ser
                  45                            50                        55

Arg   His   Gly   Ala   Arg   Tyr   Pro   Thr   Asp   Ser   Lys   Gly   Lys   Lys   Tyr   Ser
            60                            65                        70

Ala   Leu   Ile   Glu   Glu   Ile   Gln   Gln   Asn   Ala   Thr   Thr   Phe   Asp   Gly   Lys
      75                            80                        85

Tyr   Ala   Phe   Leu   Lys   Thr   Tyr   Asn   Tyr   Ser   Leu   Gly   Ala   Asp   Asp   Leu
90                            95                      100                             105

Thr   Pro   Phe   Gly   Glu   Gln   Glu   Leu   Val   Asn   Ser   Gly   Ile   Lys   Phe   Tyr
                        110                           115                             120

Gln   Arg   Tyr   Glu   Ser   Leu   Thr   Arg   Asn   Ile   Val   Pro   Phe   Ile   Arg   Ser
                  125                           130                       135

Ser   Gly   Ser   Ser   Arg   Val   Ile   Ala   Ser   Gly   Lys   Lys   Phe   Ile   Glu   Gly
                  140                           145                       150

Phe   Gln   Ser   Thr   Lys   Leu   Lys   Asp   Pro   Arg   Ala   Gln   Pro   Gly   Gln   Ser
      155                           160                       165

Ser   Pro   Lys   Ile   Asp   Val   Val   Ile   Ser   Glu   Ala   Ser   Ser   Ser   Asn   Asn
170                           175                       180                             185

Thr   Leu   Asp   Pro   Gly   Thr   Cys   Thr   Val   Phe   Glu   Asp   Ser   Glu   Leu   Ala
                        190                           195                             200

Asp   Thr   Val   Glu   Ala   Asn   Phe   Thr   Ala   Thr   Phe   Val   Pro   Ser   Ile   Arg
                  205                           210                       215

Gln   Arg   Leu   Glu   Asn   Asp   Leu   Ser   Gly   Val   Thr   Leu   Thr   Asp   Thr   Glu
                  220                           225                       230
```

```
Val  Thr  Tyr  Leu  Met  Asp  Met  Cys  Ser  Phe  Asp  Thr  Ile  Ser  Thr  Ser
     235                 240                      245

Thr  Val  Asp  Thr  Lys  Leu  Ser  Pro  Phe  Cys  Asp  Leu  Phe  Thr  His  Asp
250                      255                 260                           265

Glu  Trp  Ile  Asn  Tyr  Asp  Tyr  Leu  Gln  Ser  Leu  Lys  Lys  Tyr  Tyr  Gly
                    270                 275                           280

His  Gly  Ala  Gly  Asn  Pro  Leu  Gly  Pro  Thr  Gln  Gly  Val  Gly  Tyr  Ala
               285                      290                      295

Asn  Glu  Leu  Ile  Ala  Arg  Leu  Thr  His  Ser  Pro  Val  His  Asp  Asp  Thr
          300                      305                      310

Ser  Ser  Asn  His  Thr  Leu  Asp  Ser  Ser  Pro  Ala  Thr  Phe  Pro  Leu  Asn
     315                      320                      325

Ser  Thr  Leu  Tyr  Ala  Asp  Phe  Ser  His  Asp  Asn  Gly  Ile  Ile  Ser  Ile
330                           335                 340                      345

Leu  Phe  Ala  Leu  Gly  Leu  Tyr  Asn  Gly  Thr  Lys  Pro  Leu  Ser  Thr  Thr
               350                      355                      360

Thr  Val  Glu  Asn  Ile  Thr  Gln  Thr  Asp  Gly  Phe  Ser  Ser  Ala  Trp  Thr
               365                      370                 375

Val  Pro  Phe  Ala  Ser  Arg  Leu  Tyr  Val  Glu  Met  Met  Gln  Cys  Gln  Ala
          380                      385                      390

Glu  Gln  Glu  Pro  Leu  Val  Arg  Val  Leu  Val  Asn  Asp  Arg  Val  Val  Pro
     395                      400                 405

Leu  His  Gly  Cys  Pro  Val  Asp  Ala  Leu  Gly  Arg  Cys  Thr  Arg  Asp  Ser
410                      415                 420                      425

Phe  Val  Arg  Gly  Leu  Ser  Phe  Ala  Arg  Ser  Gly  Gly  Asp  Trp  Ala  Glu
                    430                      435                      440

Cys  Phe  Ala
```

( 2 ) INFORMATION FOR SEQ ID NO:33:

( i ) SEQUENCE CHARACTERISTICS:
        ( A ) LENGTH: 1404 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Aspergillus ficuum (Aspergillus niger)
        ( B ) STRAIN: NRRL 3135

( x i ) SEQUENCE DESCRIPTION: SEQ ID NO:33:

```
ATGGGCGTCT  CTGCTGTTCT  ACTTCCTTTG  TATCTCCTGT  CTGGAGTCAC  CTCCGGACTG   60
GCAGTCCCCG  CCTCGAGAAA  TCAATCCAGT  TGCGATACGG  TCGATCAGGG  GTATCAATGC  120
TTCTCCAGAGA CTTCGCATCT  TTGGGGTCAA  TACGCACCGT  TCTTCTCTCT  GGCAAACGAA  180
TCGGTCATCT  CCCCTGAGGT  GCCCGCCGGA  TGCAGAGTCA  CTTTCGCTCA  GGTCCTCTCC  240
CGTCATGGAG  CGCGGTATCC  GACCGACTCC  AAGGGCAAGA  AATACTCCGC  TCTCATTGAG  300
GAGATCCAGC  AGAACGCGAC  CACCTTTGAC  GGAAAATATG  CCTTCCTGAA  GACATACAAC  360
TACAGCTTGG  GTGCAGATGA  CCTGACTCCC  TTCGGAGAAC  AGGAGCTAGT  CAACTCCGGC  420
ATCAAGTTCT  ACCAGCGGTA  CGAATCGCTC  ACAAGGAACA  TCGTTCCATT  CATCCGATCC  480
TCTGGCTCCA  GCCGCGTGAT  CGCCTCCGGC  AAGAAATTCA  TCGAGGGCTT  CCAGAGCACC  540
```

```
AAGCTGAAGG  ATCCTCGTGC  CCAGCCCGGC  CAATCGTCGC  CCAAGATCGA  CGTGGTCATT      600

TCCGAGGCCA  GCTCATCCAA  CAACACTCTC  GACCCAGGCA  CCTGCACTGT  CTTCGAAGAC      660

AGCGAATTGG  CCGATACCGT  CGAAGCCAAT  TTCACCGCCA  CGTTCGTCCC  CTCCATTCGT      720

CAACGTCTGG  AGAACGACCT  GTCCGGTGTG  ACTCTCACAG  ACACAGAAGT  GACCTACCTC      780

ATGGACATGT  GCTCCTTCGA  CACCATCTCC  ACCAGCACCG  TCGACACCAA  GCTGTCCCCC      840

TTCTGTGACC  TGTTCACCCA  TGACGAATGG  ATCAACTACG  ACTACCTCCA  GTCCTTGAAA      900

AAGTATTACG  GCCATGGTGC  AGGTAACCCG  CTCGGCCCGA  CCCAGGGCGT  CGGCTACGCT      960

AACGAGCTCA  TCGCCCGTCT  GACCCACTCG  CCTGTCCACG  ATGACACCAG  TTCCAACCAC     1020

ACTTTGGACT  CGAGCCCGGC  TACCTTTCCG  CTCAACTCTA  CTCTCTACGC  GGACTTTTCG     1080

CATGACAACG  GCATCATCTC  CATTCTCTTT  GCTTTAGGTC  TGTACAACGG  CACTAAGCCG     1140

CTATCTACCA  CGACCGTGGA  GAATATCACC  CAGACAGATG  GATTCTCGTC  TGCTTGGACG     1200

GTTCCGTTTG  CTTCGCGTTT  GTACGTCGAG  ATGATGCAGT  GTCAGGCGGA  GCAGGAGCCG     1260

CTGGTCCGTG  TCTTGGTTAA  TGATCGCGTT  GTCCCGCTGC  ATGGGTGTCC  GGTTGATGCT     1320

TTGGGGAGAT  GTACCCGGGA  TAGCTTTGTG  AGGGGGTTGA  GCTTTGCTAG  ATCTGGGGT     1380

GATTGGGCGG  AGTGTTTTGC  TTAG                                              1404
```

( 2 ) INFORMATION FOR SEQ ID NO:34:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO:34:

```
GGGTAGAATT  CAAAAATGGG  CGTCTCTGCT  GTTCTA                                   36
```

( 2 ) INFORMATION FOR SEQ ID NO:35:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO:35:

```
AGTGACGAAT  TCGTGCTGGT  GGAGATGGTG  TCG                                      33
```

( 2 ) INFORMATION FOR SEQ ID NO:36:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO:36:

```
GAGCACCAAG  CTGAAGGATC  C                                                    21
```

( 2 ) INFORMATION FOR SEQ ID NO:37:

( i ) SEQUENCE CHARACTERISTICS:
           ( A ) LENGTH: 34 base pairs
           ( B ) TYPE: nucleic acid
           ( C ) STRANDEDNESS: single
           ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO:37:

AAACTGCAGG CGTTGAGTGT GATTGTTTAA AGGG                34

( 2 ) INFORMATION FOR SEQ ID NO:38:

( i ) SEQUENCE CHARACTERISTICS:
           ( A ) LENGTH: 42 base pairs
           ( B ) TYPE: nucleic acid
           ( C ) STRANDEDNESS: single
           ( D ) TOPOLOGY: linear ( i i i ) HYPOTHETICAL: NO ( v i ) ORIGINAL SOURCE:
           AG-1

( x i ) SEQUENCE DESCRIPTION: SEQ ID NO:38:

GACAATGGCT ACACCAGCAC CGCAACGGAC ATTGTTTGGC CC         42

( 2 ) INFORMATION FOR SEQ ID NO:39:

( i ) SEQUENCE CHARACTERISTICS:
           ( A ) LENGTH: 24 base pairs
           ( B ) TYPE: nucleic acid
           ( C ) STRANDEDNESS: single
           ( D ) TOPOLOGY: linear ( i i ) MOLECULE TYPE: DNA (synthetic)

( i i i ) HYPOTHETICAL: NO ( v i ) ORIGINAL SOURCE:
           AG-2

( x i ) SEQUENCE DESCRIPTION: SEQ ID NO:39:

AAGCAGCCAT TGCCCGAAGC CGAT                               24

( 2 ) INFORMATION FOR SEQ ID NO:40:

( i ) SEQUENCE CHARACTERISTICS:
           ( A ) LENGTH: 21 base pairs
           ( B ) TYPE: nucleic acid
           ( C ) STRANDEDNESS: single
           ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO:40:

CTCTGCAGGA ATTCAAGCTA G                                   21

( 2 ) INFORMATION FOR SEQ ID NO:41:

( i ) SEQUENCE CHARACTERISTICS:
           ( A ) LENGTH: 36 base pairs
           ( B ) TYPE: nucleic acid
           ( C ) STRANDEDNESS: single ( D ) TOPOLOGY: linear ( i i ) MOLECULE TYPE: DNA (synthetic)

( i i i ) HYPOTHETICAL: NO ( v i ) ORIGINAL SOURCE:
    18-2

( x i ) SEQUENCE DESCRIPTION: SEQ ID NO:41:

CGAGGCGGGG ACTGCCAGTG CCAACCCTGT GCAGAC                    36

( 2 ) INFORMATION FOR SEQ ID NO:42:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA (synthetic)

( i i i ) HYPOTHETICAL: NO ( v i ) ORIGINAL SOURCE:
    18-3

( x i ) SEQUENCE DESCRIPTION: SEQ ID NO:42:

GTCTGCACAG GGTTGGCACT GGCAGTCCCC GCCTCG                    36

( 2 ) INFORMATION FOR SEQ ID NO:43:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO:43:

GGCACGAGGA TCCTTCAGCT T                                    21

( 2 ) INFORMATION FOR SEQ ID NO:44:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO:44:

AATTCAAGCT TG                                              12

( 2 ) INFORMATION FOR SEQ ID NO:45:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA (synthetic)

( i i i ) HYPOTHETICAL: NO (vi) ORIGINAL SOURCE:
    24-2

(xi) SEQUENCE DESCRIPTION: SEQ ID NO:45:

CGAGCCGGGG ACTGCCAGGC GCTTGGAAAT CACATT                    36

(2) INFORMATION FOR SEQ ID NO:46:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (vi) ORIGINAL SOURCE:
        24-3

(xi) SEQUENCE DESCRIPTION: SEQ ID NO:46:

AATGTGATTT CCAAGCGCCT GGCAGTCCCC GCCTCG                    36

(2) INFORMATION FOR SEQ ID NO:47:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (vi) ORIGINAL SOURCE:
        fyt-2

(xi) SEQUENCE DESCRIPTION: SEQ ID NO:47:

AACAGCAGAG ACGCCCATTG CTGAGGTGTA ATGATG                    36

(2) INFORMATION FOR SEQ ID NO:48:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (vi) ORIGINAL SOURCE:
        fyt-3

(xi) SEQUENCE DESCRIPTION: SEQ ID NO:48:

CATCATTACA CCTCAGCAAT GGGCGTCTCT GCTGTT                    36

(2) INFORMATION FOR SEQ ID NO:49:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO

-continued ( x i ) SEQUENCE DESCRIPTION: SEQ ID NO:49:

AGCTTCCCCG GTAC 14

( 2 ) INFORMATION FOR SEQ ID NO:50:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO:50:

AGCTCCCCCG GATC 14

( 2 ) INFORMATION FOR SEQ ID NO:51:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO:51:

AGCTAGGGGG 10

( 2 ) INFORMATION FOR SEQ ID NO:52:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO:52:

TCGACCCCCT 10